(12) United States Patent
Ebbini et al.

(10) Patent No.: US 11,116,474 B2
(45) Date of Patent: Sep. 14, 2021

(54) ULTRASOUND IMAGE FORMATION AND/OR RECONSTRUCTION USING MULTIPLE FREQUENCY WAVEFORMS

(71) Applicant: REGENTS OF THE UNIVERSITY OF MINNESOTA, Minneapolis, MN (US)

(72) Inventors: Emad S. Ebbini, Edina, MN (US); Dalong Liu, Issaquah, WA (US); Andrew J. Casper, Eau Claire, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 1536 days.

(21) Appl. No.: 14/904,568

(22) PCT Filed: Jul. 21, 2014

(86) PCT No.: PCT/US2014/047430
§ 371 (c)(1),
(2) Date: Jan. 12, 2016

(87) PCT Pub. No.: WO2015/013196
PCT Pub. Date: Jan. 29, 2015

(65) Prior Publication Data
US 2016/0143617 A1    May 26, 2016

Related U.S. Application Data

(60) Provisional application No. 61/857,442, filed on Jul. 23, 2013.

(51) Int. Cl.
*A61B 8/14* (2006.01)
*A61B 8/08* (2006.01)
(Continued)

(52) U.S. Cl.
CPC .............. *A61B 8/14* (2013.01); *A61B 8/0891* (2013.01); *A61B 8/4438* (2013.01);
(Continued)

(58) Field of Classification Search
CPC ....... A61B 8/14; A61B 8/4438; A61B 8/0891; A61B 8/5207; G01S 15/8959;
(Continued)

(56) References Cited

U.S. PATENT DOCUMENTS 5,694,936 A    12/1997  Fujimoto
5,906,580 A    5/1999   Kline-Schoder
(Continued)

FOREIGN PATENT DOCUMENTS

CN    101179998 A    5/2008
CN    102788836 A    11/2012
(Continued)

OTHER PUBLICATIONS

Ainsworth, "3D ultrasound measurement of change in carotid plaque volume—A tool for rapid evaluation of new therapies," 2005. *Stroke.* 36(9):1904-1909.
(Continued)

*Primary Examiner* — Jeffrey G Hoekstra
*Assistant Examiner* — Katherine M McDonald
(74) *Attorney, Agent, or Firm* — Mueting Raasch Group

(57) ABSTRACT

Ultrasound adaptive imaging methods and/or systems provide for modification of waveform generation to drive a plurality of transducer elements. The modification may be based on at least one of contrast ratio or signal to noise ratio as determined with respect to control points in a region of interest. Further, image reconstruction may be performed upon separating, from pulse echo data received, at least a portion thereof received at each ultrasound transducer element from the region of interest in response to the delivered
(Continued)

ultrasound energy corresponding to a single frequency of one or more image frequencies within a transducer apparatus bandwidth. The image reconstructed from the separated pulse-echo data corresponding to the single frequency of the one or more image frequencies may be used alone or combined with like image data (e.g., to provide an image representative of one or more properties in the region of interest).

15 Claims, 18 Drawing Sheets

(51) Int. Cl.
*A61N 7/00* (2006.01)
*G01S 15/89* (2006.01)
*G01S 7/52* (2006.01)
*A61B 8/00* (2006.01)

(52) U.S. Cl.
CPC .............. *A61B 8/5207* (2013.01); *A61N 7/00* (2013.01); *G01S 7/5202* (2013.01); *G01S 7/52046* (2013.01); *G01S 15/8915* (2013.01); *G01S 15/8952* (2013.01); *G01S 15/8959* (2013.01); *G01S 15/8997* (2013.01)

(58) Field of Classification Search
CPC ............. G01S 15/8915; G01S 15/8997; G01S 7/5202; G01S 7/52046; A61N 7/00
See application file for complete search history.

(56) References Cited

U.S. PATENT DOCUMENTS

| | | |
|---|---|---|
| 6,172,939 B1 | 1/2001 | Cole |
| 6,277,075 B1 | 8/2001 | Torp |
| 6,492,762 B1 | 12/2002 | pant |
| 6,494,839 B1 | 12/2002 | Averkiou |
| 6,540,677 B1 | 4/2003 | Angelson |
| 6,618,493 B1 | 9/2003 | Torp |
| 6,705,993 B2 | 3/2004 | Ebbini |
| 6,770,031 B2 | 8/2004 | Hynynen et al. |
| 6,951,540 B2 | 10/2005 | Ebbini |
| 7,063,666 B2 | 6/2006 | Weng et al. |
| 7,686,764 B2 | 3/2010 | Watanabe et al. |
| 7,901,358 B2 | 3/2011 | Mehi |
| 8,002,705 B1 | 8/2011 | Napolitano |
| 8,086,296 B2 | 12/2011 | Bystritsky |
| 8,591,419 B2 | 11/2013 | Tyler |
| 8,911,372 B2 | 12/2014 | Yoshikawa et al. |
| 8,939,909 B2 | 1/2015 | Wegner |
| 9,144,693 B2 | 9/2015 | Appelman |
| 9,592,409 B2 | 3/2017 | Yoo |
| 9,610,061 B2 | 4/2017 | Ebbini et al. |
| 10,231,712 B2 | 3/2019 | Ebbini et al. |
| 2001/0017937 A1 | 5/2001 | Bonnefous |
| 2001/0029336 A1 | 10/2001 | Teo |
| 2001/0039381 A1* | 11/2001 | Burns .................... A61B 8/06 600/443 |
| 2003/0097068 A1* | 5/2003 | Hossack ............... G01S 15/899 600/443 |
| 2003/0220636 A1 | 11/2003 | Bowman |
| 2003/0225331 A1 | 12/2003 | Diederich |
| 2004/0015079 A1 | 1/2004 | Berger |
| 2004/0106880 A1 | 6/2004 | Weng |
| 2004/0210135 A1 | 10/2004 | Hynynen |
| 2005/0070796 A1 | 3/2005 | Tsujita |
| 2005/0102009 A1 | 5/2005 | Costantino |
| 2005/0249667 A1 | 11/2005 | Tuszynski |
| 2005/0267453 A1 | 12/2005 | Wong et al. |
| 2007/0016040 A1 | 1/2007 | Nita |
| 2007/0038100 A1 | 2/2007 | Nita |
| 2007/0055155 A1 | 3/2007 | Owen |
| 2007/0129633 A1 | 6/2007 | Lee et al. |
| 2008/0015440 A1 | 1/2008 | Shandas |
| 2008/0027320 A1 | 1/2008 | Bolorforosh |
| 2008/0045882 A1 | 2/2008 | Finsterwald |
| 2008/0221448 A1 | 9/2008 | Khuri-Yakub et al. |
| 2008/0228075 A1 | 9/2008 | Fraser |
| 2009/0048546 A1 | 2/2009 | Appelman et al. |
| 2009/0069677 A1* | 3/2009 | Chen ........................ A61N 7/02 600/439 |
| 2009/0069680 A1 | 3/2009 | Yasuhiko |
| 2010/0004540 A1 | 1/2010 | Thiele |
| 2010/0286520 A1 | 11/2010 | Hazard |
| 2011/0112405 A1 | 5/2011 | Barthe |
| 2011/0248714 A1 | 10/2011 | Salomir |
| 2012/0053391 A1 | 3/2012 | Mishelevich |
| 2012/0083692 A1 | 4/2012 | Stoll |
| 2012/0283502 A1 | 8/2012 | Mishelevich |
| 2012/0283564 A1 | 11/2012 | Ebbini |
| 2012/0289869 A1 | 11/2012 | Tyler |
| 2013/0123635 A1 | 5/2013 | Wegner |
| 2013/0144165 A1 | 6/2013 | Ebbini |
| 2014/0343463 A1 | 11/2014 | Mishelevich |
| 2015/0251025 A1 | 9/2015 | You |
| 2017/0080255 A1 | 3/2017 | Law |
| 2017/0224990 A1 | 8/2017 | Goldwasser |
| 2017/0296140 A1 | 10/2017 | Ebbini |
| 2019/0160309 A1 | 5/2019 | Ebbini |
| 2019/0269385 A1 | 9/2019 | Ebbini et al. |
| 2019/0308036 A1 | 10/2019 | Ebbini |
| 2020/0121960 A1 | 4/2020 | Darrow et al. |

FOREIGN PATENT DOCUMENTS

| | | |
|---|---|---|
| CN | 102800071 A | 11/2012 |
| EP | 0392743 A1 | 10/1990 |
| EP | 2310094 B1 | 10/2014 |
| WO | WO 2006018761 A1 | 2/2006 |
| WO | WO 2006/042201 A1 | 4/2006 |
| WO | WO 2006/090298 A1 | 8/2006 |
| WO | WO 2008/053457 A2 | 5/2008 |
| WO | WO 2009/002492 A1 | 12/2008 |
| WO | WO 2009/050719 A2 | 4/2009 |
| WO | WO 2011/156624 A2 | 12/2011 |
| WO | WO 2012/033584 A2 | 3/2012 |
| WO | WO 2012/142455 A2 | 10/2012 |
| WO | WO 2013/059833 A1 | 4/2013 |
| WO | WO 2015/013196 A2 | 1/2015 |

OTHER PUBLICATIONS

Amini, "Noninvasive Estimation of Tissue Temperature Via High-Resolution Spectral Analysis Techniques," Feb. 2005 *IEEE Transactions on Biomedical Engineering*,;52(2):221-228.

Arthur, "In vivo change in ultrasonic backscattered energy with temperature in motion-compensated images," 2008 *International Journal of Hyperthermia*, 24(5):389-398.

Aubry, "Transcostal high-intensity-focuses ultrasound: Ex vivo adaptive focusing feasibility study," 2008 *Phys. Med. Biol.*, 53:2937-2951.

Ballard, "Monitoring and Guidance of HIFU Beams with Dual-Mode Ultrasound Arrays," 31st *Annual International Conference of the IEEE EMBS*, Minneapolis, MN; Sep. 2-6, 2009:137-140.

Ballard, "Adaptive transthoracic refocusing of dual-mode ultrasound arrays," Jan. 2010 *IEEE Trans Bionred Eng.*, 57(1): 93-102.

Bischof, "Rectal Protection During Prostate Cryosurgery: Design and Characterization of an Insulating Probe," 1997 *Cryobiology*, 34:80-92.

Blake, "A Method to estimate wall shear rate with a clinical ultrasound scanner," 2008 *Ultrasound in Medicine and Biology*, 34(5):760-774.

Blana, "First analysis of the long-term results with transrectal HIFU in patients with localized prostate cancer," Jun. 2008 *Euro Urology*, 53(6):1194-1203.

Bohn, "An analysis package comparing pid antiwindup strategies," Apr. 1995 *Control Systems Magazine*, IEEE, 15(2):34-40.

(56) References Cited

OTHER PUBLICATIONS

Botros, "Two-step hybrid virtual array-ray (VAR) technique for focusing through the rib cage," Jul. 1998 *IEEE Trans. Ultrason. Ferroelectr., Freq. Control*, 45(4):989-1000.
Bracewell, "Two-dimensional Imaging" Prentice-Hall Signal Processing Series. 1995. Cover Page, Title Page, Copyright Page, and Table of Contents. 11 pages total.
Casper, "Realtime Control of Multiple-focus Phased Array Heating Patterns Based on Noninvasive Ultrasound Thermography," 2010 IEEE International Ultrasonics Symposium Proceedings, 467-470.
Casper, "Realtime Control of Multiple-focus Phased Array Heating Patterns Based on Noninvasive Ultrasound Thermography," Jan. 2012 *IEEE Trans. Biomed. Eng*., 59(1):95-105.
Cespedes, "Echo decorrelation from displacement gradients in elasticity and velocity estimation" 1999 *IEEE Trans. UFFC.*, 46:791-801.
Chan, "An image-guided high intensity focused ultrasound device for uterine fibroids treatment," 2002 *Med. Phys*., 29:2611-2620.
Chan, Chapter 2 "Basics of Ultrasound Imaging," Narouze (Ed.), *Atlas of Ultrasound-Guided Procedures in Interventional Pain Management*, Springer: New York, NY; 2011. Cover page, publisher's page, and pp. 13-19.
Chapelon, "New piezoelectric transducers for therapeutic ultrasound," Jan. 2000 *Ultrasound Med. Biol*., 26(1):153-159.
Chew, *Waves and Fields in Inhomogenous Media*, Van Nostrand Reinhold: New York; 1990. Cover Page, Title Page, Copyright Page, and Table of Contents. 12 pages total.
Chiao, "Coded excitation for diagnostic ultrasound: A system developer's perspective," Feb 2005 *IEEE Trans. Ultrason., Ferroelect., Freq. Colllr.*, 52(2):160-170.
Curiel, "1.5-D high intensity focused ultrasound array for non-invasive prostate cancer surgery," Feb 2002 *IEEE Trans. Ultrason., Ferroelectr., Freq. Control*, 49(2):231-242.
Dalong, "Viscoelastic property measurement in thin tissue constructs using ultrasound," 2008 *IEEE Trans. Ultrason. Ferroelecdt. Freq. Contr*., 55(2):368-383.
Davies, "Pulse wave analysis and pulse wave velocity: A critical review of their strengths and weaknesses" Mar 2003 *J Hypertens.*, 21(3):463-72.
Dunmire, "Cross-beam vector doppler ultrasound for angle-independent velocity measurements" Oct. 2000 *Ultrasound Med Biol*., 26(8):1213-1235.
Ebbini, "A cylindrical-section ultrasound phased-array applicator for hyperthermia cancer therapy," 1988 *IEEE Trans. Ultrasonics, Ferroelectrics, and Frequency Control*, 35(5):561-572.
Ebbini, "Multiple-focus ultrasound phased-array pattern synthesis: optimal driving-signal distributions for hyperthermia" Sep. 1989 *IEEE Trans Ultrason Ferroelectr Freq Control*., 36(5):540-8.
Ebbini, "Deep-localized hyperthermia with ultrasound phased arrays using the pseudoinverse pattern synthesis methods," Ph.D. Dissertation, University of Illinois, Urbana, IL; 1990.
Ebbini, "Experimental evaluation of a prototype cylindrical section ultrasound hyperthermia phased-array applicator," Sep. 1991 *IEEE Transactions on Ultrasonics Ferroelectrics and Frequency Control*, 38(5):510-520.
Ebbini, "Optimization of the intensity gain of multiple-focus phased-array heating patterns," 1991 *Int. J. Hyperthermia*, 7(6): 953-973.
Ebbini, "A spherical-section ultrasound phased array applicator for deep localized hyperthermia," Jul. 1991 *IEEE Trans. Biomedical Engineering*, 38(7):634-643.
Ebbini, "Optimal transversal filter bank for 3d real-Lime acoustical imaging," in Signals, Systems and Computers, 1992 Conference Record of the Twenty-Sixth Asilomar Conference 011, 2:831-835.
Ebbini, "A new Svd-based optimal inverse filter design for ultrasonic applications," in *Ultrasonics Symposium, 1993. Proceedings., IEEE*, 2:1187-1190.
Ebbini, "Fundamental resolution limits of a coded-excitation system for real-time pulse-echo imaging," in Nov. 1997 *Proceedings of the IEEE Ultrasonics Symposium 2*, 1997(2):1539-1542.
Ebbini, "Region-adaptive motion tracking of speckle imagery," 2000 *ICASSP, IEEE International Conference on Acoustics, Speech and Signal Processing—Proceedings*. 4:2075-2078.
Ebbini, "Lesion formation and visualization using dual-mode ultrasound phased arrays," Oct 2001 *Proc. IEEE Ultrason. Symp.*, 2:1351-1354.
Ebbini, "Dual-mode ultrasound phased arrays for image-guided surgery," Apr. 2006 *Ultrasonic Imaging*, 28(2):65-82.
Ebbini, "Phase-coupled two-dimensional speckle tracking algorithm," May 2006 *IEEE Trans Ultrason Ferroelectr Freq Control.*, 53(5):972-90.
Ebbini, "Monitoring and Guidance of Minimally-Invasive Thermal Therapy Using Diagnostic Ultrasound," $31^{st}$ *Annual International Conference of the IEEE EMBS*, Minneapolis, MN; Sep. 2-6, 2009:4283-4286.
Ebbini, "Guest Editorial to the Special Issue on Therapeutic Ultrasound: Current Status and Future Directions," Jan. 2010 *IEEE Transactions on Biomedical Engineering*, 57(1):57-60.
Ebbini, "Dereverberation of ultrasound echo data in vascular imaging applications" 2011, *ICASSP, IEEE International Conference on Acoustics, Speech and Signal Processing—Proceedings*. 2011: 741-744.
Figueroa, "A Computational Framework for Fluid-Solid-Growth Modeling in Cardiovascular Simulations" Sep. 2009 *Comput Methods Appl Mech Eng.*, 198(45-46):3583-3602.
Fink, "Time reversal of ultrasonic fields. I. Basic principles," Sep 1992 *IEEE Trans. Ultrason., Ferroelectr., Freq. Control*, 39(5):555-566.
Fleury, "New piezocomposite transducers capable of producing high-power levels suitable for therapy with reasonably wide bandwidth suitable for imaging," 2002 *Proc. $2^{nd}$ Int. Symp. Ther. Ultrasound*, 1:428-436.
Fung, Biomechanics: Circulation, $2^{nd}$ Ed. Springer, New York. 1997. Cover Page, Copyright Page, Table of Contents.
Gelet, "845 Prostate cancer control with transrectal HIFU in 242 consecutive patients: 5-year results" Jan. 2004 *European Urology Supplements* 3(2):214-214.
Goel, "Adjuvant Approaches to Enhance Cryosurgery," Jul. 2009 *Journal of Biomechanical Engineering*, 131(7): 074003.
Gronningsaeter, "Vessel wall detection and blood noise reduction in intravascular ultrasound imaging," May 1996; *IEEE Transactions on Ultrasonics, Ferroelectrics and Frequency Control, IEEE, US*, 43(3):359-369.
Haddadin, "Ultrasonic focusing through inhomogeneous media by application of the inverse scattering problem" Jul. 1998, *J Acoust Soc Am*., 104(1): 313-325.
Haddadin, "Imaging Strongly Scattering Media Using Multiple-frequency Distorted Born Iterative Method," 1998 I*EEE Trans. UFFC*, 5(6):1485-1496.
Haken, "Effect of mode conversion on ultrasonic heating oat tissue interfaces," 1992 *J. Ultrasound Med*., 11:393-405.
Hermus, "Advanced carotid plaque imaging" 2010 *European Journ. Of Vascular and Endovascular Surgery*, 39(2): 125-133.
Hindley, "MRI guidance of focused ultrasound therapy of uterine fibroids: Early results," Dec. 2004 *Am. J. Roentgenology*, 183(6):1713-1719.
Hirata, "Pulse wave analysis and pulse wave velocity: a review of blood pressure interpretation 100 years after Korotkov" Oct. 2006 *Circ J.*, 70(10): 1231-9.
Hynynen, "Trans-skull ultrasound therapy: The feasibility of using image-derived skull thickness information to correct the phase distortion," May 1999 *IEEE Trans. Ultrason, Ferroelectr., Freq. Control*, 46(5):752-755.
Ibbini, "N X N square-element ultrasound phased array applicator: Simulated temperature distributions associated with directly synthesized heating patterns," 1990 *IEEE Trans. Ultrason, Ferroelectr., Freq. Control*, 37(6):491-500.
Insana, "Maximum-likelihood approach to strain imaging using ultrasound" 2000 *J. Acoust. Soc. Am*., 107(3):1421-1434.
International Patent Application No. PCT/US2014/047430, filed Jul. 21, 2014; International Preliminary Report on Patentability dated Feb. 4, 2016; 13 pages.

(56) References Cited

OTHER PUBLICATIONS

International Patent Application No. PCT/US2014/047430, filed Jul. 21, 2014; International Search Report/Written Opinion dated Jan. 20, 2015; 17 pages.
Ishida, "Development and animal experiment of variable focusing HIFU system for prostate cancer treatment," 2003 $3^{rd}$ *Int. Symp. THer. Ultrasound*, 1:382-387.
Karimi, "Estimation of Nonlinear Mechanical Propcnics of Vascular Tissues via Elastography," Dec. 2008 *Cardiovasc Eng.*, 8(4): 191-202. doi: 10.1007/s10558-0089061-0.
Kim, "Arterial vulnerable plaque characterization using ultrasound-induced thermal strain imaging (TSI)," 2008 *IEEE Transaction on Biomedical engineering*, 55(1):171-180.
Lee, "High Intensity Focused Ultrasound Effect on Cardiac Tissues: Potential for Clinical Application," 2000 *Echocardiography*, 17(6):563-566.
Li, "A new filter design technique for coded excitation systems," 1992 *IEEE Trans. Ultrasonics, Ferroelectrics, and Frequency Control*, 39(6):693-699.
Li, "Blocked Element Compensations in Phased Array Imaging," 1993 *IEEE Trans. Ultrasonics, Ferroelectrics, and Frequency Control*, 40(4):283-292.
Lindsey, "Simultaneous bilateral real-time 3-d transcranial ultrasound imaging at 1 {MHz} through poor acoustic windows," *2013 Ultrasound in Medicine and Biology*, 39(4) 721-734, 2013. http://www.sciencedirect.com/science/article/pii/S0301562912007284.
Liu, "Viscoelastic property measurement in thin tissue constructs using ultrasound" 2008 *IEEE Trans. Ultrason. Ferroelect. Freq. Contr.* 55(2):368-383.
Liu, "Real-Time 2-D Temperature Imaging Using Ultrasound" Jan. 2010 *IEEE Trans Biomed Eng.*, 57(1):12-6.
Lubinski, "Speckle tracking methods for ultrasonic elasticity imaging using short-time correlation" 1999 *IEEE Trans. UFFC.*, 46:82-96.
Luo, "Pulse wave imaging of normal and aneurysmal abdominal aortas in vivo" Apr. 2009 *IEEE Trans Med Imaging.*, 28(4):477-86.
Maass-Moreno, "Noninvasive temperature estimation in tissue via ultrasound echo shifts. Part I. Theoretical model," 1996 *The Journal of the Acoustical Society of America*, 100(4.1):2514-2521.
Mahmoud, "In vivo vascular wall tissue characterization using a strain tensor measuring (STM) technique for flow-mediated vasodilation analyses" 2009 *Physics in Medicine and Biology*, 54(20):6217-6238.
Martin, "Investigation of HIFU produced emulsion for acoustic hemostasis," 2003 *Proc. 3Int. Symp. Ther. Ultrasound*, 1:351-356.
McGough, "Direct Computation of ultrasound phased-array driving signals from specified temperature distribution for hyperthermia," Aug. 1992 *IEEE Trans. Biomedical Engineering*, 39(8):825-835.
McGough, "Mode scanning: heating pattern synthesis with ultrasound phased arrays," 1994 *Int. Journal of Hyperthermia*, 10(3):433-442.
Miller, "Fundamental limitations of noninvasive temperature imaging by means of ultrasound echo strain estimation," 2002 *Ultrasound in Medicine and Biology*, 28(10)1319-1333.
Misaridis, "Use of modulated excitation signals in medical ultrasound. part I: basic concepts and expected benefits," Feb. 2005 *IEEE Trans. Ultrason., Ferroelect., Freq. Colltr.*, 52( 2): 177-191.
Montaldo, "Spatio-temporal coding in complex media for optimum beamforming: the iterative time-reversal approach," Feb. 2005 *IEEE Trans. Ultrason., Ferroelect., Freq. Comr.*, 52(2):220-230.
Mougenot, "Automatic spatial and temporal temperature control for Mr-guided focused ultrasound using fast 3D Mr thermometry and multispiral trajectory of the focal point," Nov. 2004 *Magnetic Resonance in Medicine*, 52(5):1005-1015.
Mougenot, "Three-dimensional spatial and temporal temperature control with Mr thermometry-guided focused ultrasound (mrghifu)," 2009 *Magnetic Resonance in Medicine*, 61:603-614.
Moyle, "Inlet conditions for image-based Cfd models of the Carotid bifurcation: Is it reasonable to assume fully developed flow?" 2006 *Journ. Of Biomechanical Engr. Transactions of the ASME*, 128(3):371-379.
Nichols, *McDonald's Blood Flow in Arteries*, Hodder Arnold: New York, NY; 2005. Cover page, title page and table of contents.
Nightingale, "On the feasibility of remote palpation using acoustic radiation force," Jul. 2001 *J. Acoust. Soc. Amer.*, 110:625-634.
O'Donnell, "Coded excitation for synthetic aperture ultrasound imaging," Feb 2005 *IEEE Tmns. Ultrason., Ferroelect., Freq. Contr.*, 52( 2):171-176.
Pernot, "High power density prototype for high precision transcranial therapy," 2003 *Proc. $3^{rd}$ Int. Symp. Ther. Ultrasound*, 1:405-410.
Pernot, "Temperature estimation using ultrasonic spatial compounding," 2004 IEEE *Trans. Ultrason., Ferroelect., Freq. Contr.*, 51(5):606-615.
Pesavento, "A time efficient and accurate strain estimation concept for ultrasonic elastography using iterative phase zero estimation" 1999 *IEEE Trans. UFFC*, 46(5): 1057-1067.
Poissonnier, "Control of prostate cancer by transrectal HIFU in 227 patients," 2007 *Eur. Urol.*, 51:381-387.
Prada, "The iterative time reversal process: Analysis of the convergence," 1995 *J. Acoust. Soc. Amer.*, 95:62-71.
Praivianik, "Thermoacoustic and photoacoustic sensing of temperature," Sep 2009 *Journal of Biomedical Optics*, 14(5): 054024.
Rabben, "Ultrasound-based vessel wall tracking: an autocorrelation technique with RF center frequency estimation" 2002 *Ultrasound in Medicine and Biology*, 28(4):507-517.
Rabben, "An ultrasound-based method for determining pulse wave velocity in superficial arteries" 2004 *Journ. Of Biomechanics*, 37(10): 1615-1622.
Raghupathy, "Generalized Anisotropic Inverse Mechanics for Soft Tissues" Aug. 2010 *J. Biomech. Eng.*, 132(8):081006.
Revell, "Ultrasound Speckle Tracking for Strain Estimation," 2003 University of Bristol Department of Computer Science; Dec.: 4pgs.
Ribbers, "Noninvasive two-dimensional strain imaging of arteries: Validation in phantoms and preliminary experience in carotid arteries in vivo" 2007 *Ultrasound in Medicine and Biology*, 33(4):530-540.
Rihaczek, "Radar waveform selection—a simplified approach," Nov. 1971 *IEEE Trans. Aerosp. Electron. Syst.*, AES-7(6): 1078-1086.
Salomir, "Hyperthermia by MR-guided focuses ultrasound: Accurate temperature control based on fast MRI and a physical model of local energy deposition and heat conduction," 2000 *Magnetic Resonance in Medicine*,43:342-347.
Sanghvi et al., "Noninvasive surgery of prostate tissue by high-intensity focused ultrasound," Nov. 1996 IEEE *Trans. Ultrason., Ferroelectr., Freq. Contr.*, 43 (6): 1099-1110.
Sanghvi, "New developments in therapeutic ultrasound," Nov./Dec. 1996 *IEEE Eng. Med. Biol. Mag.*, 15(6):83-92.
Sapareto, "Thermal dose determination in cancer therapy," 1984 *Int. J. Rad. Onc. Biol. Phys.*, 10(6):787-800.
Schoenhagen, "Coronary imaging: Angiography shows the stenosis, but IVUS, CT, and MRI show the plaque" 2003 *Cleveland Clinic Journ. Of Medicine*, 70(8):713-719.
Seip, "Characterization of a Needle Hydrophone Array for Acoustic Feedback during Ultrasound Hyperthermia Treatments," *1992 Ultrasonics Symposium Proceedings*, 2:1265-1269.
Seip, "Non-Invasive Detection of Thermal Effects due to Highly Focused Ultrasonic Fields," 1993 *Ultrasonics Symposium Proceedings*, 2:1229-1232.
Seip, "Dynamic focusing in ultrasound hyperthermia treatments using implantable hydrophone arrays," Sep. 1994 IEEE *Trans. Ultrason., Ferroelectr., Freq. Control*, 41(5):706-713.
Seip, "Invasive and Non-Invasive Feedback for Ultrasound Phased Array Thermotherapy," 1994 *Ultrasonics Symposium Proceedings*, 3:1821-1824.
Seip, "Non-invasive Spatio-temporal Temperature Change Estimation Using Diagnostic Ultrasound," 1995 *Ultrasonics Symposium Proceedings*.

(56) References Cited

OTHER PUBLICATIONS

Seip, "Non-invasive estimation of tissue temperature response to heating fields using diagnostic ultrasound," 1995 *IEEE Trans. Biomed. Eng.*, 42(8):828-839.
Seip, "Noninvasive real-time multipoint temperature control for ultrasound phased array treatments," Nov. 1996 IEEE *Transactions on Ultrasonics Ferroelectrics and Frequency Control*, 43 (6): 1063-1073.
Seip, "High-intensity focused ultrasound (HIFU) phased arrays: Recent developments in transrectal transducers and driving electronics," 2003 *Proc. 3rd Int. Symp. Ther. Ultrasound*, 1:423-428.
Shen, "An optimal image operator design technique for coded excitation ultrasound imaging system," 1994 *Ultrasonics Symposium, Proceedings. IEEE*, 3:1777-1781.
Shen, "A Post-Beamforming Processing Technique for Enhancing Conventional Pulse-Echo Ultrasound Imaging Contrast Resolution," 1995 *IEEE Ultrasonics Symposium Proceedings*.
Shen, "On the design of a transversal filler bank for parallel processing multiple image lines in real-time acoustic imaging," in *Acoustics, Speech, and Signal Processing*, 1996. ICASSP—96. Conference Proceedings., IEEE International Conference, 6:3109-3112.
Shen, "Real-time 3d pulse-echo ultrasonic imaging with coded-excitation systems," in *Image Processing*, Oct. 1996. Proceedings. International Conference, 1:717-720.
Shen, "A new coded-excitation ultrasound imaging system—part I: basic principles," 1996 *IEEE Trans. Ultrason., Ferroelect., Freq. Conti:*, 43(1): 131-140.
Shen, "A New Coded-Excitation Ultrasound Imaging System—Part II: Operator Design," 1996 *IEEE Trans. Ultrason., Ferroelect., Freq. Conti:*, 43(1): 141-148.
Shen, "Filter-based coded-excitation system for high-speed ultrasonic imaging," Dec. 1998 *IEEE Tans. Med.* 17(6): 923-934.
Shung, "Scattering of ultrasound by blood" Nov. 1976 *IEEE Trans Biomed Eng.*, 23(6):460-7.
Simon, "Estimation of Mean Scatterer Spacing Based on Autoregressive Spectral Analysis of Prefiltered Echo Data," 1995 *Ultrasonics Symposium Proceedings*.
Simon, "Two-Dimensional Temperature Estimation Using Diagnostic Ultrasound" Jul. 1998 *IEEE Transactions on Ultrasonics, Ferroelectrics, and Frequency Control.*, 45(4): 1088-1099.
Simon, "Combined ultrasound image guidance and therapy using a therapeutic phased array," May 1998 *SPIE Med. Imag.*, 3341:89-98.
Smith, "Control system for an MRI compatible intracavitary ultrasound array for thermal treatment of prostate disease," May-Jun. 2001 *International Journal of Hyperthermia*, 17(3):271-282.
Souchon, "Monitoring the formation of thermal lesions with heat-induces echo-strain imaging: a feasibility study," 2005 *Ultrasound in Medicine and Biology*, 31:251-259.
Steidl, "Dual-mode ultrasound phased arrays for noninvasive surgery: Post-beamforming image compounding algorithms for enhanced visualization of thermal lesions," Jul. 2002 *Proc. IEEE Int. Symp. Biomed. Imag.*, 429-432.
Steinman, "Flow imaging and computing: large artery hemodynamics" Dec. 2005 *Annals Of Biomedical Engineering*, 33(12):1704-1709.
Sumi, "Fine elasticity imaging utilizing the iterative rf-echo phase matching method" 1999 *IEEE Trans. UFFC*, 46(1):158-166.
Sun, "Focusing of therapeutic ultrasound through a human skull: A numerical study," 1998 *J. Acoust. Soc. Amer.*, 104:1705-1715.
Sun, "Adaptive real-time closed-loop temperature control for ultrasound hyperthermia using magnetic resonance thermometry," Oct. 2005*Concepts in Magnetic Resonance Part B-Magnetic Resonance Engineering*, 27B(1):51-63.
Swillens, "Two dimensional flow imaging in the carotid bifurcation using a combined speckle tracking and phase-shift estimator: a study based on ultrasound simulations and in vivo analysis" 2010 *Ultrasound in Medicine and Biology*, 36(10):1722-1735.
Swillens, "Two-dimensional blood velocity estimation with ultrasound: speckle tracking versus crossed-beam vector Doppler based on flow simulations in a carotid bifurcation model" 2010 *IEEE Transactions on Ultrasonics Ferroelectrics and Frequency Control*, 57(2):327-339.
Tanter, "Focusing and steering through absorbing and aberrating layers: Application to ultrasonic propagation through the skull," 1998 *J. Acoust. Soc. Amer.*, 103:2403-2410.
Taylor, "Open problems in computational vascular biomechanics: Memodynamics and arterial wall mechanics" Sep. 2009 *Comput Methods Appl Mech Eng.*, 198(45-46): 3514-3523.
Tempany, "MR imaging-guided focuses ultrasound surgery of uterine leiomyomas: a feasibility study," Nov. 2003 *Radiology*, 226:897-905.
Thomenius, "Evolution of ultrasound beamformers," 1996 *IEEE Ultrason. Symp.*, 1615-1622.
Trahey, "Angle independent ultrasonic blood flow detection by frame-to-frame correlation of B-mode images," *Ultrasonics*, IPC Science and Technology Press Ltd., Guildford, GB, Sep. 1988; 26(5):271-276.
Tsou, "Role of ultrasonic shear rate estimation errors in assessing inflammatory response and vascular risk," Jun. 2008 *Ultrasound Med Biol.*, 34(6): 963-972.
Uchida, "Transrectal high-intensity focused ultrasound for the treatment of localized prostate cancer: Eightyear experience," Nov. 2009 *Int. J. Urology*, 16(11):881-886.
Vanbaren, "A new algorithm for dynamic focusing of phased-array hyperthermia applicators through tissue inhomogeneities," *IEEE Ultrasonics Symposium Proceedings*, 1993; 2:1221-1224.
Vanbaren, "Real-time Dynamic Focusing through Tissue Inhomogeneities during Hyperthermia Treatments with Phased Arrays," 1994 *Ultrasonics Symposium Proceedings*, 3:1815-1819.
Vanbaren, "2D Large Aperture Ultrasound Phased Arrays for Hyperthermia Cancer Therapy: Design, Fabrication, and Experimental Results," 1995 *Ultrasonics Symposium Proceedings*.
Vanbaren, "Multi-Point Temperature Control During Hyperthermia Treatments: Theory and Simulation," Aug. 1995 *IEEE Transactions on Biomedical Engineering*, 41(5):706-713.
Vanne et al., "MRI feedback temperature control for focused ultrasound surgery," 2003 *Physics in Medicine and Biology*, 48(1):31.
Varghese, "Direct strain estimation in elastography using spectral cross-correlation" 2000 *Ultrasound in Med. Biol.*, 26(9):1525-1537.
Wagner, "Fundamental correlation lengths of coherent speckle in medical ultrasonic images," Jan. 1988 IEEE *Tmns. Ultrason., Ferroelect., Freq. Comr.*, 35(1):34-44.
Wan, "Ultrasound surgery: Comparison of strategies using phased array systems," Nov. 1996 *IEEE Trans. UFFC*, 43(6):1085-1098.
Wan, "Imaging with concave large-aperture therapeutic ultrasound arrays using conventional synthetic-aperture beamforming," Aug. 2008 *IEEE Trans Ultrason Ferroelectr Freq Control*, 55(8):1705-18.
Wan, "A 2d post-beamforming filter for contrast restor ation in medical ultrasound: in vivo results," 2009 *Conf. Proc IEEE Eng Med Biol Soc*, 2009:1945-8.
Wan, "A Post-Beamforming 2-D Pseudoinverse Filter for Coarsely Sampled Ultrasound Arrays" Sep. 2009 *IEEE Trans Ultrason Ferroelectr Freq Control.*, 56(9):1888-1902.
Wan, "Imaging vascular mechanics using ultrasound: Phantom and in vivo results" Apr. 14-17, 2010, 7th IEEE International Symposium on Biomedical Imaging: From Nano to Macro, ISBI 2010, Rotterdam; Netherlands, Article No. 5490152, 980-983.
Wan, "Simultaneous imaging of tissue motion and flow velocity using 2D phase-coupled speckle tracking" 2010 Proceedings—IEEE Ultrasonics Symposium, 2010: 487-490.
Wang, "Effects of phase quantization errors on field patterns generated by an ultrasound phased array hyperthermia applicator," 1991 *IEEE Trans. Ultrasonics Ferroelec. Frequency Control*, 38(5): 521-531.
Wang, "Adaptive 2-D Cylindrical Section Phased Array System for Ultrasonic Hyperthermia," 1992 *Ultrasonics Symposium Proceedings*, 2:1261-1264.
Wang, "Phase aberration correction and motion compensation for ultrasonic hyperthermia phased arrays: Experimental results" 1994 *IEEE Trans. on Ultrason., Ferroelec., and Freq. Control*, 41(1):34-43.

(56) References Cited

OTHER PUBLICATIONS

Weitzel, "High-Resolution Ultrasound Elasticity Imaging to Evaluate Dialysis Fistula Stenosis" Jan. 2009 *Seminars III Dialysis*, 22(1):84-89.
Wu, "Time reversal of ultrasonic fields. II. Experimental results," *IEEE Trans. Ultrason., Ferroelectr., Freq. Control*, Sep. 1992; 39(5):567-578.
Wu, "Advanced hepatocellular carcinoma: Treatment with high-intensity focused ultrasound ablation combined with transcatheter arterial embolization," *Radiology*, May 2005; 235(2):659-667.
Wu, "Feasibility of US-guided high-intensity focused ultrasound treatment in patients with advanced pancreatic cancer: Initial experience," *Radiology*, Sep. 2005; 236(3):1034-1040.
Yao, "Enhanced lesion visualization in image-guided noninvasive surgery with ultrasound phased arrays," Oct. 2001 *Proc. 23rd Annu. Int. Conf. IEEE Eng, Med. Biol. Soc.*, 3:2492-2495.
Yao, "Real-time monitoring of the transients of HIFU-induced lesions," Oct. 2003 *Proc. IEEE Ultrason. Symp.*, 1:1006-1009.
Yao, "Dual-mode ultrasound phased arrays for imaging and therapy," Apr. 2004 *Proc. IEEE Int. Symp. Biomed. Imag.*, 1:25-28.
Yuh, "Delivery of systemic chemotherapeutic agent to tumors by using focused ultrasound: Study in a murine model," Feb. 2005; *Radiology*, 234(2):431-437.
Aldiabat, "Real-Time Image-Based Transcranial Refocusing of Dual-Mode Ultrasound Arrays" Dissertation, Jan. 2019, 161 pages.
Alonso, "Focal delivery of AAV2/1-transgenes into the rat brain by localized ultrasound-induced Bbb opening" 2013 *Mol Ther Nucleic Acids*, 2:e73.
Arvanitis, "Combined ultrasound and mr imag-ing to guide focused ultrasound therapies in the brain" Jul. 2013 *Phys Med Biol*, 58(14):4749-4761.
Aryal, "Multiple treatments with liposomal doxorubicin and ultrasound-induced disruption of blood-tumor and blood-brain barriers improve outcomes in a rat glioma model" Jul. 2013 *J Control Release*, 169(1-2):103-111.
Aubry, "Experimental demonstration of noninvasive transskull adaptive focusing based on prior computed tomography scans" 2013 *The Journal of the Acoustical Society of America*, 113(1):84-93.
Baek, "A review of low-intensity focused ultrasound for neuromodulation" 2017 *Biomed. Eng. Lett.* 7:135-142.
Baker, "A review of therapeutic ultrasound: biophysical effects" 2001 *Phys. Ther.* 81, 1351-1358.
Bakker, "The scalable brain atlas: Instant web-based access to public brain atlases and related content" 2015 Neuroinformatics, 13(3):353-366.
Ballard, "Dual-mode ultrasound arrays for image-guided targeting of atheromatous plaques" in *AIP Conference Proceedings* 1503, 124-128 (AIP, 2012).
Barber, "The density of tissues in and about the head" 1970 *Acta neurologica scandinavica*, 46(1):85-92.
Barnard, "Small localized ultrasonic lesions in the white and gray matter of the cat brain" 1956 *AMA Archives of Neurology & Psychiatry*, 75(1): 15-35.
Bayat, "Adaptive motion compensation for in vivo ultrasound temperature estimation" in Ultrasonics Symposium (IUS), 2013 IEEE International, pp. 1797-1800.
Bayat, "Ultrasound thermography in vivo: A new model for calculation of temperature change in the presence of temperature heterogeneity" in *2013 IEEE International Ultrasonics Symposium (IUS)*, pp. 116-119 (ieeexplore.ieee.org, 2013).
Botros, "A Hybrid Computational Model for Ultrasound Phased-Array Heating in Presence of Strongly Scattering Obstacles" Nov. 1997 IEEE Trans Biomed Eng., 44(11): 1039-1050.
Burgess, "Targeted delivery of neural stem cells to the brain using mri-guided focused ultrasound to disrupt the blood-brain barrier" 2011 *PLoS One*, 6(11):e27877.
Byrne, "Epidural cylinder electrodes for presurgical evaluation of intractable epilepsy: technical note" Aug. 2008 Surg Neurol., 70(2):160-4; discussion 164. doi: 10.1016/j.surneu.2007.04.024. Epub Feb. 8, 2008.
Bystristsky, A review of low-intensity transcranial focused ultrasound for clinical applica-tions. *Curr Behav Neurosci*, 2:60-66, 2015.
Bystritsky, A review of low-intensity focused ultrasound pulsation. *Brain Stimul*, 4(3):125-136, Jul. 2011.
Casper, "Real-time implementation of a dual-mode ultrasound array system: In vivo results" 2013 IEEE Transactions on Biomedical Engineering, 60(10):2751-2759.
Chan, "Laser-generated focused ultrasound for arbitrary waveforms" 2016 *Appl. Phys. Lett.*, 109:174102.
Chang, "Unilateral magnetic resonance guided focused ultrasound thalamotomy for essential tremor: practices and clinicoradiological outcomes" 2015 *J Neurol Neurosurg Psychiatry*, 86(3):257-264.
Chu, "Neuromodulation Accompanying Focused Ultrasound-Induced Blood-Brain Barrier Opening" Oct. 2015 *Scientific Reports* 5:15477; 12 pages.
Clement, "A noninvasive method for focusing ultrasound through the human skull" 2002 *Phys Med Biol.*, 47: 1219-1236.
Coluccia, "First noninvasive thermal ablation of a brain tumor with MR-guided focused ultrasound," 2014, *J Ther Ultrasound*, 2:17.
Constans, "A 200-1380-kHz Quadrifrequency Focused Ultrasound Transducer for Neurostimulation in Rodents and Primates: Transcranial In Vitro Calibration and Numerical Study of the Influence of Skull Cavity" 2017 *IEEE Trans Ultrason Ferroelectr Freq Control.*, 64(4):717-724. doi: 10.1109/TUFFC.2017.2651648. Epub Jan. 11, 2017.
Corl, "A real-time synthetic-aperture imaging system" in Acoustical Imaging vol. 9 Visualization and Characterization, 1980, Plenum Press. Cover page, copyright page and pp. 341-355.
Dallapiazza, "Noninvasive neuromodulation and thalamic mapping with low-intensity focused ultrasound" Apr. 2017, *J Neurosurg.*, 1-10. doi: 10.3171/2016.11.JNS16976. [Epub ahead of print].
Daniels, "Focused Ultrasound-Induced Suppression of Auditory Evoked Potentials in Vivo" 2018 *Ultrasound Med. Biol.* 44, 1022-1030.
Darrow, "Reversible neuroinhibition by focused ultrasound is mediated by a thermal mechanism" Nov.-Dec. 2019 *Brain Stimul.*, 12(6): 1439-1447. doi: 10.1016/j.brs.2019.07.015. Epub Jul. 23, 2019. Prepublication.
Darrow, "Transcranial Focused Dual-Mode Ultrasound for Noninvasive Neuromodulation" presentation Sep. 30, 2018, Minnesota Neurological Society meeting; 34 pages.
Darvas, "Toward Deep Brain Monitoring with Superficial EEG Sensors Plus Neuromodulatory Focused Ultrasound" Aug. 2016, *Ultrasound Med Biol.*, 42(8):1834-47. doi: 10.1016/j.ultrasmedbio. 2016.02.020. Epub May 13, 2016.
Deffieux, "Low-intensity focused ultrasound modulates monkey visuomotor behavior" 2013 *Current Biology*, 23(23):2430-2433.
Deng, "Targeted drug delivery across the blood-brain barrier using ultrasound technique" Dec. 2010 *Ther Deliv*, 1(6):819-848.
Dumas, "Piezocomposite technology an innovative approach to the improvement of ndt performance using ultrasounds" in 8th European Conference on Non Destructive Testing, Jun. 2002, Barcelona, Spain; 2 pages.
Ebbini, "Guest Editorial to the Special Issue on Therapeutic Ultrasound: Trends at the Leading-Edge," *IEEE Transactions on Biomedical Engineering*, Jan. 2010; 57(1):5-6.
Ebbini, "Real-time ultrasound thermography and thermometry [life sciences]" Mar. 2018 IEEE Signal Processing Magazine, 35:166-174.
Elias, "A randomized trial of focused ultrasound thalamotomy for essential tremor" Aug. 2016, *New England Journal of Medicine*, 375(8):730-9.
European Search Report and Search Opinion for European Patent Application No. 18193572.7, dated Sep. 2, 2019, 15 pages.
Fisher, "Low-intensity focused ultrasound alters the latency and spatial patterns of sensory-evoked cortical responses in vivo" 2018 *J. Neural Eng.* 15, 035004.
Fry, "Ultrasonic lesions in the mammalian central nervous system" 1955, *Science*, 122(3168):517-518.
Fry, "Acoustical properties of the human skull" 1978 *The Journal of the Acoustical Society of America*, 63(5):1576-1590.

(56) References Cited

OTHER PUBLICATIONS

Fry, "Fundamental neurological research and human neurosurgery using intense ultrasound" 1960 *IRE transactions on medical electronics*, 3:166-181.
Fry, "Further studies of the transkull transmission of an intense focused ultrasonic beam: lesion production at 500 khz" 1980 *Ultrasound Med Biol*, 6(1):33-38.
Fry, "Production of focal destructive lesions in the central nervous system with ultrasound" 1954 *Journal of neurosurgery*, 11(5):471-478.
Fry, "Production of reversible changes in the central nervous system by ultrasound" 1958 *Science*, 127(3289):83-84.
Fry, "Transkull transmission of an intense focused ultrasonic beam" 1977 *Ultrasound in Medicine and Biology*, 3(2):183-184.
Fry, "Transkull focal lesions in cat brain produced by ultrasound" May 1981 *J Neurosurg*, 54(5):659-663.
Golemati, "Carotid artery wall motion estimated from b-mode ultrasound using region tracking and block matching" 2003 *Ultrasound in Med& Biol.*, 29(3):387-399.
Goodman, "*Introduction to Fourier Optics*" 2005, Roberts & Company, Greenwood Village, Colorado. Cover page, publisher page, table of contents.
Gulick, "Comparison of Electrical and Ultrasound Neurostimulation in Rat Motor Cortex" 2017 *Ultrasound Med. Biol.*, 43:2824-2833.
Gulick, "Effect of Ultrasound Stimulation on Excised Brain Tissue Impedance" 2013 *IEEE Neural Engineering Short Papers No. 0669*; 1 page.
Guo, "Ultrasound Produces Extensive Brain Activation via a Cochlear Pathway" 2018 *Neuron* 98:1020-1030.e4.
Hakimova, "Ultrasound stimulation inhibits recurrent seizures and improves behavioral outcome in an experimental model of mesial temporal lobe epilepsy" Aug. 2015 *Epilepsy Behav*, 49:26-32.
Hall, "Phantom materials for elastography" 1997 *IEEE transactions on ultrasonics, ferroelectrics, and frequency control*, 44(6):1355-1365.
Hameroff, "Transcranial ultrasound (TUS) effects on mental states: a pilot study" May 2013 *Brain Stimul.*, 6(3):409-15. doi: 10.1016/j.brs.2012.05.002. Epub May 29, 2012.
Haritonova, "In vivo application and localization of transcranial focused ultrasound using dual-mode ultrasound arrays" 2015 *IEEE transactions on ultrasonics, ferroelectrics, and frequency control*, 62(12):2031-2042.
Hynynen, "Demonstration of potential noninvasive ultrasound brain therapy through an intact skull" 1998 *Ultrasound in medicine & biology*, 24(2):275-283.
Hynynen, "MR imaging-guided focused ultrasound surgery of fibroadenomas in the breast: a feasibility study" 2001 *Radiology*, 219(1):176-185.
Hynynen, "Noninvasive MR imaging-guided focal opening of the blood-brain barrier in rabbits" Sep. 2001 *Radiology*, 220(3):640-646.
Hynynen, "Pre-clinical testing of a phased array ultrasound system for mri-guided noninvasive surgery of the braina primate study" 2006 *European journal of radiology*, 59(2):149-156.
Hynynen, "Ultrasound for drug and gene delivery to the brain" Jun. 2008 *Adv Drug Deliv Rev*, 60(10):1209-1217.
Hynynen, "500-element ultrasound phased array system for noninvasive focal surgery of the brain: a preliminary rabbit study with ex vivo human skulls" 2004 *Magn. Reson. Med.*, 52:100-107.
Hyungmin, "Estimation of the spatial profile of neuromodulation and the temporal latency in motor responses induced by focused ultrasound brain stimulation" May 2014 *Neuroreport*, 25(7):475-479.
International Written Opinion/International Preliminary Report on Patentability, dated Jul. 15, 2009 for International Patent Application No. PCT/US2008/007842, 25 pgs.
International Preliminary Report on Patentability dated Oct. 15, 2013 for International Patent Application No. PCT/US2012/033584, 12 pgs.
International Preliminary Report on Patentability dated Dec. 10, 2012 for International Patent Application No. PCT/US2011/039837, 6 pgs.
International Search Report dated Jun. 13, 2013 for International Patent Application No. PCT/US2012/033584, 6 pgs.
International Search Report dated Jan. 20, 2012 for International Patent Application No. PCT/US2011/039837, 4 pgs.
Jedrzejewicz, "Two-way continuous transmit and receive focusing in ultrasound imaging" 2013 ZONARE Medical Systems, Inc., Tech. Rep., [Online]. Available: http://res.mindray.com/Documents/2016-12-14/d2dd8ebd-a052-482a-8541-b8de227d4ee6/K90127_two_way_transmit_receive.pdf.
Jensen, "Calculation of pressure fields from arbitrarily shaped, apodized, and excited ultrasound transducers" 1992 *IEEE transactions on ultrasonics, ferroelectrics, and frequency control*, 39(2):262-267.
Jensen, "Synthetic aperture ultrasound imaging" 2006 *Ultrasonics*, 44:e5-e15.
Jones, "Comparison of analytical and numerical approaches for ct-based aberration correction in transcranial passive acoustic imaging" 2015 *Physics in Medicine & Biology*, 61(1): 23.
Jossinet, "Impedance Modulation by Pulsed Ultrasound" 1999 *Annals of the New York Academy of Sciences* 873 (1 Electrical BI):396-407.
Kamimura, "Focused ultrasound neuromodulation of cortical and subcortical brain structures using 1.9 MHz" 2016 *Med. Phys.* 43, 5730.
Khanna, "Intracranial Applications of MR Imaging—Guided Focused Ultrasound" 2017 *AJNR Am. I Neuroradiol.* doi:10.3174/ajnr.A4902, 426-431.
Khraiche, "Ultrasound induced increase in excitability of single neurons" 2008 *Conf Proc IEEE Eng Med Biol Soc.* 2008:4246-9. doi: 10.1109/IEMBS.2008.4650147.
Kim, "Estimation of the spatial profile of neuromodulation and the temporal latency in motor responses induced by focused ultrasound brain stimulation" 2014 *Neuroreport*, 25(7):475.
Kim "Focused ultrasound-mediated non-invasive brain stimulation: examination of sonication parameters" 2014 *Brain Stimul.*, 7(5):748-56. doi: 10.1016/j.brs.2014.06.011. Epub Jul. 2, 2014.
Kim, "Noninvasive transcranial stimulation of rat abducens nerve by focused ultrasound" *Ultrasound in medicine & biology*, 38, No. 9, pp. 1568-1575, 2012.
Kim, "Suppression of EEG visual-evoked potentials in rats through neuromodulatory focused ultrasound" 2015 *Neuroreport* 26:211-215.
King, "Effective parameters for ultrasound-induced in vivo neurostimulation" *Ultrasound in medicine & biology*, 39, No. 2, pp. 312-331, 2013.
King, "Localization of ultrasound induced in vivo neurostimulation in the mouse model" *Ultrasound in medicine & biology*, 40, No. 7, pp. 1512-1522, 2014.
Kinoshita, "Noninvasive localized delivery of herceptin to the mouse brain by mri-guided focused ultrasound-induced blood-brain barrier disruption" *Proceedings of the National Academy of Sciences*, 2006, 103(31):11719-11723.
Konofagou, "Optimization of the ultrasound-induced blood-brain barrier opening" 2012 *Theranostics*, 2(12):1223-1237.
Krishna, "Prospective Tractography-Based Targeting for Improved Safety of Focused Ultrasound Thalamotomy" 2018 *Neurosurgery*. doi:10.1093/neuros/nyy020.
Kyriakou, "A review of numerical and experimental compensation techniques for skull-induced phase aberrations in transcranial focused ultrasound" 2014 *Int. J. Hyperthermia* 30:36-46.
Lalonde, "Field conjugate acoustic lenses for ultrasound hyperthermia" Sep. 1993 *IEEE Transactions on Ultrasonics, Ferroelectrics, and Frequency Control*, 40(5):592-602.
Lalonde, "Variable frequency field conjugate lenses for ultrasound hyperthermia" Sep. 1995 *IEEE Transactions on Ultrasonics, Ferroelectrics, and Frequency Control*, 42(5):825-831.
Legon, "Neuromodulation with single-element transcranial focused ultrasound in human thalamus" 2018 *Hum. Brain Mapp.* 39, 1995-2006.

(56) References Cited

OTHER PUBLICATIONS

Legon, "Transcranial focused ultrasound modulates the activity of primary somatosensory cortex in humans" 2014 *Nature Neurosci.*, 17(2): 322-329.
Legon, "Transcranial focused ultrasound neuromodulation of the human primary motor cortex" 2018 *Sci. Rep.* 8:10007.
Lele, "The thermal hypothesis of the mechanism of ultrasonic focal destruction in organized tissues" Interaction of ultrasound and biological tissues. FDA, pp. 73-8008, 1972.
Lipsman, "MR-guided focused ultrasound thalamotomy for essential tremor: a proof-of-concept study" 2013 *The Lancet Neurology*, 12(5):462-468.
Liu, "Adaptive lesion formation using dual mode ultrasound array system" 2017 *AIP Conf. Proc.* 1821, 060003.
Liu, "In vivo mr quantification of superparamagnetic iron oxide nanoparticle leakage during low-frequency-ultrasound-induced blood-brain barrier opening in swine" Dec. 2011 *J Magn Reson Imaging*, 34(6): 1313-1324.
Liu, "Magnetic resonance monitoring of focused ultrasound/magnetic nanoparticle targeting delivery of therapeutic agents to the brain" Aug. 2010 *Proc Natl Acad Sci U S A*, 107(34):15205-15210.
Liu, "Three-dimensional image guidance for transcranial focused ultrasound therapy" Apr. 2017 IEEE 14th International Symposium on Biomedical Imaging (ISBI 2017), 916-919.
Lockwood, "High-speed method for computing the exact solution for the pressure variations in the near field of a baffled piston" *The Journal of the Acoustical Society of America*, 53, No. 3, pp. 735-741:1973.
Lynn, "Histology of cerebral lesions produced by focused ultrasound" 1944 *The American journal of pathology*, 20(3):637.
Maimbourg, "3d printed adaptive acoustic lens as a disruptive technology for transcranial ultrasound therapy using single-element transducers" 2018 *Physics in Medicine & Biology*, 63(2):025026.
Manlapaz, "Effects of ultrasonic radiation in experimental focal epilepsy in the cat" 1964 *Experimental neurology*, 10(4):345-356.
Marquet, "Non-invasive transcranial ultrasound therapy based on a 3d ct scan: protocol validation and in vitro results" May 2009 *Phys Med Biol*, 54(9):2597-2613.
Martin, "High intensity focused ultrasound for noninvasive functional neurosurgery" 2009 *Annals of Neurology: Official Journal of the American Neurological Association and the Child Neurology Society*, 66(6):858-861.
Marty, "Dynamic study of blood-brain barrier closure after its disruption using ultrasound: a quantitative analysis" Oct. 2012 *J Cereb Blood Flow Metab*, 32(10):1948-1958.
McDannold, "Transcranial magnetic resonance imaging-guided focused ultrasound surgery of brain tumors: initial findings in 3 patients" *Neurosurgery*, 66, No. 2, 323-332, 2010.
McGough, "Rapid calculations of time-harmonic nearfield pressures produced by rectangular pistons" *The Journal of the Acoustical Society of America*, 115, No. 5, pp. 1934-1941, 2004.
Mehic, "Increased anatomical specificity of neuromodulation via modulated focused ultrasound" 2014 *PLoS One*, 9(2):e86939.
Meyers, "Early experiences with ultrasonic irradiation of the pallidofugal and nigral complexes in hyperkinetic and hypertonic disorders" Jan. 1959 *J Neurosurg*, 16(1):32-54.
Min, "Focused ultrasound-mediated suppression of chemically-induced acute epileptic EEG activity" 2011 *BMC Neurosci.*, 12:23.
Mucci, "A comparison of efficient beamforming algorithms" 1984 *IEEE Transactions on Acoustics, Speech, and Signal Processing*, 32(3):548-558.
Mueller, "Transcranial Focused Ultrasound Modulates Intrinsic and Evoked EEG Dynamics" 2014 *Brain Stimul.*, 7:900-908.
Naor, "Ultrasonic neuromodulation" 2016 *J. Neural Eng.*, 13:031003.
Ocheltree, "Sound field calculation for rectangular sources" 1989 *IEEE transactions on ultrasonics, ferroelectrics, and frequency control*, 36(2):242-248.
Oppenheim et al., Discrete-time signal processing, Second Edition. Prentice-Hall, Upper Saddle River, New Jersey, 1999; 896 pages.

Patel, "Hard real-time closed-loop electrophysiology with the Real-Time eXperiment Interface (RTXI)" 2017 *PLoS Comput. Biol.*, 13:e1005430.
Paxinos, "*The mouse brain in sterotaxic coordinates*" 2004 Gulf Professional Publishing. Cover page, publisher page, table of contents.
Pinton, "Direct phase projection and transcranial focusing of ultrasound for brain therapy" 2012 *IEEE Trans Ultrason Ferroelectr Freq Control*, 59(6): 1149-59.
Podgorski, "Brain heating induced by near-infrared lasers during multiphoton microscopy" 2016 *J. Neurophysiol.* 116:1012-1023.
Prada, "Decomposition of the time reversal operator: Detection and selective focusing on two scatterers" 1996 *The Journal of the Acoustical Society of America*, 99(4):2067-2076.
Raymond, "Ultrasound enhanced delivery of molecular imaging and therapeutic agents in Alzheimer's disease mouse models" 2008 *PLoS One*, 3(5):e2175.
Rezayat, "A Review on Brain Stimulation Using Low Intensity Focused Ultrasound" 2016 *Basic and Clinical Neuroscience*, 7 (3):187-94.
Rieke, "MR thermometry" 2008 *Journal of Magnetic Resonance Imaging: An Official Journal of the International Society for Magnetic Resonance in Medicine*, 27(2):376-390.
Rohani, "Focused ultrasound for essential tremor: review of the evidence and discussion of current hurdles" *Tremor and Other Hyper-kinetic Movements*, 2017; 7. doi: 10.7916/D8Z89JN1.
Sakatani, "Somatosensory evoked potentials in rat cerebral cortex before and after middle cerebral artery occlusion" 1990 *Stroke* 21:124-132.
Salomir, "Image-based control of the magnetic resonance imaging guided focused ultrasound thermotherapy" 2006 *Topics in Magnetic Resonance Imaging*, 17(3): 139-151.
Sato, "Ultrasonic Neuromodulation Causes Widespread Cortical Activation via an Indirect Auditory Mechanism" 2018 *Neuron* 98:1031-1041.e5.
Savitzky, "Smoothing and differentiation of data by simplified least squares procedures." *Analytical chemistry*, 36, No. 8, pp. 1627-1639, 1964.
Sawyer, "Nanoparticle-based evaluation of blood-brain barrier leakage during the foreign body response" *Journal of Neural Engineering*, 10(2013) 016013; 10 pages.
Schiefer, "Moving forward: Advances in the treatment of movement disorders with deep brain stimulation" 2011 *Frontiers in Integrative Neuroscience*, 5:69.
Shapoori, "An ultrasonic-adaptive beamforming method and its application for trans-skull imaging of certain types of head injuries; part i: Transmission mode" *IEEE Transactions on Biomedical Engineering*, 2015, 62(5):1253-1264.
Shehata, "Feasibility of targeting atherosclerotic plaques by high-intensity-focused ultrasound: an in vivo study" Dec. 2013 *J Vasc Interv Radiol*, 24(12):1880-1887.e2.
Souchon, "Ultrasonic elastography using sector scan imaging and a radial compression" 2002 *Ultrasonics*, 40(1-8):867-871.
Szabo, "Diagnostic ultrasound imaging: inside out," Elsevier Academic Press, Burlington, Massachusetts, 2004. Title page, copyright page, and table of contents, 12 pages total.
Tanaka, "Active circulators —the realization of circulators using transistors" 1965 *Proceedings of the IEEE*, 53:260-267.
Ter Haar, "Therapeutic applications of ultrasound" 2007 *Prog. Biophys. Mol. Biol.*, 93:111-129.
Thomenius, "Recent Trends in Ultrasound Beamformation" Sep. 2005 IEEE Ultrasonics Symposium, Rotterdam, The Netherlands, 113 pages.
Treat, "Improved anti-tumor effect of liposomal doxorubicin after targeted blood-brain barrier disruption by MRI-guided focused ultrasound in rat glioma" Oct. 2012 *Ultrasound Med Biol*, 38(10):1716-1725.
Treat, "Targeted delivery of doxorubicin to the rat brain at therapeutic levels using mri-guided focused ultrasound" Aug. 2007 *Int J Cancer*, 121(4):901-907.
Tufail, "Transcranial pulsed ultrasound stimulates intact brain circuits" 2010 *Neuron* 66:681-694.

(56) References Cited

OTHER PUBLICATIONS

Tufail, "Ultrasonic neuromodulation by brain stimulation with transcranial ultrasound" Sep. 2011 *Nat Protoc*, 6(9):1453-1470.
Tung, "The mechanism of interaction between focused ultrasound and microbubbles in blood-brain barrier opening in mice" Nov. 2011 *J Acoust Soc Am*, 130(5):3059-3067.
Tutwiler, "Ultrasonic beamforming architectures" in Medical Imaging 1998: Ultrasonic Transducer Engineering, 3341, pp. 43-55, *International Society for Optics and Photonics*, 1998.
Tyler, "Noninvasive neuromodulation with ultrasound? A continuum mechanics hypothesis" Feb. 2011 *Neuroscientist*, 17(1):25-36.
Tyler, "Remote excitation of neuronal circuits using low-intensity, low-frequency ultrasound" Oct. 2008 *PLoS One*, 3(10):e3511. doi: 10.1371/journal.pone.0003511. Epub Oct. 29, 2008.
Vyas, "Extension of the angular spectrum method to calculate pressure from a spherically curved acoustic source" Nov. 2011 *J Acoust Soc Am.*, 130:2687-93.
Weintraub, "The emerging role of transcranial magnetic resonance imaging-guided focused ultrasound in functional neurosurgery" 2016 *Movement Disorders*, 32(1):20-27.
White, "Effect of the skull in degrading the display of echoencephalographic b and c scans" *The Journal of the Acoustical Society of America*, 44, No. 5, pp. 1339-1345, 1968.
White, "The deformation of the ultrasonic field in passage across the living and cadaver head" *Medical and biological engineering*, 7, No. 6, pp. 607-618, 1969.
White, "Transcranial ultrasound focus reconstruction with phase and amplitude correction" 2005 *IEEE Trans. Ultrason. Ferroelectr. Freq. Control*, 52:1518-1522.
Wright, "Ultrasonic stimulation of peripheral nervous tissue: an investigation into mechanisms" 2015 *J. Phys. Conf. Ser.*, 581:012003.
Wulff, "Effects of ultrasonic vibrations on nerve tissues." *Proceedings of the Society for Experimental Biology and Medicine*, 1951, 76(2):361-366.
Yang, "Neuromodulation of sensory networks in monkey brain by focused ultrasound with MRI guidance and detection" 2018 *Sci. Rep.* 8:7993.
Yang, "Transcranial Ultrasound Stimulation: A Possible Therapeutic Approach to Epilepsy" 2011 *Medical Hypotheses* 76(3):381-83.
Ye, "Frequency Dependence of Ultrasound Neurostimulation in the Mouse Brain" 2016 *Ultrasound Med Biol.*, 42(7):1512-30.
Yin, "A numerical study of transcranial focused ultrasound beam propagation at low frequency" Apr. 2005 *Phys Med Biol*, 50(8): 1821-1836.
Yoo, "Focused ultrasound modulates region-specific brain activity" 2011 *NeuroImage*, 56:1267-1275.
Yoshino, "Effects of focused ultrasound sonodynamic treatment on the rat blood-brain barrier" Mar. 2009 *Anticancer Res*, 29(3):889-895.
Younan, "Influence of the pressure field distribution in transcranial ultrasonic neurostimulation" Aug. 2013 *Med Phys*, 40(8):082902.
Zhang, "Defining the optimal age for focal lesioning in a rat model of transcranial hifu" Feb. 2015 *Ultrasound Med Biol*, 41(2):449-455.
European Search Report dated Jul. 27, 2020 for European Patent Application No. 20176810.8, 8 pages.
English translation of Office Action for Chinese Patent Application No. 201810722985.7, dated Nov. 24, 2020, 15 pages.

\* cited by examiner

Fig. 5

Algorithm 1 Optimal Synthesis of Multiple-focus, Multiple-frequency Transmit-receive Patterns Element waveforms $u_n(t) = 0 \quad \triangle \quad N$ number of elements
Wall CPs $\to H_W(f)$      $\triangle$ Size $M_W \times N$
Lumen CPs $\to H_L(f)$      $\triangle$ Size $M_L \times N$
Critical CPs $\to H_C(f)$      $\triangle$ Size $M_C \times N$ 1: for all $i = 1, \ldots, N_F$ do
2:    procedure SOLVE OPTIMIZATION PROBLEM $(H_W(f_i), H_L(f_i), H_C(f_i) \, u_{opt}(f_i))$
3:        $H_T = \begin{bmatrix} H_W \\ H_L \end{bmatrix}$    *and*    $H_C = H_C$
4:        $W_T = H_T^H H_T, \; W_C = (H_C^H H_C + \gamma_C I), \; \gamma_C > 0$ (small)
5:        Lagrange MNLS:
$$u_{opt}^{(i)} = W_C^{-1} H_T^H \left( H_T W_C^{-1} H_T^H \right)^\dagger p_T$$

Or Generalized Eigenvalue:

Choose $u_{opt}$ such that $\lambda_{max}(W_T, W_C) = \sup\limits_{u \neq 0} \dfrac{u^H W_T u}{u^H W_C u}$ Solution through Generalized Eigenvalue Decomposition
$$\lambda_{max} = \max \{\lambda_i | \det(\lambda W_C - W_T) = 0\}$$

Other optimization criteria can be applied, e.g. constant modulus or weighted solutions. These solutions can be generated separately or in parallel.

6:    end procedure
7:    for all $N$ DMUA elements $n = 1, 2, \ldots, N$ do
$$u_n(t) = u_n(t) + \Re\left\{ u^*_{opt_n}(f_i) e^{j2\pi f_i t} g(t) \right\} \quad \triangle \; g(t), \text{ e.g. raised cosine}$$
8:    end for
9: end for

ULTRASOUND IMAGE FORMATION AND/OR RECONSTRUCTION USING MULTIPLE FREQUENCY WAVEFORMS

CROSS-REFERENCE TO RELATED APPLICATION

This application is the § 371 U.S. National Stage of International Application No. PCT/US2014/047430, filed 21 Jul. 2014, which claims the benefit of U.S. Provisional Patent Application Ser. No. 61/857,442, filed Jul. 23, 2013, which are incorporated herein by reference.

BACKGROUND

The disclosure herein relates generally to ultrasound imaging. More particularly, the disclosure herein pertains to ultrasound imaging methods and systems for use in, e.g., diagnostic and/or therapy applications (e.g., imaging of complex media, such as blood vessels and/or regions proximate thereto, disc tissues, brain structures, etc.).

Ultrasound imaging is gaining increased attention not only as a way to detect cardiovascular diseases, but also for the evaluation of response to new anti-atherosclerotic therapies (see, Ainsworth, et al., "3D ultrasound measurement of change in carotid plaque volume—A tool for rapid evaluation of new therapies," *Stroke*, vol. 36, no. 9, pp. 1904-1909, September 2005), Intravascular ultrasound (IVUS) has been shown to provide an effective tool in measuring the progression or regression of atherosclerotic disease in response to therapies. However, IVUS is invasive, potentially risky, and more expensive than noninvasive imaging with ultrasound.

Advanced imaging modes on ultrasound scanners have led to increased interest in imaging important quantities, such as, wall shear rate (WSR) using Doppler (see, Blake, et al., "A method to estimate wall shear rate with a clinical ultrasound scanner," *Ultrasound in Medicine and Biology*, vol. 34, no. 5, pp. 760-764, May 2008) and tissue/wall motion (see, Tsou et al., "Role of ultrasonic shear rate estimation errors in assessing inflammatory response and vascular risk," *Ultrasound in Medicine and Biology*, vol. 34, no. 6, pp. 963-972, June 2008; Karimi et al., "Estimation of Nonlinear Mechanical Properties of Vascular Tissues via Elastography," *Cardiovascular Engineering*, vol. 8, no, 4, pp. 191-202, December 2008; and Weitzel et al., "High-Resolution Ultrasound Elasticity Imaging to Evaluate Dialysis Fistula Stenosis," *Seminars In Dialysis*, vol. 22, no. 1, pp. 84-89, January-February 2009) using speckle tracking.

Recently, there has been increased interest in imaging flow in conjunction with computational fluid dynamic (CFD) modeling for evaluation of large artery hemodynamics (see, Steimnan et al., "Flow imaging and computing: Large artery hemodynamics,"*ANNALS OF BIOMEDICAL ENGINEERING*, vol. 33, no. 12, pp. 1704-1709, December 2005; Figueroa, et al., "A computational framework for fluid-solid-growth modeling in cardiovascular simulations," *Computer Methods in Applied Mechanics and Engineering*, vol. 198, no. 45-46, pp. 3583-3602, 2009; and Taylor et al., "Open problems in computational vascular biomechanics: Hemodynamics and arterial wall mechanics," *Computer Methods in Applied Mechanics and Engineering*, vol. 198, no. 45-46, pp. 3514-3523, 2009). In this context, modeling fluid-solid interfaces has been defined as a challenge area in vascular mechanics.

The advent of piezo-composite transducer technology has allowed for the design and fabrication of effective dual-mode ultrasound arrays (DMUAs) for use in an ultrasound system capable of both image formation and generation of therapeutic high-intensity focused ultrasound (HIFU) beams. Such DMUAs have been used for pulse echo imaging. For example, traditional beamforming-based pulse echo image formation has been used in both analog and digital forms, which has led to improvement in image quality (e.g., such as with use of dynamic-beamforming available on many commercial scanners in the formation of ultrasound images). Further, for example, synthetic-aperture imaging and other more computationally based approaches have also been described and/or used (e.g., the Verasonics engine which is a software-based image formation tool and/or model).

However, to be able to noninvasively identify and treat target regions, improved ultrasound image formation is needed. Further, image reconstruction approaches to provide reconstructed images representative of one or more properties of the structure in the target regions (e.g., scattering function, speed of sound, attenuation, reflection coefficients, etc.). The reconstruction of these quantities reveals important features in the tissue architecture (e.g. healthy versus diseased vessel walls, extent of tissue change due to therapy, etc.) that cannot be obtained from conventional image formation.

SUMMARY

At least one embodiment of this disclosure relates to ultrasound image formation of a region of interest (e.g., a target region, such as a region including perivascular tissue). For example, in one or more embodiments of this disclosure, an ultrasound imaging architecture including a programmable transmit-receive chain allows for the application of transmit waveform design, together with pre- and post-beamforming filtering to achieve optimal image reconstruction of the scattering function in the target volume or region of interest (ROI). Such ultrasound imaging may make use of transmit waveform synthesis (or, more generally, wavefront synthesis) and post-beamforming filtering in the form of matched filtering or regularized inverse filtering. The performance of the system may be improved in one or more ways by coupling the waveform design and the pre- and post-beamforming filtering for detection, estimation, and high (super)-resolution image reconstruction. For example, mathematical operators described herein may allow for real-time implementation of enhancements to ultrasound imaging without requiring an excessive level of investment in transducer technology or hardware. For example, applications that require thousands of array elements with conventional beamforming may be achieved by reconstructive imaging and coded-wavefront design using arrays with a fraction of the channel count needed for the conventional case. One or more embodiments herein may allow for the use of the Fourier transform (FT) and, in particular, the discrete version of this the transform, the discrete Fourier transform (DFT), to simplify the imaging model and provide a computationally-efficient model for image reconstruction. In one or more embodiments, the use of a sliding eigenvalue (singular) decomposition of the ultrasound echo data at discrete frequencies makes it possible to derive imaging/ reconstruction operators with high specificity to echo components resulting from the use of specifically-designed codes and/or from an assumed scattering structure. This approach may be beneficial in rejecting reverberations and beamforming artifacts without compromising spatial resolutions.

In one or more embodiments, a randomly distributed discrete set of frequencies is employed to adaptively design a coding scheme which is "matched to the spectral characteristics of the target region" while "utilizing the maximum bandwidth of the transducer system for optimal spatial and contrast resolutions." For example, such adaptive ultrasound may provide the ability to perform imaging and therapy in complex media, which is in many cases hampered by the use of conventional continuous wave (CW) or pulsed excitations on the therapy and imaging sides of the system. In one or more embodiments, the adaptive ultrasound system and method herein represents a unified approach to imaging and therapy using arbitrary waveform generation allowing for wavefront synthesis in the region of interest. For example, in principle, given the target size and depth together with a general understanding of its surroundings (e.g. bone, ligaments, etc.), a custom-designed DMUA with a relatively small number of elements to produce high quality focusing (e.g., for imaging and/or therapy) within the target while avoiding the critical structures in the path of the beams may be provided. Therefore, for example, lower back pain, stroke, cardiac ablation, renal denervation and any number of applications where precise ablation is sought may be performed using the systems and/or methods herein.

At least one embodiment of this disclosure relates to image reconstruction (e.g., of a portion of the region of interest (e.g., as a region including perivascular tissue). For example, in one or more embodiments, a reconstructive approach is provided for pulsed ultrasound at single frequency. Such an exemplary single-frequency image reconstruction approach for pulse-mode ultrasound may have one or more of the following advantages. For example, by retaining the use of the pulsed nature of ultrasound the axial resolution of ultrasound may be maintained (e.g., axial resolution being determined by the transmit pulse shape). Further, for example, extracting a single frequency component of the pulse echo data at all depths, while accounting for transmit-receive beamforming models, allows for direct computation of a reflectivity map (e.g., which may be useful for analyzing the multilayer structure of blood vessels). This is in contrast to the difficulty in extracting reflectivity data from a full pulse packet echo due (e.g., a pulse packet being a group of frequencies forming a pulse initially traveling as a group, but their coherence being affected by dispersion in the propagation medium, frequency dependent scattering, attenuation, etc.) to the complexity of the structures. This may allow for some distinct advantages. For example, since reverberation is frequency-dependent, it may allow for more efficient dereverberation algorithms for improving image quality within the wall and in the lumen. Further, for example, a reliable model for reconstructing a property related to the multilayered nature of blood vessel may be important in analyzing vessels in a pre-disease state in a quantitative manner. Yet further, for example, the single-frequency echo components may provide a reliable way for separating speckle and specular reflections which may allow for quantitative ultrasound imaging of tissue architectures with high resolution (e.g., something that is currently impossible due to the almost inseparable speckle component in pulse packet form).

A computationally efficient algorithm for pulsed-mode single-frequency (PMSF) reconstruction may be implemented both in software and/or in hardware, e.g. on field programmable gate array (FPGA) circuitry of ultrasound scanners. Transmit and receive beams may be precomputed and tabulated at the frequency of interest and the region of interest within the image (see, e.g., FIGS. 6 and 7 herein).

One exemplary embodiment of an imaging method or system may include providing a running DFT computational block at a frequency of interest for each receiving element followed by a frequency-domain beamforming network (e.g., both of which may be implemented on an FPGA). Image reconstruction of the scattering function or other quantitative property of the ROI may be performed after the single-frequency image formation (e.g., which may be performed on a graphical processing unit (GPU)). Alternatively, a DFT processor may be deployed after beamforming and before the reconstruction block. In this case, the DFT and the reconstruction block may be performed on a GPU. In general, all three stages are computational stages and can be implemented in FPGA, GPU, multi-core CPUs or any appropriate processing unit(s) (see, e.g., FIG. 6 herein).

One or more embodiments of methods or systems described herein may include one or more of the following features or processes: 1) real-time implementation of an adaptive algorithm to optimize the imaging performance (e.g., based on specified signal to noise ratio (SNR) and/or contrast ratio (CR) values for a given control-point selection); this may further include, for example, transmit and receive beamforming; 2) real-time frequency separation using DFT or other efficient methods (e.g., narrowband filtering); and 3) a reconstruction algorithm operating on single frequency pulse-mode (SFPM) data once the optimal formation has been achieved.

One exemplary embodiment of an ultrasound imaging method may include providing a region of interest in a subject, defining a plurality of control points within the region of interest (e.g., wherein at least a first portion of the control points may be associated with a first identifiable portion of the region of interest and a second portion of the control points may be associated with a second identifiable portion of the region of interest that is different than the first identifiable portion), providing a transducer apparatus that includes a plurality of ultrasound transducer elements (e.g., wherein each of the plurality of ultrasound transducer elements may be configured to deliver ultrasound energy to the region of interest in response to a waveform applied thereto), and generating a waveform for each ultrasound transducer element of the plurality of ultrasound transducer elements. For example, generating the waveform may include selecting one or more imaging frequencies within a transducer apparatus bandwidth (e.g., each of the one or more imaging frequencies may be a carrier of a pulse to be transmitted having a finite bandwidth within the transducer bandwidth and having a time duration, such discrete frequencies being carriers of the finite bandwidth pulses) and generating element frequency components for each of the one or more imaging frequencies to form at least a part of the waveform to be applied to the ultrasound transducer element. The method may further include delivering ultrasound energy in pulse mode to the region of interest using the plurality of ultrasound transducer elements in response to waveforms generated for each of the plurality of ultrasound transducer elements, receiving pulse-echo data at each ultrasound transducer element of a plurality of ultrasound transducer elements from the region of interest in response to the delivered ultrasound energy to generate an image based thereon, separating pulse-echo components received from at least one of the first portion of the control points associated with the first identifiable portion of the region of interest and received from the second portion of the control points associated with the second identifiable portion of the region of interest, determining at least one of a contrast ratio (e.g., between the first and second identifiable portions based on the pulse-echo components received from the first portion of the control points associated with the first identifiable portion of the region of interest and the pulse-echo components received from the second portion of the control points associated with the second identifiable portion of the region of interest) and a signal to noise ratio (e.g., based on pulse-echo components received from a reference portion of the region of interest and pulse-echo components received from at least one of the first portion of the control points and the second portion of the control points), and modifying the waveform generated for one or more of the plurality of ultrasound transducer elements based on at least one of the contrast ratio and the signal to noise ratio.

One exemplary embodiment of a system for ultrasound imaging may include a transducer apparatus that includes a plurality of ultrasound transducer elements (e.g., wherein each of the plurality of ultrasound transducer elements may be configured to deliver ultrasound energy to a region of interest in response to a waveform applied thereto resulting in pulse-echo data therefrom) and a processing apparatus. The processing apparatus may be configured to provide a region of interest in a subject such that a plurality of control points may be defined within the region of interest (e.g., wherein at least a first portion of the control points may be associated with a first identifiable portion of the region of interest and a second portion of the control points may be associated with a second identifiable portion of the region of interest that is different than the first identifiable portion), generate a waveform for each ultrasound transducer element of the plurality of ultrasound transducer elements (e.g., such as by selecting one or more imaging frequencies within a transducer apparatus bandwidth with each of the one or more imaging frequencies being a carrier of a pulse to be transmitted having a finite bandwidth within the transducer apparatus bandwidth and having a time duration and generating element frequency components for each of the one or more imaging frequencies to form at least a part of the waveform to be applied to the ultrasound transducer element), control delivery of ultrasound energy in pulse mode to the region of interest using the plurality of ultrasound transducer elements in response to waveforms generated for each of the plurality of ultrasound transducer elements, control capture of pulse-echo data at each ultrasound transducer element of a plurality of ultrasound transducer elements from the region of interest in response to the delivered ultrasound energy to generate an image based thereon, separate pulse-echo components received from at least one of the first portion of the control points associated with the first identifiable portion of the region of interest and received from the second portion of the control points associated with the second identifiable portion of the region of interest, determine at least one of a contrast ratio (e.g., between the first and second identifiable portions based on the pulse-echo components received from the first portion of the control points associated with the first identifiable portion of the region of interest and the pulse-echo components received from the second portion of the control points associated with the second identifiable portion of the region of interest) and a signal to noise ratio (e.g., based on pulse-echo components received from a reference portion of the region of interest and pulse-echo components received from at least one of the first portion of the control points and the second portion of the control points), and modify the waveform generated for one or more of the plurality of ultrasound transducer elements based on at least one of the contrast ratio and the signal to noise ratio.

One or more embodiments of methods or systems described herein may include one or more of the following features or processes (e.g., for image formation to provide an image of the reflectivity map for an object): generating one or more excitation vectors (e.g., each excitation vector may be generated using field synthesis at a single frequency of the one or more imaging frequencies within the transducer bandwidth); an excitation vector generated that may include an element frequency component corresponding to each ultrasound transducer element of the plurality of ultrasound transducer elements; comparing at least the signal to noise ratio to a threshold value and the waveform generated for one or more of the plurality of ultrasound transducer elements may be modified based on the comparison; comparing at least the contrast ratio determined between the first and second identifiable portions to a threshold value and the waveform generated for one or more of the plurality of ultrasound transducer elements may be modified based on the comparison; and the waveform generated may be modified for one or more of the plurality of ultrasound transducer elements by at least one of adjusting gain at frequencies of the one or more frequencies located at one or more locations within the transducer apparatus bandwidth, and/or adjusting one or more pulse parameters including at least one of pulse duration, pulse shape, pulse amplitude, and pulse phase to adjust time-bandwidth product to improve at least one of contrast ratio or signal to noise ratio.

One or more embodiments of methods or systems described herein may include one or more of the following features or processes relating to image formation for vascular structure. Such embodiments of methods or systems described herein may include one or more of the following features or processes: the first portion of the control points may be associated with a vessel wall of a vascular structure (e.g., of a living subject) and the second portion of the control points may be associated with a lumen defined at least in part by the vessel wall; the plurality of control points within the region of interest may further include a third portion of the control points associated with tissue surrounding the vessel wall of the vascular structure; and pulse-echo components received from the third portion of the control points associated with the tissue may be separated from the pulse-echo components received from other portions of the control points and at least a contrast ratio between the tissue and at least one of the vessel wall or lumen may be determined for use in modifying the waveform generated for one or more of the plurality of ultrasound transducer elements.

One or more embodiments of methods or systems described herein may include one or more of the following features or processes related to image reconstruction (e.g., following image formation to provide an image of the reflectivity map for an object). Such embodiments of methods or systems described herein may include or such reconstruction processes may be used alone to provide a reconstructed image using one or more of the following features or processes: separating, from the pulse echo data received, at least a portion thereof received at each ultrasound transducer element from the region of interest in response to the delivered ultrasound energy corresponding to a single frequency of the one or more image frequencies and reconstructing an image representative of one or more properties in the region of interest from the separated pulse-echo data corresponding to the single frequency of the one or more image frequencies; and/or separating, from the pulse echo data received, one or more additional portions thereof received at each ultrasound transducer element from the region of interest in response to the delivered ultrasound energy corresponding to one or more additional single frequencies of the one or more image frequencies, reconstructing an image representative of one or more properties in the region of interest from the separated pulse-echo data corresponding to each of the single frequencies of the one or more image frequencies, and combining the reconstructed images corresponding to multiple frequencies within the transducer apparatus bandwidth.

Further, one or more embodiments of methods or systems described herein may include one or more of the following features or processes (e.g., related to delivering therapy): therapy may be delivered or the system may be configured to deliver therapy to a patient based on identification of at least one vascular characteristic of the region of interest in which at least one portion of a blood vessel is located. For example, the system may be configured to deliver therapy based on identification of the at least one vascular characteristic of the region of interest in which at least one portion of a blood vessel is located, the transducer apparatus used to deliver ultrasound energy and receive pulse-echo data may also be configured to generate ultrasonic energy to deliver therapy, etc.

Another exemplar embodiment of an ultrasound imaging method (e.g., for reconstructing an image representative of one or more properties in the region of interest, such as scattering in the region of interest, speed of sound, attenuation, and reflection coefficients) may include providing a region of interest in a subject, providing a transducer apparatus including a plurality of ultrasound transducer elements (e.g., wherein each of the plurality of ultrasound transducer elements may be configured to deliver ultrasound energy to the region of interest in response to a waveform applied thereto), and generating a waveform for each ultrasound transducer element of the plurality of ultrasound transducer elements. The waveform may be generated by selecting one or more imaging frequencies within a transducer apparatus bandwidth (e.g., each of the one or more imaging frequencies may be associated with a pulse to be transmitted having a finite bandwidth within the transducer bandwidth and having a time duration, such discrete frequencies being carriers of the finite bandwidth pulses) and generating element frequency components for each of the one or more imaging frequencies to form at least a part of the waveform to be applied to the ultrasound transducer element. The method may further include delivering ultrasound energy in pulse mode to the region of interest using the plurality of ultrasound transducer elements in response to waveforms generated for each of the plurality of ultrasound transducer elements, receiving pulse-echo data at each ultrasound transducer element of a plurality of ultrasound transducer elements from the region of interest in response to the delivered ultrasound energy, separating, from the pulse echo data received, at least a portion thereof received at each ultrasound transducer element from the region of interest in response to the delivered ultrasound energy corresponding to a single frequency of the one or more image frequencies, and reconstructing an image representative of one or more properties in the region of interest from the separated pulse-echo data corresponding to the single frequency of the one or more image frequencies.

Another exemplary system for ultrasound imaging (e.g., for reconstructing an image representative of one or more properties in the region of interest, such as scattering function, speed of sound, attenuation, and reflection coefficients) may include a transducer apparatus that includes a plurality of ultrasound transducer elements (e.g., wherein each of the plurality of ultrasound transducer elements may be configured to deliver ultrasound energy to a region of interest in response to a waveform applied thereto resulting in pulse-echo data therefrom) and processing apparatus. At least in one embodiment, the processing apparatus is configured to generate a waveform for each ultrasound transducer element of the plurality of ultrasound transducer elements (e.g., wherein the processing apparatus may be configured to generate the waveform by selecting one or more imaging frequencies within a transducer apparatus bandwidth with each of the one or more imaging frequencies being a carrier of a pulse to be transmitted having a finite bandwidth within the transducer apparatus bandwidth and having a time duration, and generating element frequency components for each of the one or more imaging frequencies to form at least a part of the waveform to be applied to the ultrasound transducer element), control delivery of ultrasound energy in pulse mode to the region of interest using the plurality of ultrasound transducer elements in response to waveforms generated for each of the plurality of ultrasound transducer elements, control capture of pulse-echo data at each ultrasound transducer element of a plurality of ultrasound transducer elements from the region of interest in response to the delivered ultrasound energy to generate an image based thereon, separate, from the pulse echo data received, at least a portion thereof received at each ultrasound transducer element from the region of interest in response to the delivered ultrasound energy corresponding to a single frequency of the one or more image frequencies, and reconstruct an image representative of one or more properties in the region of interest from the separated pulse-echo data corresponding to the single frequency of the one or more image frequencies.

One or more of the methods or systems may further include or may be configured to execute separating, from the pulse echo data received, one or more additional portions thereof received at each ultrasound transducer element from the region of interest in response to the delivered ultrasound energy corresponding to one or more additional single frequencies of the one or more image frequencies, reconstructing an image representative of one or more properties in the region of interest from the separated pulse-echo data corresponding to each of the single frequencies of the one or more image frequencies, and combining the reconstructed images corresponding to multiple frequencies within the transducer apparatus bandwidth (e.g., compounding of reconstructed images; wherein each reconstructed corresponds to a single frequency image of a plurality of image frequencies).

Further, one or more embodiments of the method or system (e.g., used to reconstruct images) may include generating element frequency components for each of the one or more imaging frequencies to form at least a part of the waveform to be applied to the ultrasound transducer element by generating one or more excitation vectors (e.g., wherein generating the one or more excitation vectors may include generating each excitation vector using field synthesis at a single frequency of the one or more imaging frequencies within the transducer bandwidth). Further, the excitation vector generated may include an element frequency component corresponding to each ultrasound transducer element of the plurality of ultrasound transducer elements.

Further, in one or more embodiments of the method or system (e.g., used to reconstruct images) the region of interest may include a vessel wall of a vascular structure of the subject and a lumen defined at least in part by the vessel wall, and/or may include or be configured to deliver therapy to a patient based on identification of at least one vascular characteristic of the region of interest in which at least one portion of a blood vessel is located.

Further, in one or more embodiments of the method or system (e.g., image formation, image reconstruction, etc.), receiving pulse-echo data at each ultrasound transducer element of a plurality of ultrasound transducer elements from the region of interest in response to the delivered ultrasound energy may include using a discrete Fourier transform based filter bank for separation of pulse-echo data. For example, in one or more embodiments, the methods or systems herein may be configured to use a discrete Fourier transform based filter bank for separation of pulse-echo data.

Further, in one or more embodiments of the method or system, the one or more imaging waveforms may include a finite number of randomly selected single frequency components with each single frequency component being a carrier having a finite bandwidth specified by its duration and modulating pulse.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 5 is an exemplary waveform synthesis algorithm for use in the ultrasound adaptive imaging method of FIG. 3 as related to vascular structures.

DETAILED DESCRIPTION OF EXEMPLARY EMBODIMENTS

Figure 1:
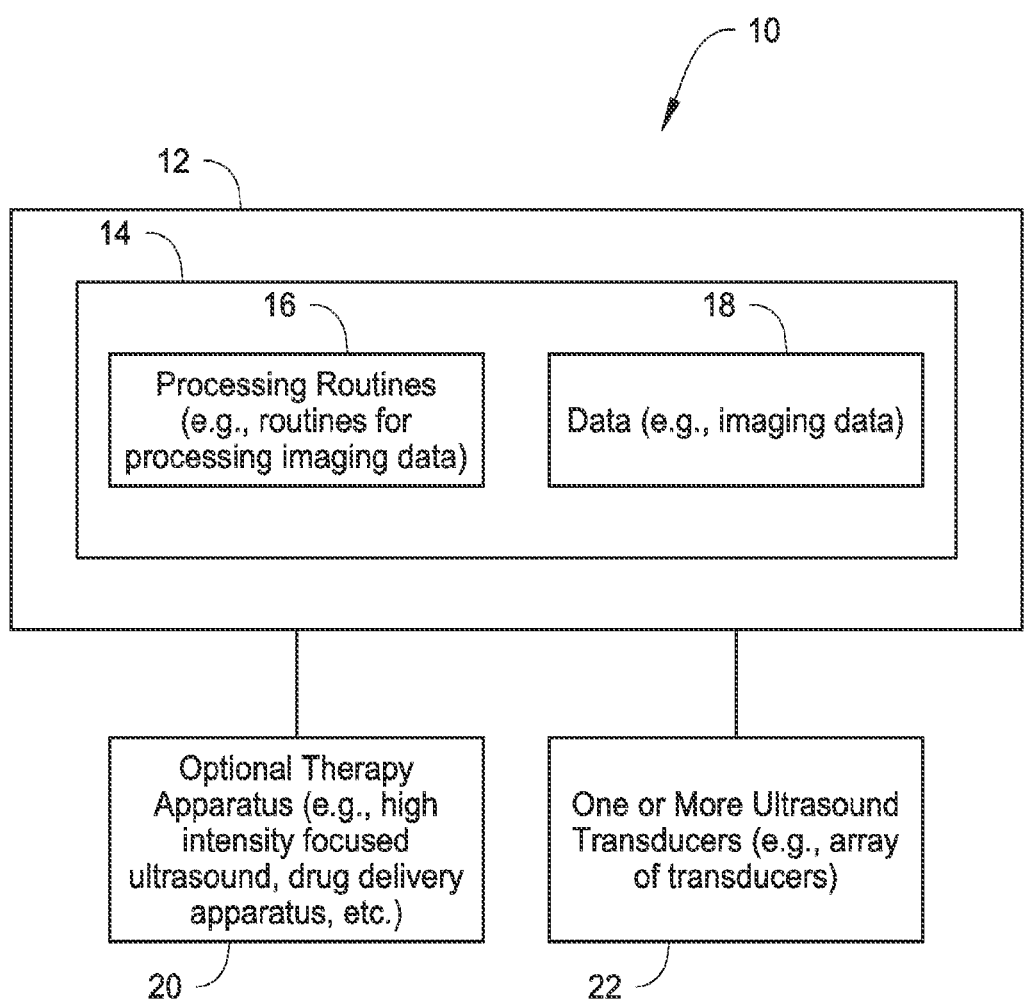
FIG. 1 is a block diagram depicting an exemplary ultrasound imaging system, with an optional therapy system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-14. It will be apparent to one skilled in the art that elements or processes (e.g., including steps thereof) from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 shows an exemplary ultrasound imaging system 10 including processing apparatus (block 12) (e.g., controller) and one or more ultrasound transducers, such as a transducer array that provides for transmission of pulses and reception of echoes (block 22). The processing apparatus (block 12) may be operably coupled to the one or more transducers (block 22) to facilitate imaging of an object of interest (e.g., capture of pulse-echo data from a region of interest) using the one or more transducers (block 22). Further, the processing apparatus (block 12) includes data storage (block 14). Data storage (block 14) allows for access to processing programs or routines (block 16) and one or more other types of data (block 18) that may be employed to carry out the exemplary imaging processes or methods (e.g., one which is shown generally in the block diagram of FIG. 2).

For example, processing programs or routines (block 16) may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein (e.g., provide imaging, image reconstruction, etc.). Exemplary mathematical formulations/equations that may be used in the systems and methods described herein are more specifically described herein with reference to FIGS. 3-19.

Data (block 18) may include, for example, sampled pulse-echo information (e.g., sampled or collected using the one or more transducers (block 22)), data representative of measurements (e.g., measurements of structure in the region of interest, vascular properties or characteristics, etc.), results from one or more processing programs or routines employed according to the disclosure herein (e.g., reconstructed images of an object of interest, such as a blood vessel or regions around same), or any other data that may be necessary for carrying out the one or more processes or methods described herein.

In one or more embodiments, the system 10 may be implemented using one or more computer programs executed on programmable computers, such as computers that include, for example, processing capabilities (e.g., central processing units (CPUs), graphical processing units (GPUs)), data storage (e.g., volatile or non-volatile memory and/or storage elements), input devices, and output devices. Program code and/or logic described herein may be applied to input data to perform functionality described herein and generate desired output information (e.g., ultrasound images, reconstructed images, etc.). The output information may be applied, or otherwise used, as input to, or by, one or more other devices and/or processes as described herein (e.g., one or more therapy apparatus (block 20) such as a drug therapy apparatus, an ultrasound therapy apparatus, etc.).

The program(s) or routine(s) used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer (e.g., processor(s)) when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the imaging system 10 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus (block 12), may be, for example, any fixed or mobile computer system (e.g., a personal computer or minicomputer, for example, with a CPU, GPU, etc.). The exact configuration of the computing apparatus is not limiting and essentially any device capable of providing suitable computing capabilities and control capabilities (e.g., control the imaging set up configuration and acquire data, such as pulse-echo data) may be used. Further, various peripheral devices, such as a computer display, mouse, keyboard, memory, printer, scanner, etc. are contemplated to be used in combination with the processing apparatus (block 12), such as for visualization of imaging results (e.g., display of images, display of therapy delivery in real time such as with use of high intensity focused ultrasound, etc.).

Further, in one or more embodiments, the output (e.g., an image, image data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, magnetic recordable tape, etc.) containing digital bits (e.g., encoded in binary, trinary, etc.) that may be readable and/or writeable by processing apparatus (block 14) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to generate ultrasound images and/or reconstruct images described herein (e.g., from pulse-echo data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information. For example, such a user interface may allow a user to define control points (e.g., select points on a display panel, touchscreen, etc.), enter threshold values, perform therapy, use any of the features or functionality described herein, etc.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, cloud storage, or the like. The instructions may be executed by one or more processors to support one or more aspects of the functionality described in this disclosure.

The imaging system 10 may further be used with, or may form a part of an optional therapy apparatus (block 20). For example, the therapy apparatus (block 20) may use the results of ultrasound imaging to provide one or more therapies. In one or more embodiments, the therapy apparatus (block 20) may be a non-invasive or invasive therapy apparatus such as a drug delivery apparatus or system (delivery of a drug to a particular location), a surgical apparatus or system (e.g., delivery of a stent to a particular position), an ablation apparatus or system (e.g., a high intensity focused ultrasound therapy apparatus or system), etc.

In one or more embodiments, the therapy apparatus (block 20) may be a separate system or apparatus that receives an output from the imaging system (e.g., image information) and delivers one or more therapies. In other embodiments, the therapy apparatus (block 20) may be integrated with the imaging system to perform the one or more therapies (e.g., a high intensity focused ultrasound system that uses dual mode ultrasound transducer(s) for diagnostics such as imaging, as well as for treatment, such as ablation). For example, in one or more embodiments, the therapy apparatus (block 20) may include one or more portions of a system such as described in PCT International Publication No. WO2009/002492 entitled "Image Guided Plaque Ablation," published 31 Dec. 2008, and incorporated herein by reference. For example, the ultrasound imaging described herein may be used for reducing vascular plaque non-invasively. For example, the ultrasound imaging described herein may be used to identify flow and vascular characteristics needed to non-invasively perform ablation of plaque as described in PCT International Publication No. WO2009/002492. Further, for example, one or more embodiments of the present disclosure may incorporate one or more features as described in U.S. Patent Application Publication No. US2012/0283564 A1 entitled "Vascular Characterization Using Ultrasound Imaging" published 8 Nov. 2012, and incorporated herein by reference (e.g., including, for example, any image formation and/or reconstruction approaches described therein).

For example, the system may include a therapy system for non-invasively elevating the temperature of tissue by ultrasound energy waves including: at least one ultrasound delivery device adapted to deliver ultrasound energy waves to a focal point of targeted tissue; a temperature monitoring device for monitoring the temperature of targeted tissue at the focal point; and a controller for steering and controlling the ultrasound delivery device to deliver ultrasound energy waves at a focal point to elevate the temperature of targeted tissue to a desired temperature.

Further, for example, the therapy system may use one or more imaging systems described herein to produce an image of at least a portion of a mammalian body, e.g., such that the location of at least one vascular plaque in said image can be determined and to ascertain the location of the base of said vascular plaque. For example, ultrasound delivery device may ascertain one or more target locations at the base of the plaque. Still further one or more embodiments of the imaging system provided herein may be used in a method for elevating the temperature at a target location by an energy wave using an ultrasound therapy system (e.g., which may be the same ultrasound system (ultrasound transducers thereof) used for imaging). For example, the method may include delivering a beam of ultrasound energy waves from a source to the target location; monitoring the temperature of the target location; and stopping the delivering of the beam of ultrasound energy waves if a desired temperature at the target location has been reached.

Further, a method of preparing a plan for non-invasively elevating the temperature of tissue in a vessel wall leading to regression of vascular plaques may include imaging at least a portion of a body to produce an image (e.g., using ultrasound imaging as described herein to image a vascular region); determining the location of at least one vascular plaque in said image; ascertaining the location of the base of said vascular plaque and one or more target locations at the base of the plaque (e.g., using the ultrasound generated image); and/or determining the parameters for delivering ultrasound energy waves from a source to a focal point for elevating the temperature of targeted tissue in the vessel wall to a desired temperature, sufficient for reducing or destroying vaso vasorum.

Further, for example, the ultrasound imaging described herein may be used to identify flow and vascular characteristics needed to perform invasive treatments of plaque (e.g., stent delivery, cardiac surgery, etc.)

Still further, in one or more embodiments, the therapy apparatus (block 20) may include one or more portions of a system such as described in U.S. Patent Application Publication No. US2013/0144165 A1, entitled "Dual Mode Ultrasound Transducer (DMUT) System and Method for Controlling Delivery of Ultrasound Therapy" published 6 Jun. 2013 and which is incorporated by reference herein. For example, the ultrasound imaging described herein may be performed with the same or similar transducer arrays described therein which can be used for both imaging (e.g., to monitor a therapy procedure), as well as for delivering therapy (e.g., to deliver high intensity focused ultrasound energy). For example, therapy may be delivered using the ultrasound transducer array, while the imaging modes using the same transducer array may be used to guide the therapeutic beam, assess thermal and mechanical tissue response to estimate doses of therapy (e.g., initial dose of therapy), monitor and characterize tissue response during therapy, and assess the state of the treated tissue at the completion of each exposure to the therapeutic ultrasound energy (e.g., real time monitoring between periods of therapy delivery).

Figure 11:
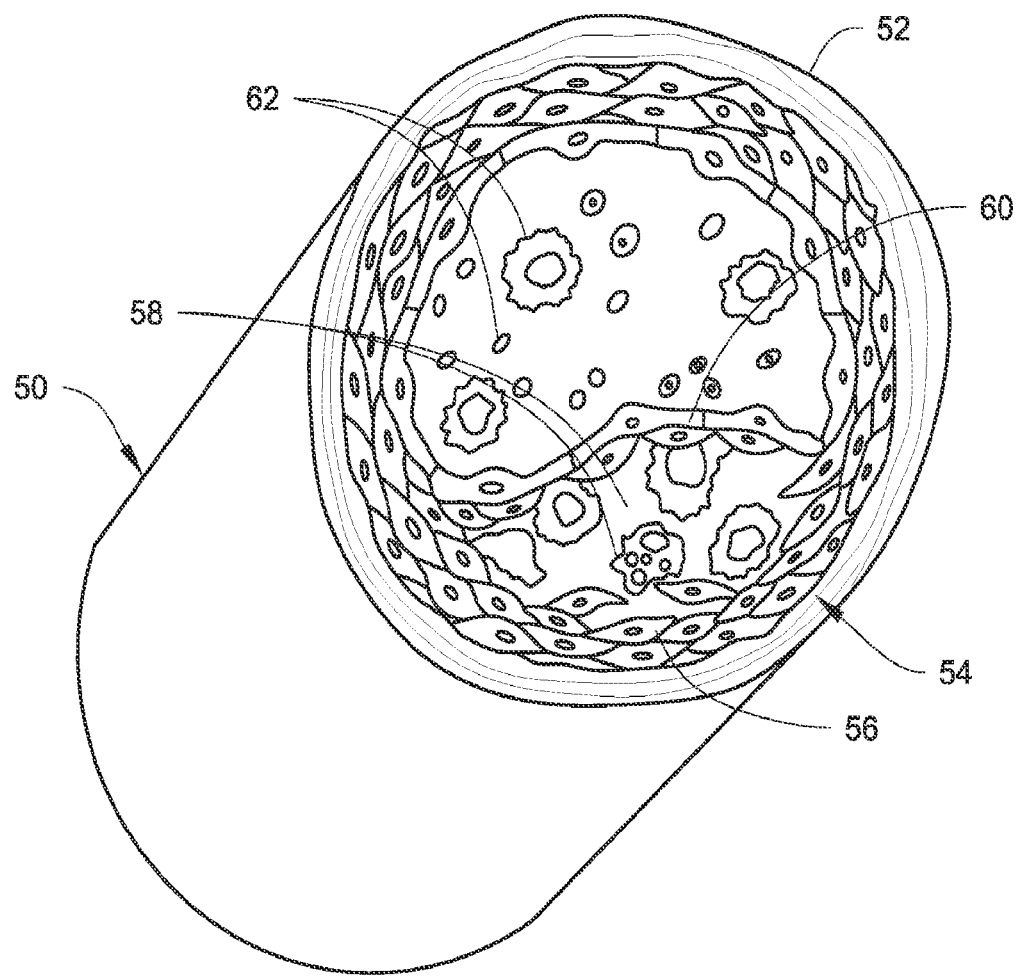
FIG. 11 provides an exemplary image of a blood vessel for use in describing one or more methods and/or systems shown generally herein as they relate to vascular diagnostics or vascular therapy.

For example, ultrasound imaging as described herein may be used to identify one or more vascular characteristics. An exemplary diagram of a blood vessel 50 is shown in FIG. 11 to facilitate discussion of the use of imaging described herein. The blood vessel 50 shown in FIG. 11 includes a vessel wall 52 having a plaque structure 54 formed on the interior of the vessel wall 52. The plaque architecture of the structure 54 may include, for example, a plaque base 56, a lipid core 58, and a fibrous or calcified cap 60. Blood 62 flows through the blood vessel 50 defined by the vessel wall 52.

One or more embodiments of methods and/or systems described herein may be used to identify one or more vascular characteristics, e.g., flow characteristics associated with the flow through the blood vessel 50, structural characteristics associated with the blood vessel 50, and/or hemodynamic characteristics. For example, flow characteristics may include flow velocity, volume flow, wall shear stress, wall shear rate, etc.

For example, structural characteristics may include determining boundaries of the vessel wall (e.g., outer and inner boundaries, such as in a coordinate system), thickness of the vessel wall, measurement of tissue properties within the vessel wall (e.g., stiffness of tissue, such as, for example, it relates to a diseased state), differentiation of plaque from vessel wall, differentiation of the various components of plaque (e.g., differentiation of base from lipid core, differentiation of base from fibrous cap, differentiation of lipid core from fibrous cap, etc.), etc. For example, in one or more embodiments, upon differentiation of the base from the fibrous cap of the plaque architecture, treatment may be provided to ablate the base to reduce further plaque buildup or growth or provide treatment according to PCT International Publication No. WO2009/002492.

Still further, for example, hemodynamic characteristics may include calculated hemodynamic measurements, such as, for example, arterial pressure, cardiac output, arterial compliance, pulse wave velocity, etc. At least in one embodiment, such hemodynamic measurements may be determined based on parameters relating to both tracking of the blood flow and tracking of vessel wall motion or displacement. As such, to obtain an accurate hemodynamic determination, the parameters or measurements relating to both tracking of the blood flow and tracking of vessel wall motion or displacement must be determined simultaneously, or within a periodic cycle in which both can be determined (e.g., determined effectively). For example, compliance of the vessel may be based on both volume flow which relates to tracking of blood flow and pressure within the vessel which can be determined by tracking vessel displacement.

In one or more embodiments, the ultrasound quantitative imaging system may be used for assessment of the disease state in atherosclerotic blood vessels. For example, the imaging may be used for the direct estimation of the strain fields in the vicinity of the vessel walls. Such methods may mitigate the deleterious effects of local deformations that could result in loss of correlation, and which may render the correlation-based speckle tracking approach useless in the vicinity of the vessel wall. Such deformations, depending on severity, could result in erroneous estimate in the velocity (and therefore strain) estimation or may even result in loss of accuracy.

The one or more ultrasound transducers (block 22) may be any apparatus (e.g., transmitting, receiving components, etc.) capable of delivering ultrasound pulses and sampling/collecting ultrasound echo energy contemplated to be used in ultrasound imaging systems and in combination with processing apparatus (block 12) of the system 10. As used herein, such transducers may include a transmitting portion, e.g., to deliver pulse energy, and a receiving portion, e.g., to sample/collect echo or reflected energy, which may or may not be the same portion. During the ultrasound imaging of a target (e.g., a blood vessel, such as a carotid artery, coronary artery, etc.), the one or more transducers (block 22) may be positioned relative to the target so as to be capable of delivering energy to the target resulting in reflected energy (also known as the resultant pulse-echo or echo energy) and also sampling the echo energy.

The one or more transducers (block 22) may include multiple transducers position separately from one another or may be a transducer array. In one or more embodiments, various arrays may have one or more benefits over others. For example, in one or more embodiments, the transducer array may be a segmented concave transducer with multiple sub-apertures to insonify the vessel from multiple angles. This will allow for better definition of the vessel boundaries from more directions. At least one sub-aperture may be used in linear array or phased array mode for initial B-mode and strain imaging of the vessel. The driver of the transducer may be designed to drive the multiple sub-apertures with independent codes. Each sub-aperture may be a one-dimensional or two-dimensional array. Coded excitation may help improve both the data rates (e.g., provide higher frame rates) and echo quality (e.g., by reducing reverberations within the lumen). The receiver may be a multichannel receiver with beamforming and/or pulse compression for coded excitation.

For example, various arrays and operation thereof, are described in Ebbini et al., "Dual-Mode Ultrasound Phased Arrays for Image-Guided Surgery," *Ultrasound Imaging*, vol. 28, pp. 65-82 (2006); Ballard, et al., "Adaptive Transthoracic Refocusing of Dual-Mode Ultrasound Arrays," *IEEE Transactions on Biomedical Engineering*, vol. 57, no. 1, pp. 93-102 (January 2010); Wan et al., "Imaging with Concave Large-Aperture Therapeutic Ultrasound Arrays Using Conventional Synthetic-Aperture Beamforming," *IEEE Transactions on Ultrasound, Ferroelectrics, and Frequency Control*, vol. 55, no. 8, pp. 1705-1718 (August 2008); and Y. Wan and E. S. Ebbini, "A Post-beamforming 2-D Pseudoinverse Filter for Coarsely Sampled Ultrasound Arrays," *IEEE Trans on Ultrasonics, Ferroelectrics, and Frequency Control*, vol. 56, no. 9, pp. 1888-1902 (2009), which are all hereby incorporated by reference herein.

Figure 2:
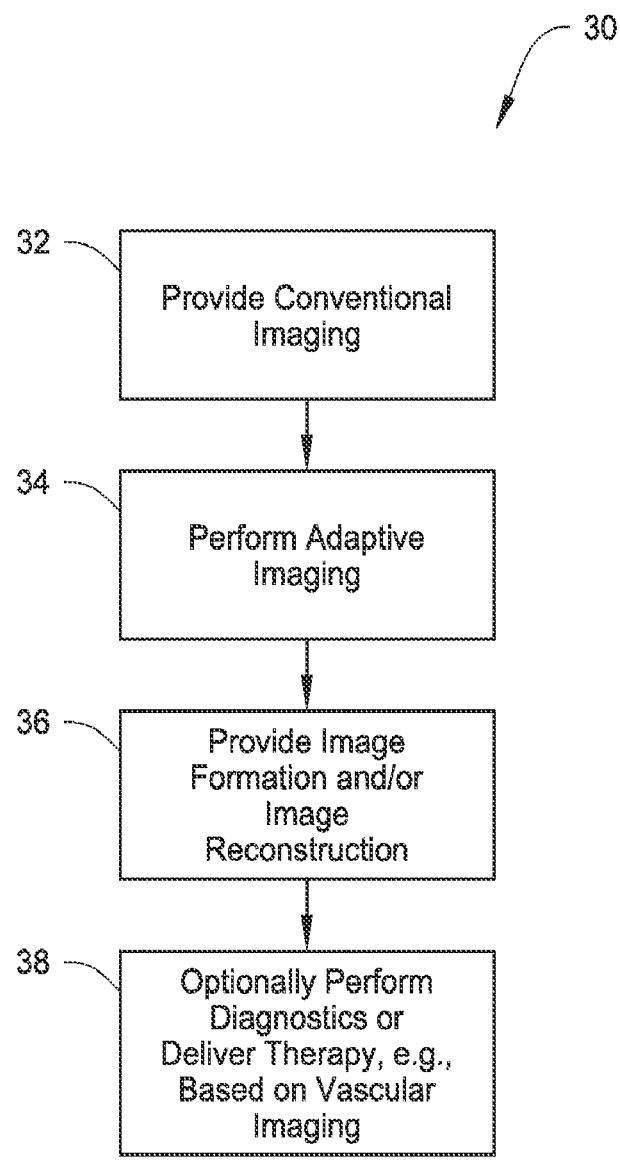
FIG. 2 is a flow chart depicting an exemplary ultrasound imaging method, with optional diagnostics or therapy.

A flow chart of an exemplary method 30 using ultrasound imaging as described herein is depicted in FIG. 2. One will recognize that one or more of the blocks of functionality described herein may be carried out using one or more programs or routines, and/or any other components of an imaging system (e.g., the imaging system 10 of FIG. 1) and/or therapy system (e.g., the therapy apparatus 20 of FIG. 1).

Generally, the method 30 may include providing imaging of a region of interest (e.g., an ultrasound image of a region of interest using conventional ultrasound processes) (block 32). For example, the region of interest may be a region in a living subject (e.g., a human, an animal, etc.) such as a blood vessel, spinal region, brain region, kidney region, etc. For example, imaging may be performed using conventional synthetic aperture (SA) imaging, conventional B-mode imaging, M2D mode imaging (see, Liu and Ebbini, "Real-time 2D Temperature Imaging Using Ultrasound," IEEE T-BME, vol. 57, no. 1, pp. 12-16 (2010), etc. Further, for example, such imaging may be provided using other imaging technology such as magnetic resonance imaging (MRI), simultaneously or prior to the ultrasound scan, etc.

The method 30 may further perform adaptive ultrasound imaging using a plurality of control points defined within the region of interest (block 34) (e.g., to provide data for ultrasound image formation). In one or more embodiments, adaptive coded waveforms for application to ultrasound transducer elements of a transducer apparatus are designed to match the spectral content of the target or region of interest (e.g., a specular reflector like a blood vessel wall). Further, in one or more embodiments, the target or region of interest is defined by a set of appropriately selected control points. Such control points being used to define one or more performance criteria of the imaging system (e.g., signal-to-noise ratio, contrast ratio, etc.). For example, in one or more embodiments of the adaptive imaging, contrast ratio (CR) in the target region is incorporated as a measure for adjusting (e.g., increasing) bandwidth of the coded waveforms. Further, for example, in one or more embodiments of the adaptive imaging, signal-to-noise ratio (SNR) is incorporated as a measure for adjusting (e.g., improving) a spectral match between the coded waveforms at the frequency response of that target region (e.g., including the control points), for example, which may reduce the effective bandwidth (BW). Still further, in one or more embodiments of the adaptive imaging, a computationally efficient DFT-based filter bank (e.g., a pre-beamforming filter bank or a post-beamforming filter bank) may be used for analysis of pulse echo data received from the target region (e.g., including from the control points).

It will be recognized that the adaptive imaging described herein is distinctly different from the spread-spectrum approaches described, for example, in article, T. Misardis and J. A. Jensen, "Use of modulated excitation signals in medical ultrasound. Part I: basic concepts and expected benefits," *IEEE Trans. Ultrason., Ferroelect., Freq. Contr.*, vol. 52, no. 2, pp. 177-191 (February 2005) or in U.S. Patent Application Publication No. US2013/0123635 A1, to Wegner entitled "Spread Spectrum Coded Waveforms in Ultrasound Imaging." For example, such previously described spread spectrum approaches do not use waveform synthesis based on specific definition of control points within the target region of interest as described herein, do not provide an adaptive waveform code design that achieves specified contrast ratio and signal-to-noise ratio values within the region of interest as described herein (e.g., the adaptive imaging herein provides a time bandwidth (TBW) product that is adjustable and different control points in the region of interest compared to an open loop waveform design), and do not use running DFT-based detection and reconstruction components employed pre-beamforming and/or post-beamforming as part of the receiver chain.

Further, with reference to FIG. 2, the adaptive imaging process (block 34) provides image data such that image formation and/or image reconstruction may be provided (block 36). Based upon such imaging, optional diagnostic and/or therapy processes may be performed (block 38) (e.g., HIFU processes, drug delivery, identification of diseased coronary structure, etc.).

Figure 3:
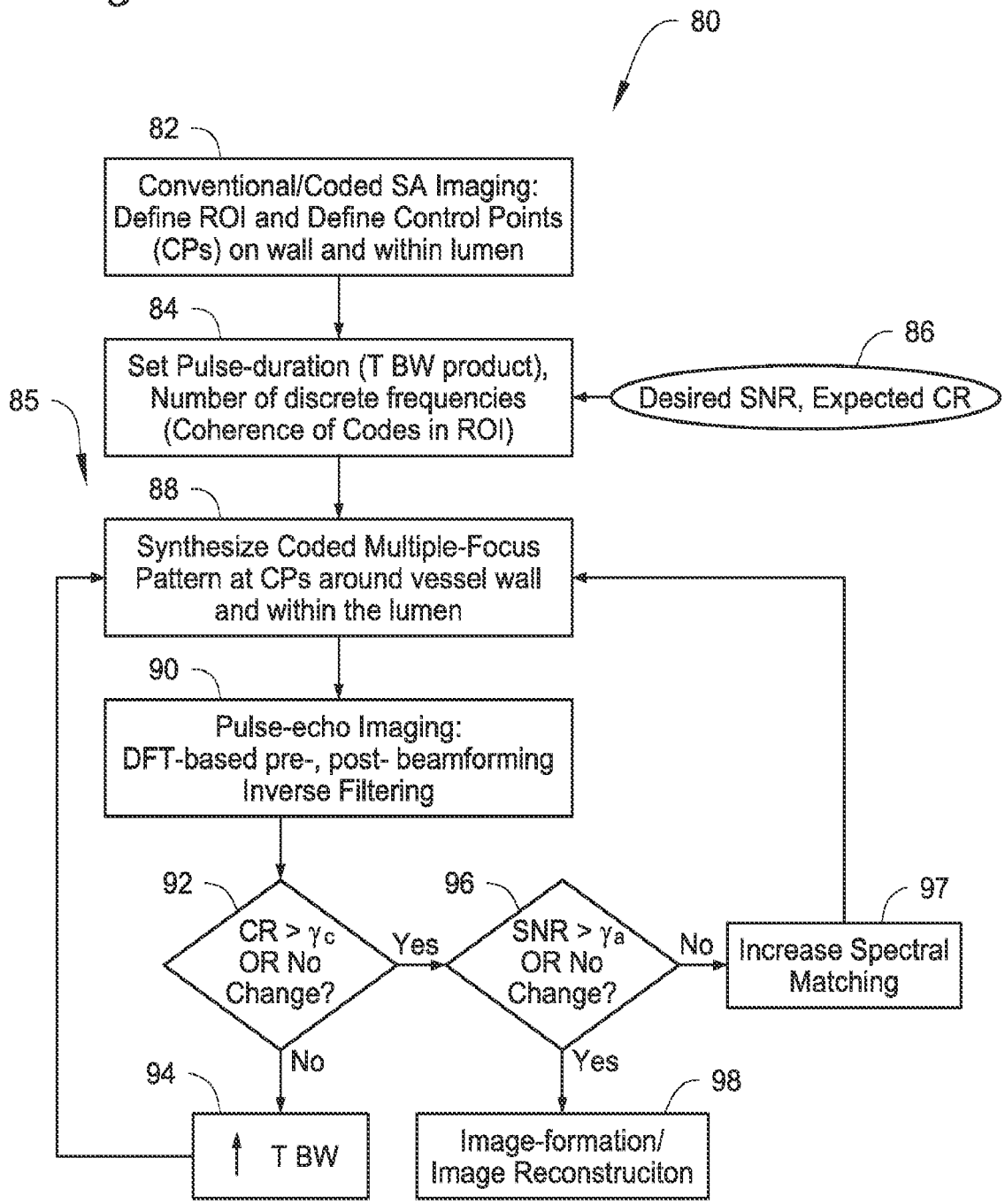
FIG. 3 is a flow chart depicting an exemplary ultrasound adaptive imaging method.

A flow chart of an exemplary adaptive imaging method 80 is depicted in FIG. 3 and shall be described with reference thereto as well as to FIGS. 4-5. Generally, the method 80 includes providing a region of interest such as described with reference to FIG. 2 (e.g., an ultrasound image of a region of interest using conventional ultrasound imaging, such as conventional synthetic aperture (SA) imaging, conventional B-mode imaging, M2D mode imaging, etc.). For example, as shown in block 82, conventional/coded SA imaging may be used. With such imaging provided, a region of interest (ROI) is defined and control points (CPs) in the region of interest are defined (also shown in block 82). For example, such imaging may be provided using a transducer apparatus that includes a plurality of ultrasound transducer elements (e.g., such as shown generally in FIG. 1, wherein each of the plurality of ultrasound transducer elements being configured to deliver ultrasound energy to the region of interest in response to a waveform applied thereto). For example, block 82 more specifically describes the adaptive imaging starting from a conventional imaging process used to define the region of interest (ROI) and a set of control points (CPs) (e.g., which, in the context of vascular imaging, the CPs may be associated with the wall and lumen of a target vessel within the ROT).

Generally, for example, the control points defined in the region of interest correspond to identifiable portions therein. For example, at least a first portion of the control points may be associated with a first identifiable portion of the region of interest, a second portion of the control points may be associated with a second identifiable portion of the region of interest, and so forth. At least in one embodiment, the different portions of the control points correspond to identifiable portions of the region of interest that are distinct and/or different from each other portions therein. For example, as described herein, a first portion of the control points may be associated with a vessel wall of a vascular structure and the second portion of the control points may be associated with a lumen defined by at least a part of the vessel wall. Further, for example, a third portion of the control points may be associated with tissue about the vessel wall.

The selection of the CPs may be based on an initial hypothesis of the vessel wall location. This hypothesis may be formed based on conventional DMUA imaging or other a priori information, such as information from magnetic resonance imaging (MRI), diagnostic ultrasound imaging, intravascular ultrasound (IVUS) imaging, etc. For example, FIG. 4 illustrates the use of a DMUA 40 in imaging a cross-sectional view of a blood vessel wall 42 with assumed inner diameter 43 and outer diameter 44 (e.g., inner and outer diameters of 5.2 mm and 6.8 mm, respectively). The candidate CPs are shown as "Xs" and "Os" on a grid covering the lumen 45, vessel wall 42, and some of the surrounding tissues 46 around or about the vessel wall 42.

Figure 4:
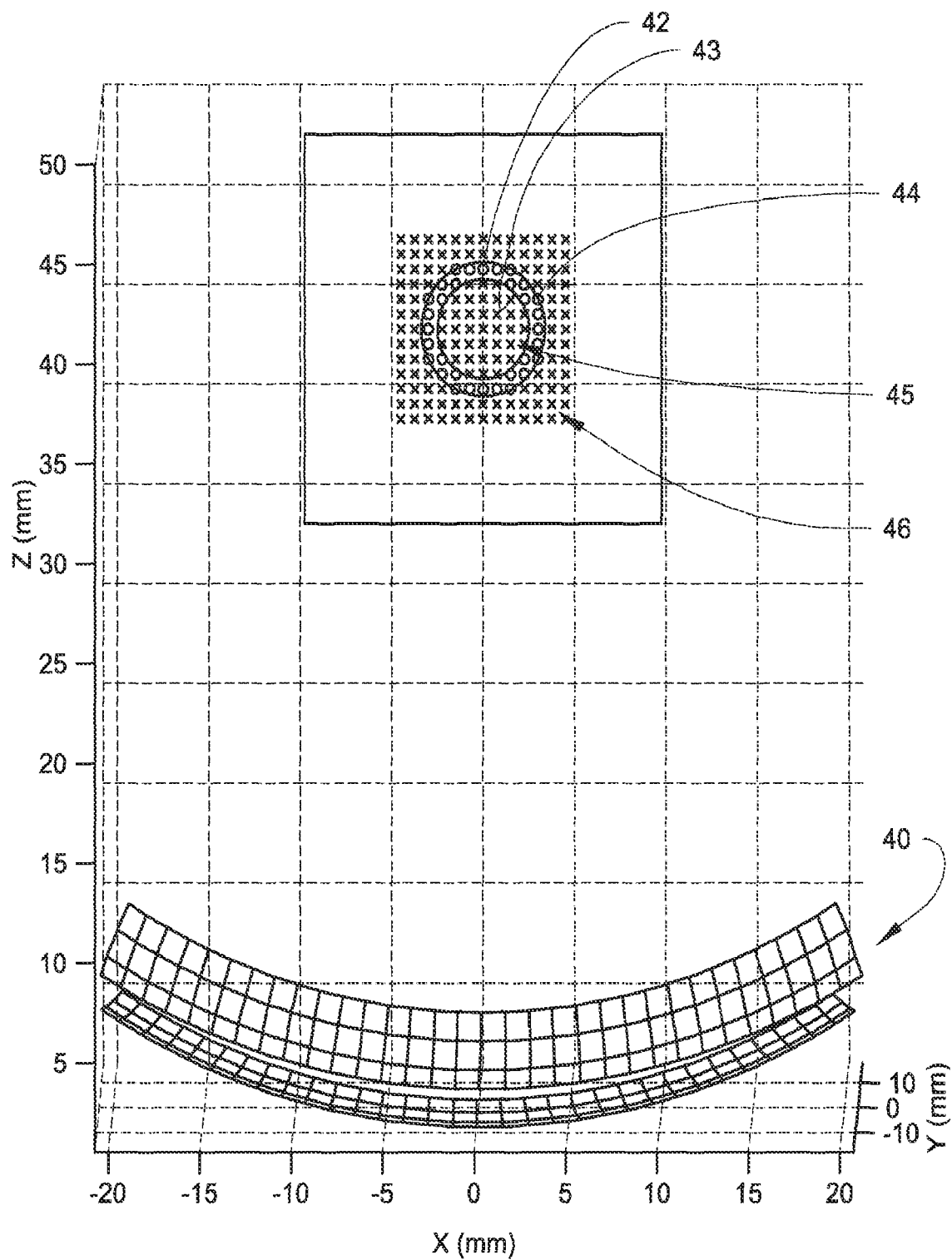
FIG. 4 is an illustration for use in describing the exemplary ultrasound adaptive imaging method of FIG. 3 as related to vascular structures.

FIG. 4 also shows an array point spread function (psf) (e.g., discernible in gray scale as lighter at the center of the lumen 45 and having different shades outward therefrom) at a single frequency when focused at its geometric center. This classical psf illustrates the relatively high lateral resolution compared to the axial resolution in this single frequency (e.g., continuous wave (CW)) case. Broadband spectrum of the array excitation may improve the axial resolution.

Based on the hypothesized vessel wall geometry, a user can designate the CPs as vessel wall CPs (i.e., circles or Os), lumen CPs (Xs in lumen 45) or tissue CPs (Xs about the vessel wall 42). These candidate CPs and their designations can be modified based on adaptive imaging tests described herein. It is noted that the hypothesis does not limit the ability of image reconstruction algorithms to adaptively modify the wall geometry as a result of actual hypothesis testing based on multi-frequency echo data from the ROI.

With further reference to FIG. 3, the adaptive imaging method 80, for example, using waveform synthesis, generates a waveform for each ultrasound transducer element of the plurality of ultrasound transducer elements used in the process (shown generally by arrow 85). For example, the waveform may be generated by selecting one or more imaging frequencies within a transducer apparatus bandwidth. Each of the one or more imaging frequencies may be associated with (e.g., be a carrier for) a pulse to be transmitted having a finite bandwidth within the transducer apparatus bandwidth.

Element frequency components (e.g., frequency component for each transducer element) are then generated for each of the one or more imaging frequencies to form at least a part of the waveform to be applied to the ultrasound transducer element. In at least one embodiment, the transducer element frequency components are provided by generating one or more excitation vectors. For example, each excitation vector may be generated using field synthesis at a single frequency of the one or more imaging frequencies within the transducer apparatus bandwidth. The excitation vector generated includes an element frequency component corresponding to each ultrasound transducer element of the plurality of ultrasound transducer elements used for the adaptive process. In one or more embodiments, the term field synthesis refers to the use of single frequency component to produce a specified multiple focus pattern using a geometrically defined transducer array. For example, this may be achieved by solving an inverse problem that computes the complex excitation vector to the array elements. The complex elements of the excitation vector may define the magnitude and phase of the sinusoidal signals driving the array elements to realize the specified field pattern. This approach is, for example, described in Ebbini et al., "Multiple-focus ultrasound phased-array pattern synthesis: Optimal driving-signal distributions for hyperthermia", *IEEE Transactions on Ultrasonics, Ferroelectrics, and Frequency Control*, 36(5): 540-548 (1989). The term waveform synthesis, at least in one or more embodiments herein used to provide imaging, refers to one or more processes of using an array driven by arbitrary waveforms to realize specific waveforms at specific control points with each synthesized waveform, in principle, completely independent of all the others. For example, the actual level of independence or orthogonality between the waveforms depends on the available bandwidth and the selection of the control points (e.g., one cannot achieve two independent waveforms at two closely spaced waveforms when the spacing is smaller than the width of the point spread function of the array at that location). The synthesis algorithm defined in FIG. 5 is one exemplary approach to waveform synthesis.

In more detail with reference to FIG. 3, waveform generation 85 may be implemented by an algorithm that begins by selecting $N_F$ frequencies from the available transducer apparatus bandwidth (block 84) (e.g., such frequencies or pulse carrier frequencies may be selected at random), or i.e., $f_n \in [f_{min}, f_{max}]$, $n=1,2,\ldots,N_F$ Using a priori defined values of SNR and CR (e.g., desired SNR value, expected CR value as shown in block 86, for example, based on other information, such as other image data, knowledge of the target such as the type of target, etc.), each frequency component may be a carrier of a finite-bandwidth pulse (e.g., a raised cosine pulse) of duration $T_n$; which defines the time-bandwidth (TBW product), where:

$T_n$, $n=1,2 \ldots N_F$,

The finite-bandwidth pulse of duration $T_n$,

For each frequency component, a multiple-focus optimization problem may be solved using a synthesis algorithm which results in an excitation vector of the array elements, $u(f_n)$. For each array element, i, the component of the excitation vector, $\{u_i(f_n)\}_{i=1}^{N_c}$, represents a frequency component, $f_n$, of the coded waveform driving the transducer elements. Therefore, the waveform synthesis problem amounts to solving the multiple-focus synthesis problem at all frequencies of interest and combining their corresponding finite-bandwidth pulses (e.g., raised cosine waveforms) with appropriate weighting taking the system (e.g., transducer apparatus) bandwidth into account. One exemplary algorithm of such synthesis is provided in Algorithm 1 in FIG. 5 provided with respect to vessel Wall CPs (e.g., control points on a vessel wall), Lumen CPs (e.g., control points in the lumen defined by a vessel wall), and Critical CPs (e.g., critical control points placed at certain locations, such as, for example, those locations where the transmit energy is to be minimized (e.g., ribs, etc.). For example, the wavefront synthesis approach described in at least one embodiment herein may employ a finite number of randomly selected single frequency components (e.g., carriers for pulses) within the transducer bandwidth. Each carrier, for example, has a finite bandwidth specified by its duration and modulating pulse, e.g., a raised cosine. The carrier phase and amplitude can be adjusted, in addition to the delay, to achieve a specified SNR and CR values for a given selection of CPs in the region of interest. This approach is distinct from other previously proposed waveform design methods by at least its adaptive nature and randomness of the carriers.

Figure 17A:
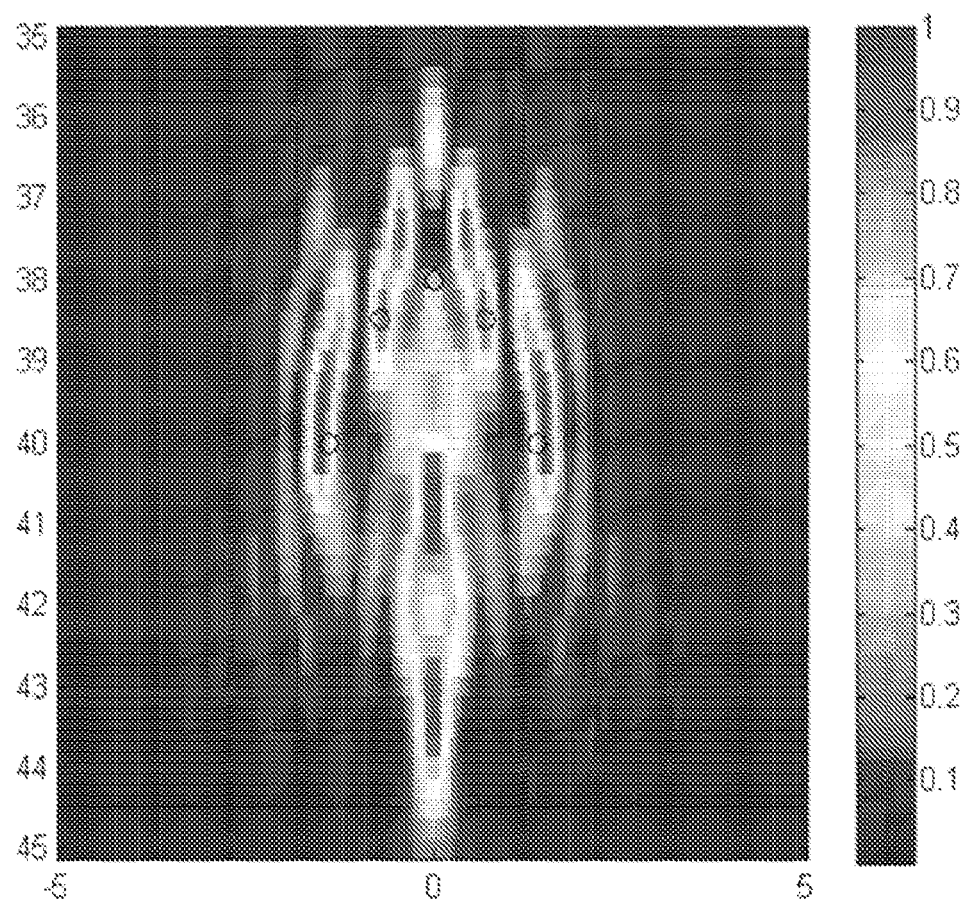
FIGS. 17A-B provide an illustration of a single frequency five-focus pattern synthesis and an illustration of a five-focus pattern resulting from wavefront synthesis of five independent codes at the same five control points, respectively.
Figure 17B:
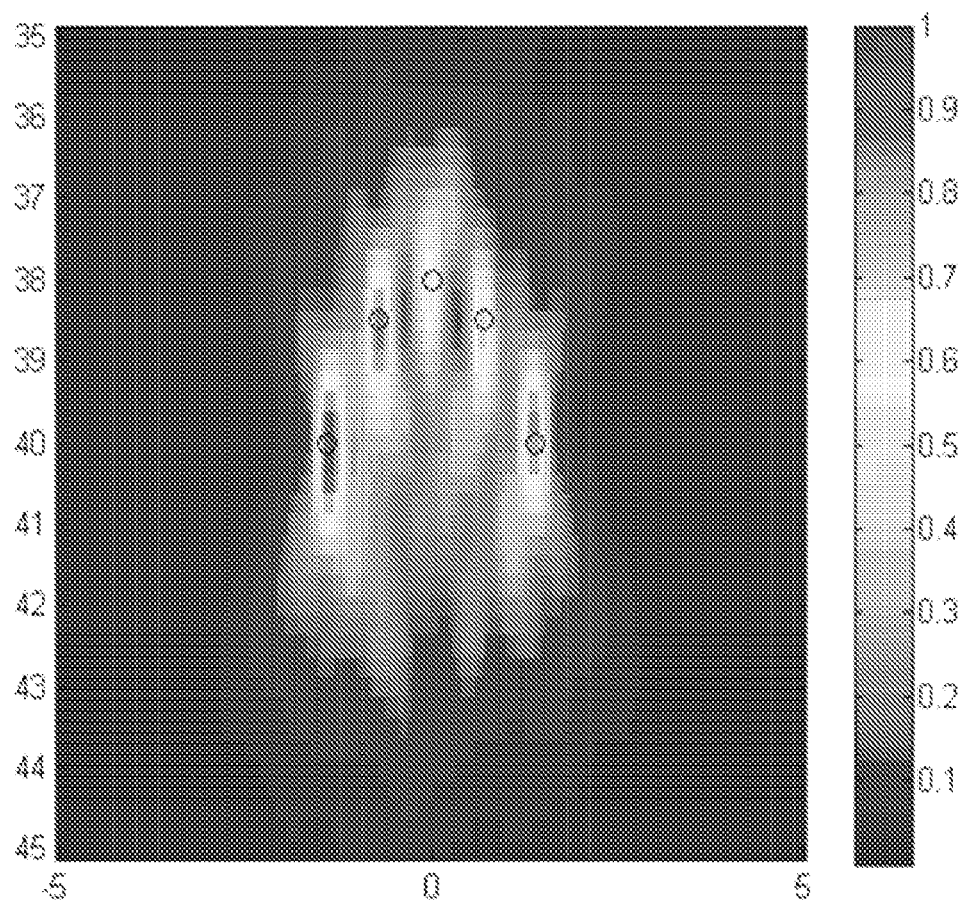

Once the waveform synthesis is completed, the element waveforms may be downloaded to a driver memory and used to drive the array of transducer elements in pulsed mode in substantially the same way as conventional ultrasound systems, except that different transducer elements of the array are driven by different waveforms. This may be performed without the need for any beamforming since beamforming is included in the selection of the CPs. Beamforming is included in the selection of CPs due to the fact that the waveform synthesis process, by producing specified waveforms at any CPs, automatically adjusts the delays, phase shifts, and amplitudes of the single-frequency components to achieve the necessary focusing at the CPs. For example, with reference to FIGS. 17A-B, take an example that includes five control points. A five focus wavefront may be used, with each of the five control points being associated with a desired waveform that was synthesized by a basis set of narrowband functions (e.g., almost like a single frequency waveform). FIG. 17A illustrates the single frequency five-focus pattern synthesis, which is one step of the algorithm in FIG. 5. The pattern in FIG. 17B represents a five-focus pattern resulting from the wavefront synthesis of five independent codes at the same five control points.

In other words, after the waveform synthesis is completed, ultrasound energy is delivered in pulsed mode to the region of interest using the plurality of ultrasound transducer elements in response to waveforms generated for each of the plurality of ultrasound transducer elements. As shown in FIG. 3, a synthesized coded multi-focus pattern of ultrasound energy is provided (e.g., delivered or otherwise transmitted to) at the CPs. In the embodiment of a blood vessel as shown in FIG. 4, the multi-focus pattern of ultrasound energy is provided at the CPs around the vessel wall 42 and within the lumen 45.

In response to the delivery of ultrasound energy to the region of interest, pulse echo data is received at each ultrasound transducer element of a plurality of ultrasound transducer elements for use in generating an image based thereon. In other words, pulse-echo imaging is performed based on the pulse echo data received by the plurality of transducer elements (block 90). For example, various processes may be used to separate pulse echo components received from the control points associated with identifiable portions within the region of interest (e.g., pulse echo components received from the first portion of the control points associated with the first identifiable portion of the region of interest may be separated from the received pulse echo data, pulse echo components received from the second portion of the control points associated with the second identifiable portion of the region of interest may be separated from the received pulse echo data, etc.)

For example, received pulse echo data may be beamformed in any suitable manner and filtering (e.g., pre-beamforming and/or post-beamforming) may be applied in any suitable manner to separate the pulse echo components from individual CPs (and their vicinities). Such pre-beamforming and/or post-beamforming may be DFT based beamforming. Further, for example, depending on $N_f$ (i.e., the number of distinct frequencies used in synthesizing the driving waveforms), the received pulse echo data can be filtered using bandpass filters centered at $f_n$ prior to beamforming. Further, for example, alternately, beamformed data can be processed by this type of filter bank. Regardless, any suitable processing may be used that provides the objective of estimating the spectral components of the echoes from each of the control points. Further, in one or more embodiments, pulse-compression techniques, such as inverse or matched filtering can be applied to at this stage. The energy of the echoes from the CPs can be used to compute a contrast ratio between identifiable portions in the region of interest (block 92). For example, a contrast ratio may be determined between the first and second identifiable portions based on the pulse echo components received from the first portion of the control points associated with the first identifiable portion (e.g., vessel wall) of the region of interest and the pulse echo components received from the second portion of the control points associated with the second identifiable portion (e.g., lumen) of the region of interest. Likewise, a contrast ratio may be determined between first and third identifiable portions based on the pulse echo components received from the first portion of the control points associated with the first identifiable portion (e.g., vessel wall) of the region of interest and the pulse echo components received from the second portion of the control points associated with the second identifiable portion (e.g., tissue about the vessel wall) of the region of interest.

For example, when contrast ratios for blood vessel structure, CR may be defined as:

$$CR = \frac{\sum_{k=1}^{N_W} E_k^W}{\sum_{k=1}^{N_L} E_k^L}$$

where E denotes the energy from a control point and the subscripts W and L denote wall and lumen, respectively.

Similarly, the energy of the echoes from the CPs and one or more reference portions of the region of interest can be used to compute a signal-to-noise ratio (block 96). For example, a signal-to-noise ratio may be determined based on pulse echo components received from a reference portion of the region of interest and pulse echo components received from the control points associated with one or more identifiable portions of the region of interest (e.g., control points associated with the first identifiable portion such as a vessel wall, control points associated with the second identifiable portion of the region of interest such as the lumen, etc.).

For example, signal-to-noise ratio for blood vessel structure, SNR, may be defined as:

$$= \frac{\sum_{k=1}^{N_W} E_k^W + \sum_{k=1}^{N_L} E_k^L}{\sum_{k=1}^{N_R} E_k^R},$$

where the subscript R denotes a reference region which characterizes the noise, e.g. anechoic region.

As shown in FIG. 3, the waveform generated for one or more of the plurality of ultrasound transducer elements (e.g., generated using waveform synthesis of the block 88) may be modified based on at least one of the calculated contrast ratio and the signal-to-noise ratio (e.g., as shown by the decision blocks 92 and 96 along with respective loops via blocks 94 and 97). For example, the method 80 may compare at least a calculated signal-to-noise ratio to a threshold value and modify the waveform synthesis process for generating the waveform to be applied to the one or more plurality of ultrasound transducer elements based on the comparison. Likewise, for example, the method 80 may compare at least a calculated contrast ratio to a threshold value and modify the waveform synthesis process for generating the waveform to be applied to the one or more plurality of ultrasound transducer elements based on the comparison.

With further reference to FIG. 3, for example, the calculated CR and SNR quantities may be compared to specified threshold values $\gamma_c$ and $\gamma_s$ decide the manner in which the frequency components of the transmit waveform for driving the plurality of ultrasound transducer elements should be modified. For example, if the calculated CR is below its threshold (block 92), the time-bandwidth (TBW) product may be increased (block 94) by increasing the gain at frequencies at the edge of the transducer passband (e.g., using a form of inverse filtering). If the calculated CR is not below its threshold (block 92), then the calculated SNR may be compared to its threshold (block 96). If the SNR is higher than the threshold (block 96), then the adaptive imaging procedure has converged and data may be acquired for image formation and reconstruction in the target region of interest (block 98). If the SNR is not higher than the threshold (block 96), then spectral matching between the transmit waveforms and the echo components is emphasized (block 97) (e.g., using a form of matched filtering). This amounts to reducing the TBW product. Therefore, the two tests (e.g., using calculated SNR and CR) produce two arms of balancing the spectral components of the transmit waveforms to maximize the contrast between the vessel wall and the lumen while maximizing the SNR from the whole region of interest.

In one or more embodiments, various actions may be taken to modify the waveform synthesis process. For example, such modifications may include adjusting gain at frequencies of the one or more frequencies located in more locations within the transducer apparatus bandwidth, adjusting one or more pulse parameters including at least one of pulse duration, pulse shape, pulse amplitude, and pulse phase to adjust time bandwidth product, etc.

Image formation is generally implemented using beamforming techniques which amount to back propagation in a homogeneous medium. This may also include an aberration correction that still produces an image of the reflectivity map of an inhomogeneous object. The adaptive imaging described herein may also perform image formation in the same sense as conventional image formation methods (e.g., producing an image of the reflectivity map of an object), but differs from these methods in that it modifies the transmit waveforms to maximize both SNR and CR in a given ROI.

This adaptive image formation may be followed by a reconstructive process that utilizes single-frequency components (e.g., extracted using a running DFT processor for each frequency). Any number of image reconstruction algorithms may be used. For example, the Born or Rytov algorithms can be used depending on the nature of the heterogeneity W. C. Chew, Waves and Fields in Inhomogeneous Media, Van Nostrad Reinhold, New York (1990). Further, a higher order distorted Born approximation can be used O. Haddadin and E. S. Ebbini, "Ultrasonic Focusing through Inhomogeneous Media by Application of the Inverse Scattering Problem," J. Acoustical Society of America, vol. 104, no. 1, pp. 313-325 (1990). For example, these algorithms may be implemented in matrix form and may best be implemented on a GPU or multi-core CPU. Further, for example, it can even be implemented on clusters in the cloud. In one or more embodiments, the matrix operators may be simplified and implemented in terms of the DFT.

Figure 15:
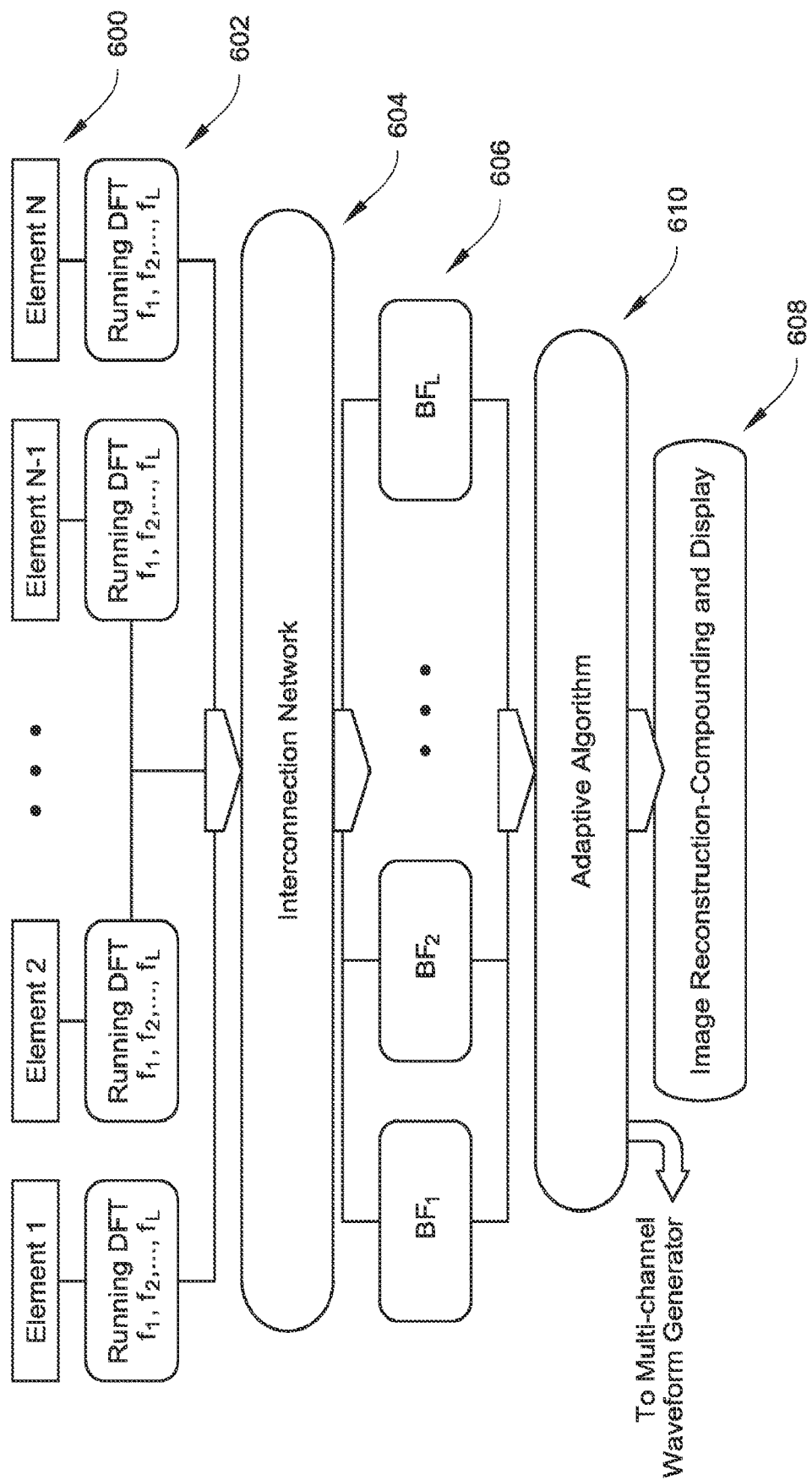
FIG. 15 provides an illustration for implementing at least a portion of the image system with use of running DFT before beamforming, although running it post beamforming may also be possible.
Figure 16:
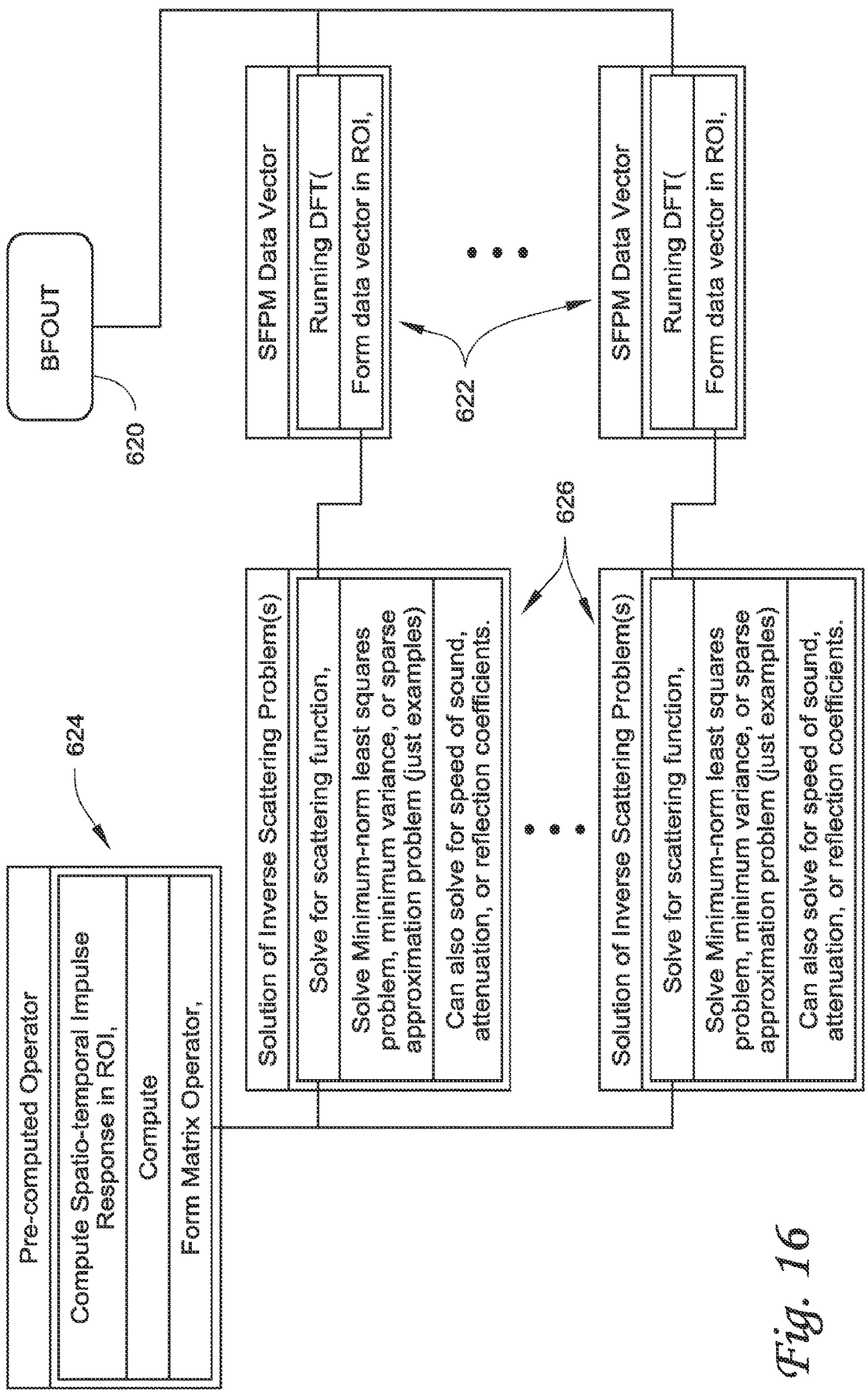
FIG. 16 provides an illustration for implementing image reconstruction that is applied in conjunction with post beamforming extraction of the SFPM data vector(s) after beamforming.

FIGS. 15-16 show one or more embodiments usable for image reconstruction. Such embodiments are just examples, but a variety of similar scenarios can be achieved by proper synthesis of the coded wavefront to simplify the reconstruction operator. As shown therein, a plurality of transducer elements 600 are used to capture the pulse echo data and a running DFT computational block 602 at a frequency of interest for each receiving element may be used to extract single-frequency components from such pulse echo data. Beamforming may be applied, such as by a frequency-domain beamforming network 606 (e.g., DFT and beamforming may both be implemented on an FPGA). The interconnection network 604 may be implemented in software under program control using a programming language suitable for a multiple core GPU, e.g., CUDA or OpenCL. The interconnection network 604 may also be based on the use of physical memory for buffering running DFT outputs before beamforming. This physical memory may be realized inside an FPGA using distributed memory or block memory features available on many FPGA. Alternatively, interconnection network 604 may be implemented outside the FPGA with appropriate bus architecture and address control circuitry.

Image reconstruction 608 may be performed as described herein (e.g., to provide imaging of the scattering function or other quantitative property of the ROI). Further, an adaptive algorithm 610 may be used to provide enhanced image formation as described herein, for example, with reference to FIG. 5. For example, to provide image reconstruction of scattering function or other quantitative property of the ROI (e.g., such as, speed of sound, attenuation, or reflection coefficients), the beamformed output 620 from the beamforming network 606 may be applied to an image reconstruction process as shown in FIG. 16.

As shown in FIG. 16, a matrix operator is pre-computed (see block 624) and used in solving inverse scattering problems 626 (see O. Haddadin and E. S. Ebbini, "Imaging Strongly Scattering Media Using Multiple-frequency Distorted Born Iterative Method," *IEEE Trans. UFFC*, vol. 5, no. 6, pp. 1485-1496, 1998). In the context of linear array imaging illustrated in FIG. 9, the running DFT (blocks 622) computes a SFPM vector that defines the receive data from one sub-aperture (associated with each image line). The distorted Born iterative method (DBIM) may be used to solve for the scattering function at every pixel using the pre-computed single-frequency operators associated with the sub-aperture associated with the given A-line.

The adaptive imaging approach described herein is not limited for use in imaging vascular structure. As indicated herein adaptive ultrasound has the potential to perform imaging and therapy in complex media using is a new paradigm which represents a unified approach to imaging and therapy using arbitrary waveform generation (e.g., as opposed to being hampered by the use of conventional CW or pulsed excitations on the therapy and imaging sides). In principle, given the target size and depth together with a general understanding of its surroundings (e.g. bone, ligaments, etc.) a DMUA with relatively small number of elements to produce high quality focusing (for imaging and therapy) within the target while avoiding the critical structures in the path of the beams may be designed. Therefore, lower back pain, stroke, cardiac ablation, renal denervation and any number of applications where precise ablation is sought can be exquisitely performed using this adaptive imaging described herein.

Figure 12:
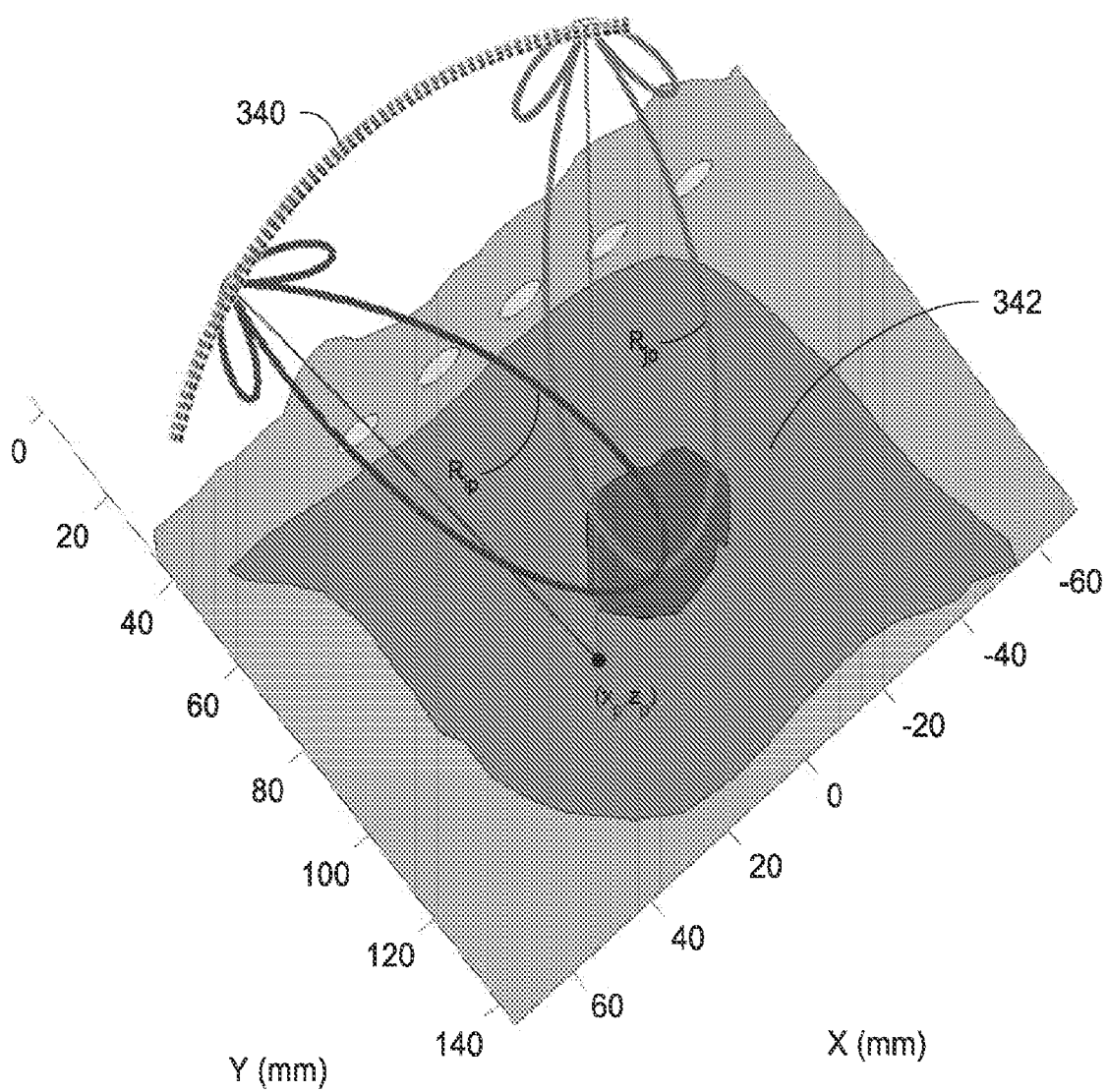
FIGS. 12-14 are illustrations for use in describing the extension of adaptive imaging to applications other than vascular applications.

Such an approach can be extended to imaging more complex media such as shown in FIG. 12. FIG. 12 shows a DMUA 340 targeting of a liver tumor 342 in a transthoracic imaging/therapy scenario. Conventional synthetic aperture (SA) imaging as described in the article, Ebbini et al., "Dual-mode ultrasound phased arrays for image-guided surgery," *Ultrasound Imaging*, vol. 28, pp. 201-220 (2006), can be used to obtain an image of the medium suitable for adaptive refocusing as was illustrated in the article, Ballard, et al., "Adaptive transthoracic refocusing of dual-mode ultrasound arrays," *IEEE Trans Biomed Eng*, vol. 57, no. 1, pp. 93-1-2 (January 2010).

In SA mode, the RF data from an image pixel at $P(x_p, z_p)$ in a medium with uniform speed of sound, c, is computed by:

$$I(x_p, z_p) = \sum_{i=1}^{64} \sum_{j=1}^{64} A_i \cdot B_j \cdot s_{i,j}\left(\frac{R_{ip} + R_{jp}}{c}\right),$$

where $A_i$ and $B_j$ are, respectively, the transmit and receive apodization weights, $R_{ip}$ and $R_{jp}$ are, respectively, the distances from the transmitting and receiving elements to the image pixel P, and $s_{i,j}(t)$ is the echo received by element j when transmitting with element i. Other imaging scenarios can be performed by specializing the image formation as described in the article, T. Misardis and J. A. Jensen, "Use of modulated excitation signals in medical ultrasound. Part I: basic concepts and expected benefits," *IEEE Trans. Ultrason., Ferroelect., Freq. Contr.*, vol. 52, no. 2, pp. 177-191 (February 2005).

SA imaging can be implemented in real time in an ultrasound imaging system. Furthermore, taking the directivity patterns into account can improve the contrast by rejecting echo data from low SNR pixels in the target region as described in the article, Y. Wan and E. S. Ebbini, "Imaging with concave large-aperture therapeutic ultrasound arrays as in conventional synthetic-aperture beamforming," *IEEE Trans Ultrason Ferroelectr Freq Control*, vol. 55, no. 8, pp. 1705-1718 (August 2008). For example, the pixel at $(x_p, z_p)$ in FIG. 12 is shown outside the target tumor (darkest region) with lines from the centers of a pair of transmitting and receiving elements defining propagation delays for the SA imaging. The directivity functions for the transmit-receive pair are also shown. The product of the transmit-receive directivity patterns at pixel $(x_p, z_p)$ for a given transmit-receive pair is a measure of the SNR. The SA beamforming can be modified to account for this variation in SNR resulting in an improved contrast at the expense of reducing the field of view of a concave array like the one shown in FIG. 12.

A heterogeneous medium with strong scatterers as shown in FIG. 12 can be approximately imaged using a real-time SA method. Alternatively, a tomographic reconstruction method can be employed, but these methods do not lend themselves to real-time implementation. The adaptive imaging algorithm shown and described herein can be applied with obvious modifications, primarily in the assignment of the CPs. For example, the CPs can be chosen to maximize the SNR within the "hypothesized tumor" or "target" region. This may be considered a generalization of our single-transmit focusing system described in the article, Ebbini et al., "Dual-mode ultrasound phased arrays for image-guided surgery," *Ultrasound Imaging*, vol. 28, pp. 201-220 (2006), and in earlier patent applications, such as U.S. Patent Application Publication No. US2013/0144165 A1, entitled "Dual Mode Ultrasound Transducer (DMUT) System and Method for Controlling Delivery of Ultrasound Therapy" published 6 Jun. 2013. Additional critical points may be placed at the rib locations to minimize exposure to the ribs while maximizing the SNR at the target CPs.

Figure 13:
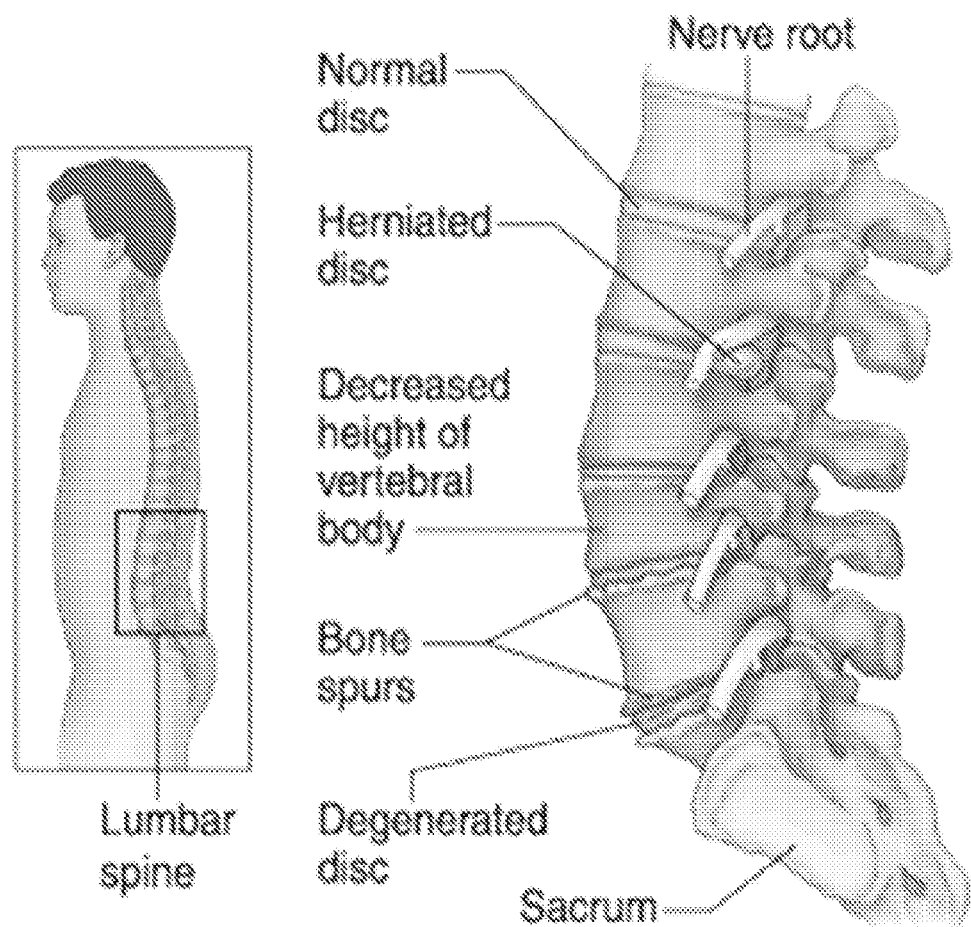
Figure 14:
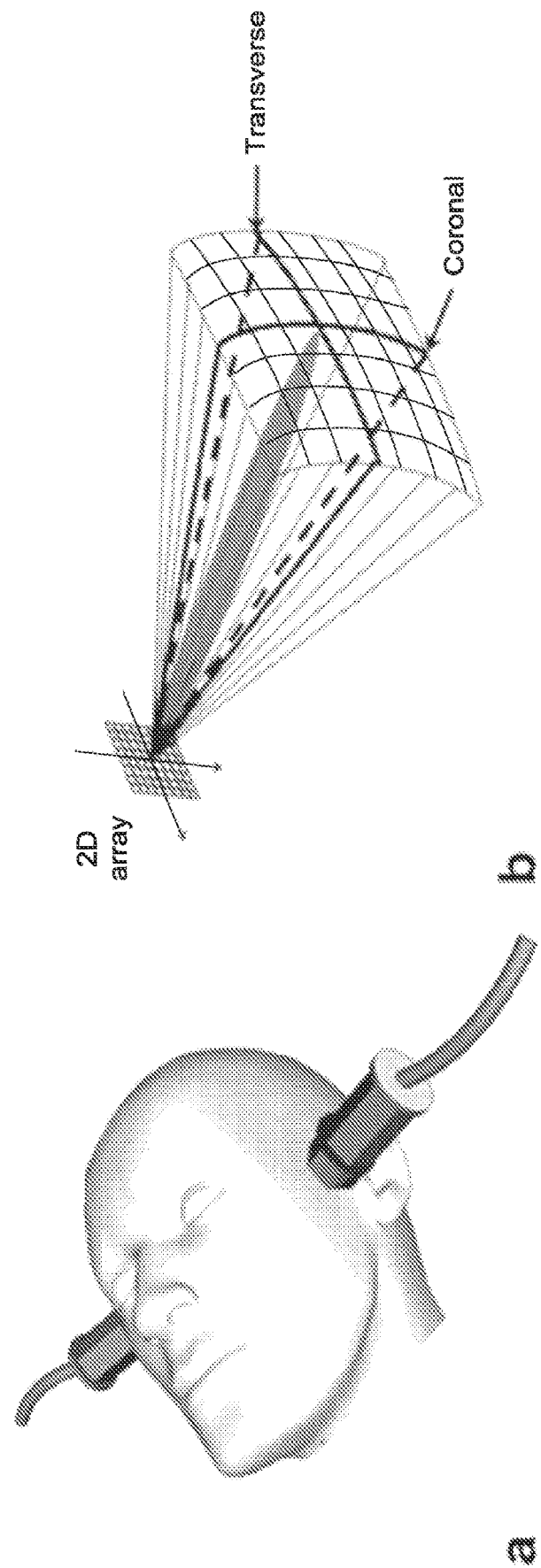

Adaptive imaging can be used for imaging and targeting of complex structures for possible treatment of lower back pain in individuals not responding to medical treatment. Adaptive imaging will allow for maximizing the sensitivity and specificity to echoes from the soft disc tissues as shown in FIG. 13 while suppressing interference from the nearby bone structure. CPs associated with the disc region and echoes from the bone can be defined to perform the necessary optimization problem. In this application, it may be possible to image the nerve root associated with a given vertebra for targeting or avoidance as indicated by the appropriate protocol.

Adaptive imaging can also be applied in trans-skull imaging and targeting of brain structures, e.g. sonothrombolysis for acute ischemic stroke. The selection of the CPs will be to enhance the sensitivity and specificity of Doppler signals from the target (e.g., a clot) region. Other applications in the brain include deep brain stimulation and blood-brain barrier opening. FIG. 14A shows stroke imaging such as described in Lindsey et al., "Simultaneous bilateral real-time 3-d transcranial ultrasound imaging at 1 {MHz} through poor acoustic windows," *Ultrasound in Medicine and Biology*, vol. 39, no. 4, pp 721-734 (2013). The approach compromises on the aperture size (small aperture) and frequency of operation (low operating frequencies of 1.2-1.8 MHz). This results in an inevitably low contrast imaging system. Use of adaptive imaging as described herein capable of adjusting the spectral content of the imaging (and therapy) pulses based on real-time feedback to take advantage of more or all possible windows in space (e.g., by using larger apertures) and frequency (e.g., by utilizing all frequency bands with good transmission properties within the operating bandwidth of the DMUA).

By maximizing the time-bandwidth product of the imaging pulses within the target region while insuring maximum transmission through the skull, anatomically useful images may be produced. Only a crude outline of the vessels appears to currently be obtainable with the use of contrast-enhanced ultrasound (e.g., using Definity available from Lantheus Medical Imaging). For example, a DMUA capable of focusing at approximately 7 cm inside the brain from the temporal side utilizing a window with skull thicknesses between 2 mm to 4 mm and operating in the frequency range of 0.6 MHz to 1.6 MHz may be designed. Using the arbitrary waveform generation capabilities of our driver, the SNR at the target may be maximized while maintaining the highest resolution possible.

Figure 6:
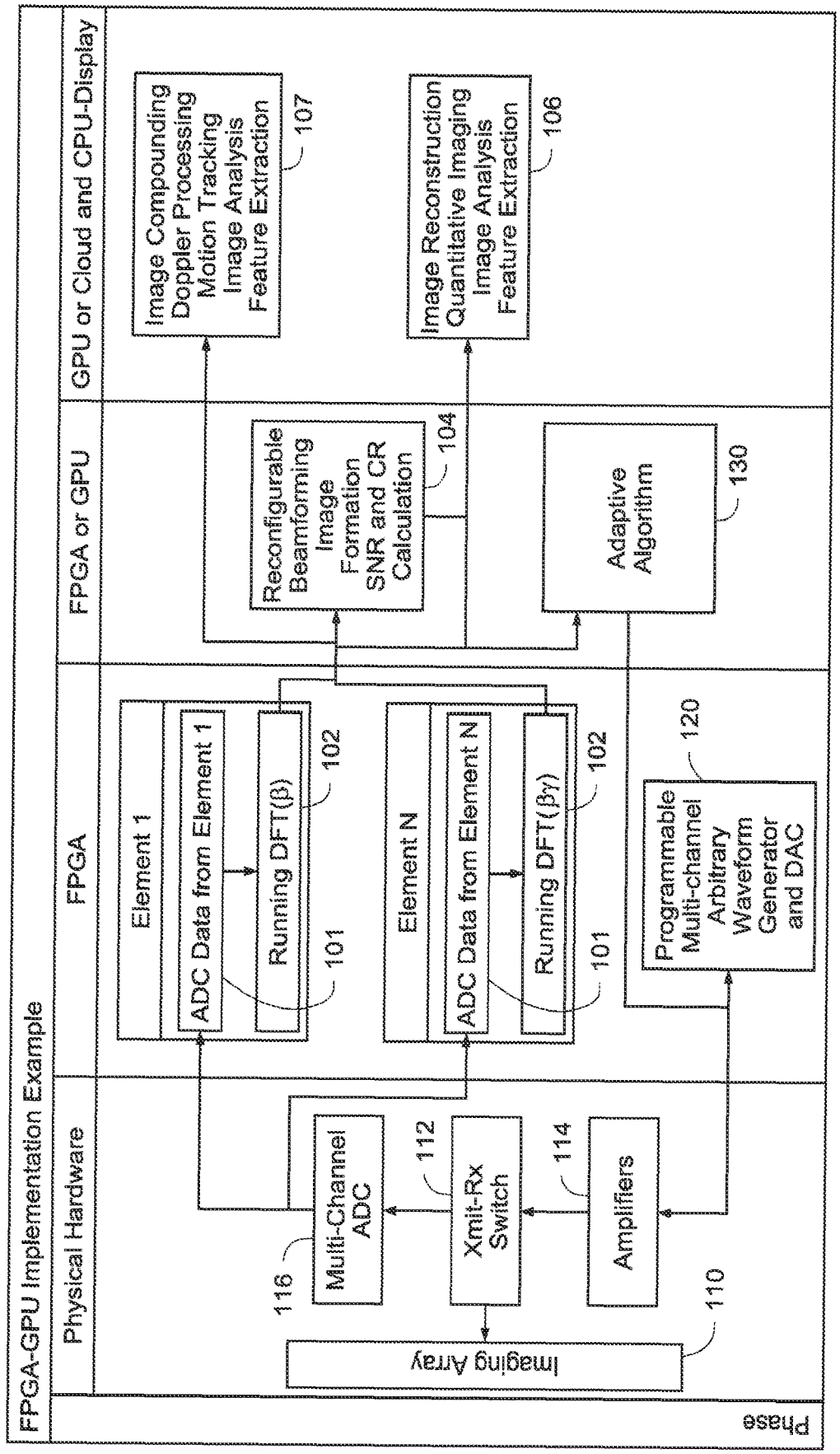
FIG. 6 is a block diagram of one exemplary embodiment that may be used for implementing an imaging system shown generally in FIG. 1.
Figure 7:
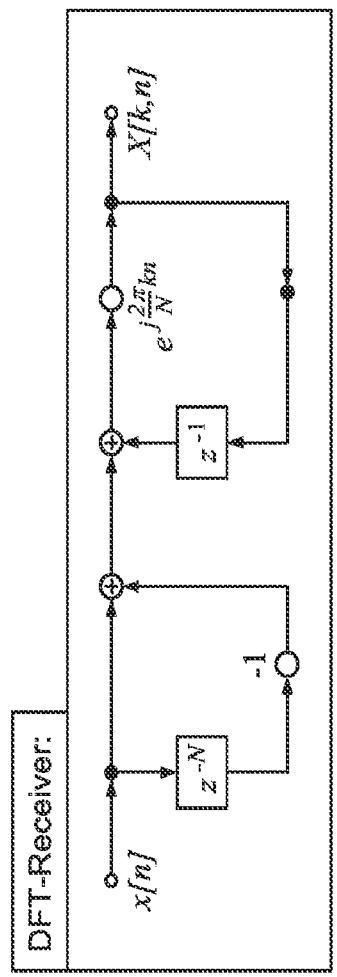
FIG. 7 is a diagram of one exemplary DFT receiver that may be used for implementation of an imaging system such as shown in FIG. 3.

The generation/transmission of ultrasound energy and the receipt/analysis of pulse-echo data may be provided using any ultrasound imaging system (e.g., the imaging system 10 of FIG. 1), although one or more imaging systems may be advantageous over others. In one or more embodiments, the waveform generation and pulse echo data acquisition may be performed by an imaging system 100 such as shown in FIGS. 6 and 7. For example, as shown in FIG. 6, the imaging system 100 may be used to generate waveforms for driving a plurality of ultrasound transducer elements, as well as acquire and perform real-time processing of such acquired pulse echo data. The imaging system 100 may include an ultrasound scanner (e.g., a Verasonics Vantage (Verasonics, Redmond, Wash.)) loaded with one or more programs for generating waveforms for driving a plurality of ultrasound transducer elements and acquiring and perform real-time processing of acquired pulse echo data resulting from delivered ultrasound energy (e.g., to provide the adaptive algorithm described herein, to provide for high frame rate pulse-echo data collection, to perform therapy, etc.). The ultrasound scanner may include and/or be modified to include features such as chirp generation, waveform generation such as the synthesis and adaptive algorithms described herein, image reconstruction as described herein, data collection, and data transfer capabilities.

FIGS. 6-7 (which may also implement the embodiments described with reference to FIGS. 15-16) provide one exemplary FPGA-GPU implementation for carrying out the adaptive algorithm described herein for image formation and image reconstruction as described herein. For example, in one or more embodiments, the implementation may include physical hardware, and FPGA, GPU, a CPU, and display. Generally, a running DFT 102 (e.g., a running DFT computational block at a frequency of interest for each receiving element) followed by a frequency-domain beamforming network 104 may be used in providing the functionality described herein (e.g., both of which may be implemented on the FPGA). Image reconstruction of the scattering function or other quantitative property of the ROI (e.g., block 106) may be performed after the single-frequency image formation (e.g., which may be performed on a graphical processing unit (GPU)). Alternatively (not shown), a DFT processor may be deployed after beamforming and before the reconstruction block. In this case, the DFT and the reconstruction block may be performed on a GPU. In general, all three stages are computational stages and can be implemented in FPGA, GPU, multi-core CPUs or any appropriate processing unit(s).

FPGA's are well suited for the generation of multiple arbitrary waveforms with exquisite timing precision. One exemplary and flexible solution for implementation of synthesis and generation is to provide a sufficiently deep memory for each channel with sufficient width (e.g., for accuracy). The depth of memory allows for controlling the time-bandwidth product (TBW) of the generated waveforms. The waveform synthesis can be performed on the CPU or the GPU, with the latter offering the advantage of parallelization. For example, the waveform synthesis approach described herein may be based on finite number of distinct, randomly-selected frequency components within the transducer bandwidth. A GPU can be programmed so that the synthesis described in FIG. 5 can be performed simultaneously on all frequency components to accelerate the adaptation.

As shown in the exemplary implementation embodiment of FIG. 6, physical hardware of the system may be used to transmit pulses and collect pulse echo data. For example, an imaging array 110 may be controlled using a transmit/receive switch 112 to transmit pulses or receive pulse echo information. On the receive side, a multi-channel analog to digital (ADC) convertor 116 may be used to convert the transducer signal for receipt in channel circuitry 101 such that it may be operated upon by running DFT 102. transmit pulses or receive pulse echo information (e.g., the running DFT may include an implementation as shown in FIG. 7). On the transmit side, a programmable multi-channel arbitrary waveform generator and digital to analog (DAC) convertor 120 may be used to generate waveforms for driving the transducer elements of the imaging array 110 to transmit pulses (e.g., the signal from the waveform generator 120 being applied to the transducer elements via an amplifier 114 and under control of switch 112). The programmable multi-channel arbitrary waveform generator and digital to analog (DAC) convertor 120 uses the adaptive algorithm 130 (e.g., such as that shown in FIG. 5) to modify the waveforms being generated based on signal to noise ratio and contrast ratio (e.g., of control points) to enhance image formation (e.g., see block 104 which is generally representative of not only reconfigurable beamforming, but also provides image formation (e.g., formation of an image based on reflectivity; a reflectivity map image), and calculation of contrast ratio and signal to noise ratio as described herein.

Further, as shown in FIG. 6, various other types of functionality may be implemented using the GPU and Cloud Computing together with the CPU-Display. For example, other image processing 107, such as image compounding (e.g., use of more than one single frequency image to provide a compounded image), Doppler processing (e.g., tracking small changes in the carrier), motion tracking (e.g., by evaluating the phase of the carrier), image analysis (e.g., separation of specular reflections from speckle components and recognition of structures like vessel walls), and feature extraction (e.g., identifying resonances that may reveal sub-resolution structures like layers of a vessel wall) may be performed.

Further, for example, other image processing 106, such as image reconstruction as described herein, quantitative imaging (e.g., speed of sound, attenuation, reflection coefficient from inverse scattering), motion tracking (e.g., in reconstructed image space, which is expected to have sharper demarcation between tissue structure due to its speckle-free nature), image analysis (e.g., object identification and parameter estimation for computer-aided diagnostics), and feature extraction (e.g., lipid composition of a plaque within the vessel wall, calcification within the plaque, etc.) may be performed.

Still further, in one embodiment, high intensity focused ultrasound (HIFU) is also possible (e.g., for generating ultrasound for treatment or subtherapeutic mechanical and/or thermal effects). For example, a field-programmable gate array (FPGA) may be dedicated for a HIFU source and synchronized frame trigger generation. For example, the HIFU generator may be silenced while pulse-echo imaging is active.

In other words, in one or more embodiments, a system for imaging (e.g., vascular imaging) is provided herein that includes one or more ultrasound transducers (e.g., wherein the one or more transducers are configured to deliver ultrasound energy to a vascular region resulting in pulse-echo data therefrom) and processing apparatus (e.g., including one or more programs executable by one or more processors of the system to perform one or more functions thereof and as described herein, such as adaptive waveform generation, image formation, image reconstruction, etc.).

In other words, the processing apparatus (e.g., FPGA, GPU, CPU, Cloud computing, etc.) may be configured (e.g., operate under control of one or more programs) to, for example, allow definition of a region of interest (e.g., allow a user to define a region of interest in subject using ultrasound imaging), allow definition of a plurality of control points such as described herein, control waveform generation for driving a plurality of ultrasound transducer elements (e.g., of an array of elements), control delivery of ultrasound energy (e.g., in pulse mode) to the region of interest, control the capture of pulse-echo data from the region of interest (e.g., from the control points), separate pulse echo components received from one or more control points associated with corresponding identifiable portions of the region of interest; determining contrast ratios and signal-to-noise ratios for use in modifying the waveform generation, and controlling the modification of waveform generation based on one or more imaging performance characteristics, such as contrast ratio and signal-to-noise ratio.

Further, for example, processing apparatus may be configured to separate, from pulse echo data received, ultrasound energy corresponding to a single frequency and reconstructing an image representative of the more properties in the region of interest from the separated pulse echo data corresponding to a single frequency. Further, processing apparatus may be configured to separate, from the pulse echo data received, one or more additional portions thereof received corresponding to one or more additional single frequencies for use in reconstructing an image representative of one or more properties in the region of interest (e.g., such additional reconstructed images corresponding to multiple frequencies may be combined).

Figure 8:
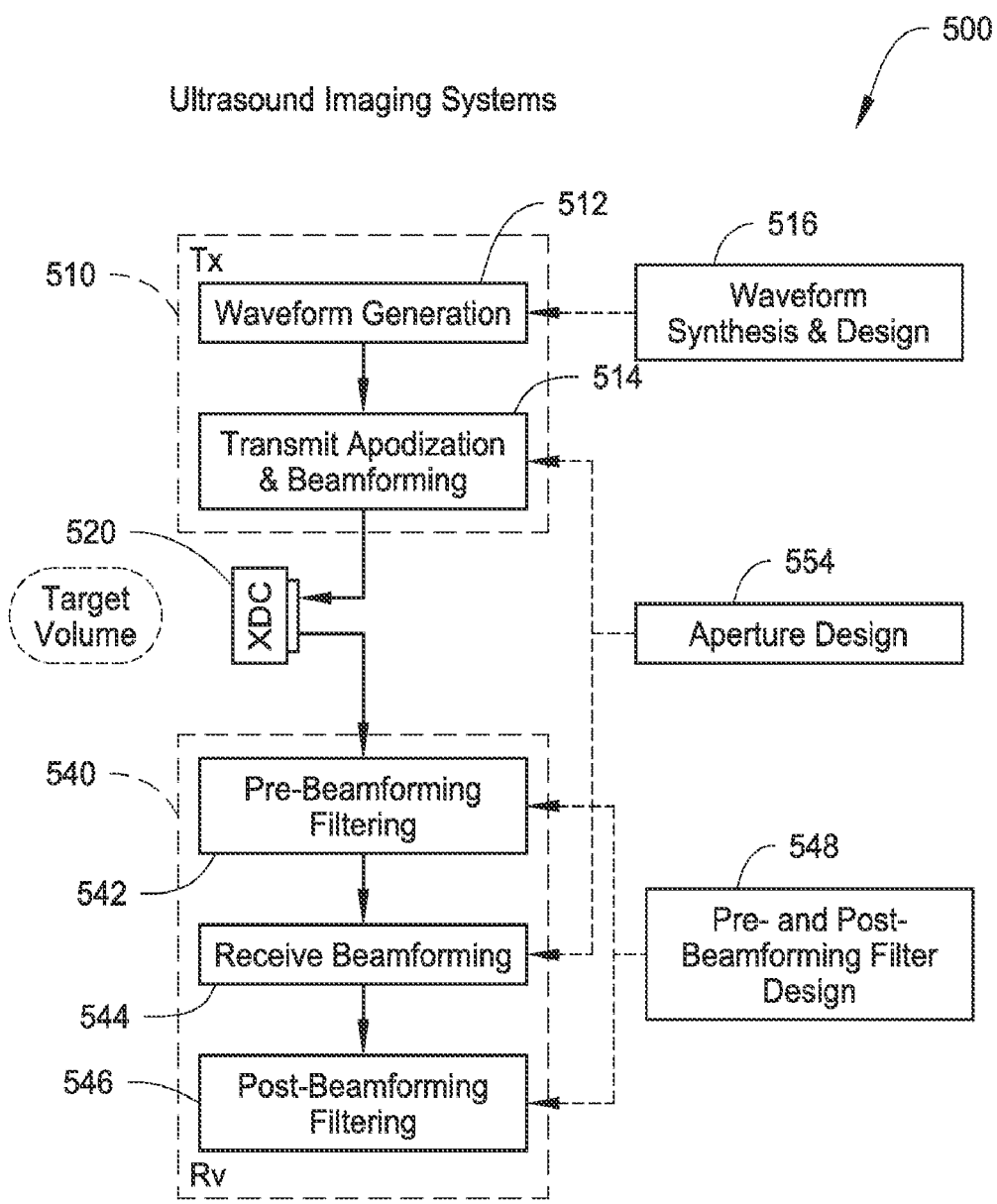
FIG. 8 is a block diagram of another exemplary embodiment of an imaging system shown generally in FIG. 1.

Still further, another exemplary ultrasound imaging system 500 which may be configured to implement adaptive imaging as described herein may be represented by the block diagram shown in FIG. 8. The system 500 may include transmitter apparatus 510 and receiver apparatus 540. For example, transmitter apparatus 510 may be configured to generate arbitrary waveforms (block 512) for driving each element of the transducer array 520 and to perform apodization of the waveform (e.g., changing the shape thereof) and/or and beamforming of the transmit waveforms to various degrees of focusing and steering (e.g., including the capability of providing no beamforming) (block 514). Such waveform generation is based on waveform synthesis and design 516 (e.g., such waveform generation for adaptive imaging is based on waveform synthesis algorithms designed for a particular application, such as vascular imaging).

For example, receiver apparatus 540 may be configured to receive pulse echo data from the plurality of transducer elements of the array 520 and perform pre-beamforming filtering (block 542), receive beamforming (block 544), and post-beamforming filtering (block 546). For example, the system 500 may be configured to perform various levels of beamforming of the received element pulse echo data, which assumed to be available in digital form through sampling and A/D conversion of the received waveforms. A reconfigurable receiver chain may allow for pre-beamforming filtering and post-beamforming filtering. Such beamforming filtering may be based on a beamforming filter design 548 for a particular application (e.g., such beamforming filter design for adaptive imaging may be based on algorithms designed for a particular application, such as vascular imaging). Further, transmit apodization and beamforming (block 514) and receive beamforming (block 544) for a particular application may be based on an aperture design 554 (e.g., an SA design, etc.).

A configured system 500 having such features may take advantage of various synthesis algorithms described below (e.g., the Ultrasound Imaging and Signal Processing Laboratory (UISPL) is believed to have successfully implemented a system that has nearly all the features assumed by the transmit-receive flow shown in FIG. 8). As such, existing ultrasound systems may be adapted to operate as described herein; for example, carry out algorithms described herein, such as with use of digital signal processing techniques (e.g., hardware and software).

The following subsections illustrate several aspects of the system architecture shown in FIG. 8. A brief description of an exemplary one-dimensional (1D) filter design usable with adaptive imaging described herein is given in Section A. A brief description of different exemplary approaches to coded excitation in ultrasound imaging which may be used with the other features described herein is provided in Section B. Such material is meant to provide an example of the operator design and coded excitation for the 1D case. Generalization to the 2D case, in the context of linear array imaging, is given in the article, Y. Wan and E. S. Ebbini, "A Post-beamforming 2-D Pseudoinverse Filter for Coarsely Sampled Ultrasound Arrays," *IEEE Trans on Ultrasonics, Ferroelectrics, and Frequency Control*, vol. 56, no. 9, pp. 1888-1902 (2009). Also, this formulation can be modified in a manner to allow for the use of coded waveforms and for the design of coded wavefronts, as illustrated in numerous publications, such as, E. Ebbini, "Optimal transversal filter bank for 3D real-time acoustical imaging," *Signals, Systems and Computers, 1992. 1992 Conference Record of The Twenty-Sixth Asilomar Conference*, vol. 2, pp. 831-835 (1992); Ebbini et al., "A new svd-based optimal inverse filter design for ultrasonic applications," *Ultrasonics Symposium, 1993. Proceedings., IEEE 1993*, vol. 2, pp. 1187-1190 (1993); Shen et al., "An optimal image operator design technique for coded excitation ultrasound imaging system," *Ultrasonics Symposium, 1994. Proceedings., 1994 IEEE*, vol. 3, pp. 1777-1781 (1994); J. Shen and E. Ebbini, "On the design of a transversal filter bank for parallel processing multiple image lines in real-time acoustic imaging," *Acoustics, Speech, and Signal Processing, 1996. ICASSP-96. Conference Proceedings., 1996 IEEE International Conference*, vol. 6, pp. 3109-3112 (1996); J. Shen and E. S. Ebbini, "Real-time 3d pulse-echo ultrasonic imaging with coded-excitation systems," *Image Processing, 1996. Proceedings., International Conference*, vol. 1, pp. 717-720 (1996); E. Ebbini and J. Shen, "Fundamental resolution limits of a coded-excitation system for real-time pulse-echo imaging," *Ultrasonics Symposium, 1997. Proceedings, 1997 IEEE*, vol. 2, pp. 1539-1542 (1997); and E. S. Ebbini, "Region-adaptive motion tracking of speckle imagery," *Proc. IEEE Int. Conference on Acoustics, Speech, and Signal Processing*, pp. 2075-2078 (2000). Waveforms and wavefronts may be designed for nonlinear imaging using waveform and wavefront designs to create favorable conditions for enhancing the nonlinear response from the target region, e.g. with or without contrast agents.

Section A—One-Dimensional Pseudoinverse Filter Design

A 1D pseudoinverse filter was described in J. Shen and E. S. Ebbini, "A new coded-excitation ultrasound imaging system—part I: basic principles," *IEEE Trans. Ultrason., Ferroelect., Freq. Contr.*, vol. 43, no. 1, pp. 131-140 (1996) derived from a system model for a single A-line acquisition using a 1D linear array. A brief explanation of the filter design process is described herein, but defined on a Cartesian grid for the convenience of deriving the proposed 2-Dimensional Pseudoinverse Filter.

System Model

Figure 9:
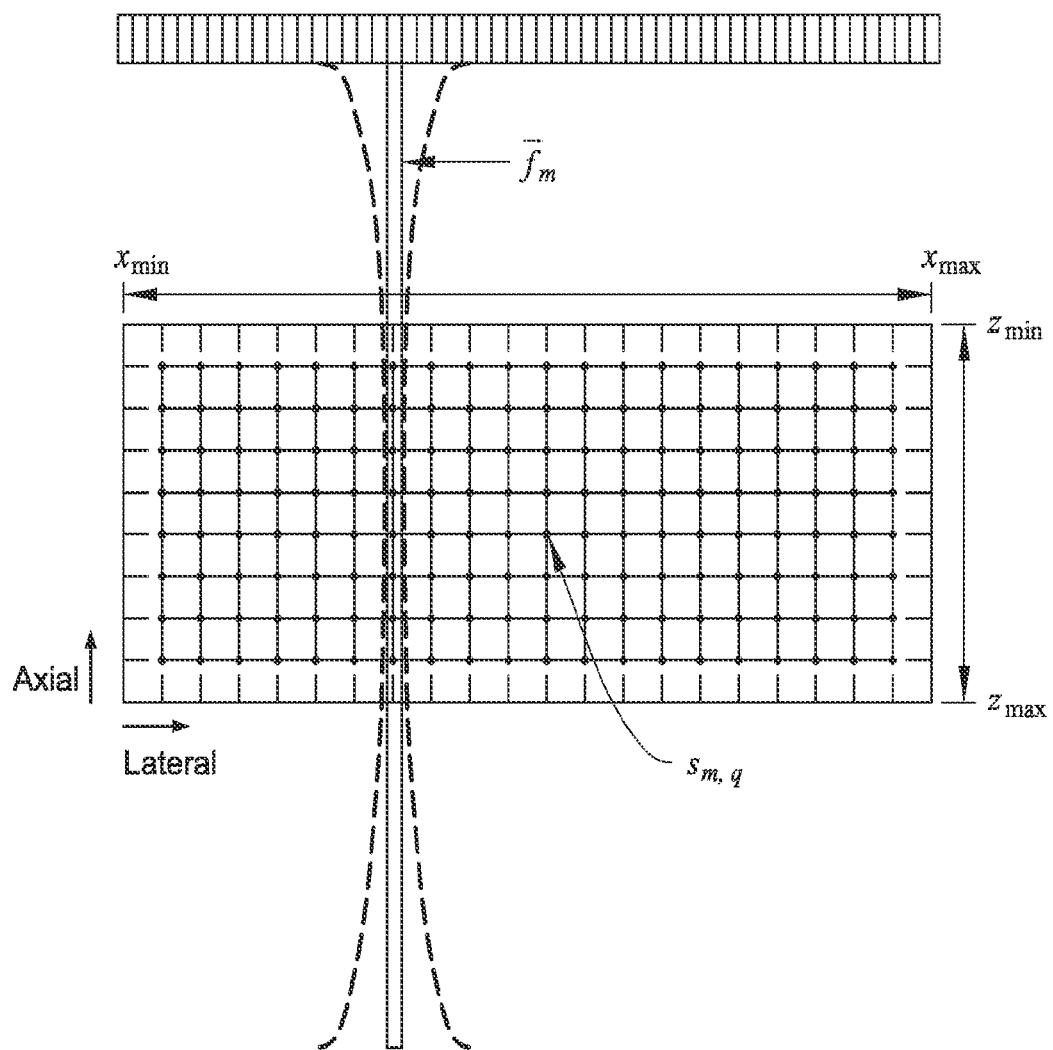
FIGS. 9 and 10 are illustrations for use in describing an exemplary filter designs.

A uniform grid in the imaging field is defined as shown in FIG. 9 and assumes scatterers with random amplitude distribution at the grid points (e.g., a 1D linear array system model where the scattering is assumed to result from scatters with random amplitudes on the Cartesian grid). The number of grid points within a range interval $[z_{min}, \check{z}_{max}]$ in the axial direction, N, determines the axial sampling rate. Similarly, the number of grid points in the lateral direction (or the number of scan lines) within $[z_{min}, \check{z}_{max}]$, M, determines the lateral sampling rate. It is assumed that the grid spacing is small with respect to the correlation cell size of the imaging system in both directions. Note that the grid shown in FIG. 9 represents a subregion of an imaging volume for purposes of reconstructions. Scattering from outside this region must be accounted for by a simulation model for the received echo data.

Define $s_{m,q}$ as the scatterer strength at grid location $(m,q)$ $(m \in [1, M]$, $q \in [1, N])$, $\zeta_m$ as a vector of size $N_i \times 1$ containing amplitudes of scatterers along scan line m $(N_i \gg N)$. Let S be a vector containing all lines of scatterers in the imaging field $(M_i \gg M)$ as $$S = [\ldots \zeta_1^T \zeta_2^T \ldots \zeta_M^T \ldots]^T,$$

where, T denotes matrix/vector transpose. Then the discretized version of the received echo for scan line m in the range interval $[z_{min}, z_{max}]$ can be represented in vector form as $f_m$ of size $N \times 1$ and all the M scan lines can be grouped in F as follows:

$$F = [f_1^T f_2^T \ldots f_M^T]^T.$$

The impulse response of the system at a grid point is the echo from a single unit-strength scatterer positioned at that point. For illustration purposes, it is assumed that the point scatterer is at the center of the specified grid. Then, the generated pulse-echo impulse response at grid point q along line i is denoted as vector $g_{i,q}$ of size $N \times 1$ which contains the discretized samples in time-domain. The pulse-echo impulse responses at the grid points along line i can be grouped as $$G_i = [\ldots g_{i,1} g_{i,2} \ldots g_{i,N} \ldots].$$

Assume $G_0$ is the matrix containing the pulse-echo impulse responses from grid points along the line through the focus and $\{G_{\pm i}\}_{i=1}^{\infty}$ are the matrices containing pulse-echo impulse responses from the grid points along the lines on right/left sides of focus. Typically, $G_i = G_{-i}$ due to the symmetry of the linear array aperture or apodization. Based on the above notations and definitions, the received echo signal from one scan line is obtained by superposition, which can be represented in matrix form:

$$f_m = [\cdots \underbrace{G_{-i} \cdots G_{-1} \ G_0 \ G_1 \cdots G_i}_{\Psi} \cdots ]S,$$

where, $\Psi$ is the spatio-temporal impulse response of the system and each $G_i$ represents the response in a given lateral direction. Therefore, for a single A-line, the sampled beamformer output $f_m$ is related to the scatter distribution S by a discretized propagation operator (matrix) $\Psi$.

Filter Design

If AWGN noise is considered in the system, the system equation for a single A-line is $$f_m = \Psi S + n,$$

where, n contains the AWGN noise term. Thus a minimum-norm least-square estimate of the scatter distribution S can be obtained as $$\hat{s} = \underbrace{\Psi^H (\Psi \Psi^H)^\dagger}_{PIO_{1D}} S,$$

where, the superscripts $^H$, $^\dagger$ represent matrix Hermitian, and generalized inverse operators, respectively and the $PIO_{1D}$ is defined as the 1-dimensional pseudoinverse operator (PIO).

A further reduction of computational complexity can be achieved by using the range-shift invariance (RSI) assumption as described in J. Shen and E. S. Ebbini, "A new coded-excitation ultrasound imaging system—part I: basic principles," *IEEE Trans. Ultrason., Ferroelect., Freq. Contr.*, vol. 43, no. 1, pp. 131-140 (1996); and J. Shen and E. S. Ebbini, "Filter-based coded-excitation system for high-speed ultrasonic imaging," *IEEE Trans. Med. Imag.*, vol. 17, no. 6, pp. 923-934 (1998). The energy and the shape of the impulse responses in the matrices $G_i$ are gradually changing along the axial direction. However, this change is moderate in the vicinity of the focus where one can establish computationally that the impulse responses can be approximated by the time-shifted versions of each other. With this assumption, the matrix $G_i$ can be represented as Toeplitz. In addition, the array beam pattern justifies truncation of the impulse responses from grid points far away from the focus. This implies:

$$g_{i,q} \to 0, q > N_f, N_f$$

is some finite value.

Using the shifted version of $g_{i,c}$, the pulse-echo impulse response at the focus, the RSI approximation version of $G_i$ is a banded Toeplitz matrix of size N×N:

$$G_i = \mathcal{T}(0, \ldots, g_{i,c}(0), g_{i,c}(1), \ldots, g_{i,c}(N_f), \ldots, 0),$$

where $N_f$ is the number of nonzero samples of the impulse response along the ith direction and $\mathcal{T}$ stands for the operator of forming a Toeplitz matrix using a specified sequence. The Toeplitz structure allows diagonalization using DFT matrices:

$$G_i = F_N H_i F_N^{-1},$$

where, $H_i$ is a diagonal matrix and $F_N$ is a DFT matrix of size N:

$$F_N = \begin{pmatrix} 1 & 1 & \cdots & 1 \\ 1 & W_N^{1 \cdot 1} & \cdots & W_N^{1 \cdot (N-1)} \\ \vdots & & \ddots & \vdots \\ 1 & W_N^{(N-1) \cdot 1} & \cdots & W_N^{(N-1)(N-1)} \end{pmatrix},$$

where $$W_N = e^{-j\frac{2\pi}{N}}.$$

With this diagonalization, the $PIO_{1D}$ becomes $$PIO_{1D} = PIOF_1 PIOF_2 \ldots PIOF_N)^T,$$

where, $PIOF_i = F_N Z_i F_N^{-1}$ is the $i^{th}$ filter for obtaining the scatterer distribution along $i^{th}$ lateral direction from received echo $f_m$ and $Z_i$ is a diagonal matrix with diagonal terms defined by $$\{Z_i\}_{k,k} = \frac{H_{i[k,k]}}{\sum_{i=1}^{N} |H_{i[k,k]}|^2}.$$

The above expression defines the $PIO_{1D}$ filter bank in frequency domain. Thus, the estimate of the scatterer distribution is obtained by N filters:

$$\hat{s} = (PIOF_1 f_m, POIF_2 f_m \ldots POIF_N f_m)^T.$$

The RSI assumption followed by DFT operations allows complexity reduction from N×N filters to N filters and leads to the derivation of an illustrating expression of the $PIO_{1D}$ filter as shown in the equation above for $\{Z_i\}_{k,k}$.

This filter bank implementation allows parallel processing of echo data from multiple directions from a single beamforming operation. In principle, the filter bank could be designed to decouple echoes from different directions given the echoes from different directions are uncorrelated. Therefore, more efficiency in decoupling requires the operation in conjunction with multi-modal coded excitation, i.e. several distinct codes are transmitted simultaneously with single receive beamforming of echoes from the region of interest.

Section B—Coded Excitation

It is well known that in conventional pulse-echo ultrasound imaging, there is a trade-off between resolution and penetration under the limit of peak acoustic power. Narrower pulses will have wider bandwidth and better resolution, but suffer lower SNR for less penetration. Using coded waveforms as excitation enables elongated pulses for higher SNR.

Coded Waveforms.

Different coded excitation approaches have been proposed using different codes: PN sequences as described in J. Shen and E. S. Ebbini, "Filter-based coded-excitation system for high-speed ultrasonic imaging," *IEEE Trans. Med. Imag.*, vol. 17, no. 6, pp. 923-934 (1998) and M. O'Donnell and Y. Wang, "Coded excitation for synthetic aperture ultrasound imaging," *IEEE Trans. Ultrason., Ferroelect., Freq. Contr.*, vol. 52, no. 2, pp. 171-176 (February 2005); Golay codes as describe in R. Y. Chiao and X. Hao, "Coded excitation for diagnostic ultrasound: A system developer's perspective," *IEEE Trans. Ultrason., Ferroelect., Freq. Contr.*, vol. 52, no. 2, pp. 160-170 (February 2005); and chirps as described in T. Misaridis and J. A. Jensen, "Use of modulated excitation signals in medical ultrasound. part I: basic concepts and expected benefits," *IEEE Trans. Ultrason., Ferroelea, Freq. Contr.*, vol. 52, no. 2, pp. 177-191 (February 2005).

Coded waveforms can be categorized into 4 groups according to the ambiguity function as indicated in A. W. Rihaczek, "Radar waveform selection—a simplified approach," *IEEE Trans. Aerosp. Electron. Syst.*, vol. AES-7, no. 6, pp. 1078-1086 (November 1971).

1—Constant-carrier pulse. This is the simplest form of the waveform that can be used and the form of a short duration of constant-carrier pulse is the excitation used in the conventional pulse-echo ultrasound imaging. This waveform allows for simple implementation or low complexity, good range resolution due to its large bandwidth, low sidelobe level with proper envelop and robustness to the frequency-dependent attenuation due to its short duration. Its disadvantage, lies in poor SNR resulting from lowest time-bandwidth (TBW) product possible: unity and high correlation in the imaging field.

2—Pulse compression signals with thumbtack ambiguity function. These waveforms have time-bandwidth product larger than unity, thus the may produce higher SNR than constant-carrier pulse. Sets of orthogonal codes are used to reduce the correlation in the field. A problem with this type of waveforms is high sidelobe level after compression: average approximately 1/TBW, although it is one type of waveform that achieves sharpest mainlobe peak. A special case in this family is complementary codes which are able to suppress sidelobe level by adding two or more transmitted sequences with equal-magnitude, opposite-sign sidelobes.

3—Pulse compression signal with sheared ridge ambiguity function—linear chirp. Linear chip is a special type of pulse compression signal because it has large time-bandwidth product as other pulse compression signals while it maintains low sidelobe level as the constant-carrier pulse. It is also robust to the frequency-dependent attenuation because the frequency shift mismatch can be translated to time shift, thus providing compression quality.

4—Pulse trains. This type of waveform has the capability of suppressing sidelobe level, at the same time, achieving sharp mainlobe peaks.

One may select exciting waveforms not only based on the above classifications, but also they may be selected by iteratively calibrating/training the system, obtaining spatio-temporal codes capable of correcting the distortion in heterogeneous, lossy medium such as described in Montaldo et al., "Spatio-temporal coding in complex media for optimum beamforming: the iterative time-reversal approach," *IEEE Trans. Ultrason., Ferroelect., Freq. Contr.*, vol. 52, no. 2, pp. 220-230 (February 2005); which manner of choosing coded waveform may cast light on optimum waveform design for specific applications/scenario.

Receive Filter

A matched filter may be used as the receiving/compressing filter because it achieves the highest SNR at the peak of the compressed pulses. The highest possible SNR is proportional to the time-bandwidth of the transmitted waveforms. However, matched filters may not take system noise or clutter distribution into account, and as such, this type of filter may not balance performance parameters for optimum solutions of specific applications. On the other hand, a pseudoinverse filter may be used that has the capability of combining compression, decoupling, noise/clutter reduction and performance adjustment at the same time.

Section C—Pseudoinverse Filter Design with Coded Excitation.

Figure 10:
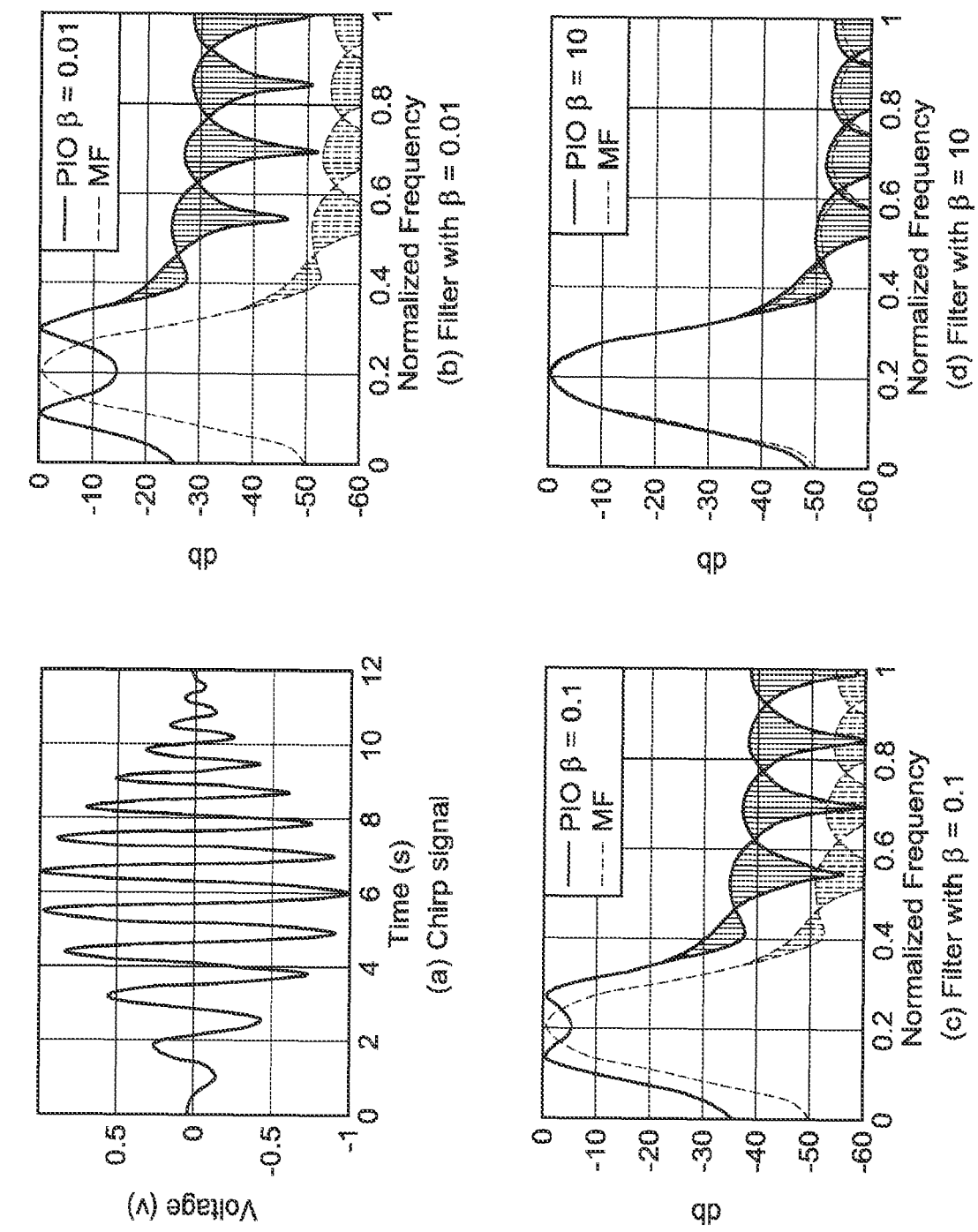

One can use a linear chirp signal as an example of coded waveform and illustrate the design of 1D pseudoinverse Filter as receive filtering transmitted coded excitation. A linear chirp signal c(t) covering the frequency band of 0.5-1.5 MHz may be transmitted as illustrated in FIGS. 10(*a*)-(*d*) (e.g., an illustration of the pseudoinverse compression filter frequency response designed for a Gaussian chirp transmit waveform). The effect of the regularization parameter, β, on the frequency response of the PIO is also shown.

The frequency response of the matched filter M(f) is C*(f), the complex conjugate of the Fourier transform of c(t. The frequency response of the pseudoinverse filter, P(f), is defined as $$P(f) = \frac{C*(f)}{S_s(f) + \beta S_n(f)},$$

where, $S_s(f)=|C(f)|^2$ is the spectral density of the signal, $S_n(f)$ is the spectral density of the noise and β is a regularization parameter for the noise term.

For illustration purpose, additive white Gaussian noise (AWGN) model is assumed. The above equation is basically the equation above for $\{Z_i\}_{k,k}$ with noise model being considered. As shown in FIG. 10, the frequency response of the pseudoinverse filter changes with the value of β. Specifically, when the regularization parameter β is set equal to 0, the filter behaves as an inverse filter, 1/C(f), with widest bandwidth and highest noise floor. The pulse width in the time domain is inversely proportional to the bandwidth. Therefore, theoretically, the inverse filter obtains the highest axial resolution but with the lowest SNR. On the other extreme, when the regularization parameter β is large enough so that $\beta S_n(f)$ dominates the denominator, the filter behaves as a matched filter as shown in FIG. 10(*d*). This solution maximizes the SNR, but may reduce the axial resolution (e.g., due to the reduced overall bandwidth of the system-matched filter cascade). The use of the pseudoinverse filter allows the shaping of the spectrum of the compressed received signal by regularized inversion of the system frequency response at frequencies where the SNR is sufficiently high. The appropriate value of β can be determined from the SNR of the system as a function of the frequency.

D—Image Formation

Synthetic aperture imaging. Synthetic aperture (SA) imaging techniques, as described in K. Thomenius, "Evolution of ultrasound beamformers," *IEEE Ultrason. Symp.*, pp. 1615-1622 (1996), may be used to obtain images with 2-way (i.e., transmit-and-receive) dynamic focusing. This may provide high quality images using conventional delay-and-sum beamforming. In this mode, the RF data from an image pixel at $P(x_p,z_p)$ in a medium with uniform speed of sound, c, is computed by:

$$I(x_p, z_p) = \sum_{i=1}^{64} \sum_{j=1}^{64} A_i \cdot B_j \cdot s_{i,j}\left(\frac{R_{ip} + R_{jp}}{c}\right),$$

where $A_i$ and $B_j$ are, respectively, the transmit and receive apodization weights, $R_{ip}$, and $R_{jp}$ are, respectively, the distances from the transmitting and receiving elements to the image pixel P, and $s_{i,j}$ is the echo received by element j when transmitting with element i. Other imaging scenarios can be performed by specializing the image formation as described, for example, in T. Misaridis and J. A. Jensen, "Use of modulated excitation signals in medical ultrasound. part I: basic concepts and expected benefits," *IEEE Trans. Ultrason., Ferroelect., Freq. Contr.*, vol. 52, no. 2, pp. 177-191 (February 2005). In the context of SA imaging, adaptive imaging may be performed by using distinct arbitrary waveforms on each element on transmit and pre-beamforming signal separation using the running DFT. The signal components obtained at the outputs of the running DFTs may be used in image-formation and compounding to allow for the evaluation of the performance measures (e.g., SNR and CR) with respect to the identified CPs. The signal may also be used in image reconstruction upon the convergence of the adaptive imaging algorithms.

Linear Array Imaging: Linear array imaging is widely used in pulse-echo medical ultrasound due to its simplicity and usefulness in many applications, e.g., vascular imaging, breast imaging, etc. It can be described with reference to FIG. 9 which shows a linear array and an imaging beam used to acquire one image line on a rectilinear grid in the axial and lateral directions. The pulse-echo data attributed to this image line may be obtained by using one transmit beam and employing dynamic receive focusing to maximize the field of view (FOV). In the context of linear array imaging, adaptive imaging may be performed by using arbitrary waveform generation on the transmitter side and post-beamforming separation of the echo components (e.g., using the running DFT) before compounding and/or performing image reconstruction of tissue properties.

Other Image Formation Methods: Conventional modern scanners employ other types of image formation models, e.g., phased array, convex, steered linear, etc. In each case, the adaptive imaging approach described herein may be applied as appropriate for the particulars of the transmit-receive methods used. The principles are the substantially same.

E—Assessment of Imaging Performance

Spatial resolution. For wire target images, the 6-dB width and length of the envelope may be used to measure the lateral and axial resolution, respectively. For quality assurance and scatterer phantoms the speckle correlation cell size as described in R. F. Wagner, M. F. Insana, and S. W. Smith, "Fundamental correlation lengths of coherent speckle in medical ultrasonic images," *IEEE Trans. Ultrason., Ferroelect., Freq. Contr.*, vol. 35, no. 1, pp. 34-44 (January 1988) may be used. Uniform speckle regions from the test object area may be identified to compute the average speckle correlation cell size in the axial and lateral directions as follows:

$$S_{cx} = \int_{-X}^{X} \frac{C_I(x, 0)}{C_I(0, 0)} dx$$

$$S_{cz} = \int_{-Z}^{Z} \frac{C_I(0, z)}{C_I(0, 0)} dz,$$

where $S_{cx}$ and $S_{cz}$ are, respectively, the lateral and axial cell size values and $C_I(x,z)$ is the 2D intensity autocovariance function. The integration limits X and Z may be chosen to be large enough to allow the magnitude of the autocovariance to drop to negligible levels. The integrals may be evaluated numerically in Cartesian coordinates using the trapezoidal rule to obtain the speckle cell size in the axial and lateral directions.

Contrast. The contrast ratio (CR) is defined as following:

$$CR = 10\log_{10}\left[\frac{\bar{I}_2}{\bar{I}_1}\right],$$

where $\bar{I}_2$ and $\bar{I}_1$ are the average intensities in the region of interest (e.g. cyst) and a reference region, respectively. This definition of the CR may be acceptable and applicable in imaging quality assurance phantom. For purposes of at least one embodiment of adaptive imaging, a definition of CR related to the selection of CPs (e.g. in the wall and lumen of a blood vessel) is shown herein in the description with reference to FIG. 3.

The SNR is typically computed from speckle statistics. Specifically, the envelope of the echo signal in a uniform speckle region follows Rayleigh statistics. The SNR is typically obtained from the ratio of the mean and the standard deviation in a uniform region. The SNR can also be evaluated by computing a ratio between the energies in the ROI and a reference region identified with noise. Both of these approaches to the computation of SNR may be useful in adaptive imaging.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An ultrasound imaging method comprising:
   providing a region of interest in a subject;
   defining a plurality of control points within the region of interest, wherein at least a first portion of the control points are associated with a first identifiable portion of the region of interest and a second portion of the control points are associated with a second identifiable portion of the region of interest that is different than the first identifiable portion;
   providing a transducer apparatus comprising a plurality of ultrasound transducer elements, wherein each of the plurality of ultrasound transducer elements is configured to deliver ultrasound energy to the region of interest in response to a waveform applied thereto;
   generating a waveform for each ultrasound transducer element of the plurality of ultrasound transducer elements, wherein generating the waveform comprises:
      selecting one or more imaging frequencies within a transducer apparatus bandwidth, each of the one or more imaging frequencies being a carrier of a pulse to be transmitted having a finite bandwidth within the transducer bandwidth and having a time duration; and
      generating element frequency components for each of the one or more imaging frequencies to form at least a part of the waveform to be applied to the ultrasound transducer element;
   delivering ultrasound energy in pulse mode to the region of interest using the plurality of ultrasound transducer elements in response to waveforms generated for each of the plurality of ultrasound transducer elements;
   receiving pulse-echo data at each ultrasound transducer element of a plurality of ultrasound transducer elements from the region of interest in response to the delivered ultrasound energy to generate an image based thereon;
   separating pulse-echo components received from at least one of the first portion of the control points associated with the first identifiable portion of the region of interest and received from the second portion of the control points associated with the second identifiable portion of the region of interest;
   determining at least one of a contrast ratio between the first and second identifiable portions based on the pulse-echo components received from the first portion of the control points associated with the first identifiable portion of the region of interest and the pulse-echo components received from the second portion of the control points associated with the second identifiable portion of the region of interest and a signal to noise ratio based on pulse-echo components received from a reference portion of the region of interest and pulse-echo components received from at least one of the first portion of the control points and the second portion of the control points; and
   modifying the waveform generated for one or more of the plurality of ultrasound transducer elements based on at least one of the contrast ratio and the signal to noise ratio.

2. The method of claim 1, wherein the method further comprises delivering therapy to a patient based on identification of at least one vascular characteristic of the region of interest in which at least one portion of a blood vessel is located.

3. A system for ultrasound imaging, comprising:
a transducer apparatus comprising a plurality of ultrasound transducer elements, wherein each of the plurality of ultrasound transducer elements is configured to deliver ultrasound energy to a region of interest in response to a waveform applied thereto resulting in pulse-echo data therefrom; and
processing apparatus configured to:
provide a region of interest in a subject such that a plurality of control points may be defined within the region of interest, wherein at least a first portion of the control points are associated with a first identifiable portion of the region of interest and a second portion of the control points are associated with a second identifiable portion of the region of interest that is different than the first identifiable portion;
generate a waveform for each ultrasound transducer element of the plurality of ultrasound transducer elements, wherein the processing apparatus is configured to generate the waveform by:
selecting one or more imaging frequencies within a transducer apparatus bandwidth, each of the one or more imaging frequencies being a carrier of a pulse to be transmitted having a finite bandwidth within the transducer apparatus bandwidth and having a time duration; and
generating element frequency components for each of the one or more imaging frequencies to form at least a part of the waveform to be applied to the ultrasound transducer element;
control delivery of ultrasound energy in pulse mode to the region of interest using the plurality of ultrasound transducer elements in response to waveforms generated for each of the plurality of ultrasound transducer elements;
control capture of pulse-echo data at each ultrasound transducer element of a plurality of ultrasound transducer elements from the region of interest in response to the delivered ultrasound energy to generate an image based thereon;
separate pulse-echo components received from at least one of the first portion of the control points associated with the first identifiable portion of the region of interest and received from the second portion of the control points associated with the second identifiable portion of the region of interest;
determine at least one of a contrast ratio between the first and second identifiable portions based on the pulse-echo components received from the first portion of the control points associated with the first identifiable portion of the region of interest and the pulse-echo components received from the second portion of the control points associated with the second identifiable portion of the region of interest and a signal to noise ratio based on pulse-echo components received from a reference portion of the region of interest and pulse-echo components received from at least one of the first portion of the control points and the second portion of the control points; and modify the waveform generated for one or more of the plurality of ultrasound transducer elements based on at least one of the contrast ratio and the signal to noise ratio.

4. The system of claim 3, wherein the system is configured to compare at least the signal to noise ratio to a threshold value and the waveform generated for one or more of the plurality of ultrasound transducer elements is modified based on the comparison.

5. The system of claim 3, wherein the system is configured to compare at least the contrast ratio determined between the first and second identifiable portions to a threshold value and the waveform generated for one or more of the plurality of ultrasound transducer elements is modified based on the comparison.

6. The system of claim 3, wherein the first portion of the control points are associated with a vessel wall of a vascular structure of the subject and the second portion of the control points are associated with a lumen defined at least in part by the vessel wall.

7. The system of claim 6, wherein the plurality of control points within the region of interest further comprise a third portion of the control points associated with tissue surrounding the vessel wall of the vascular structure, wherein pulse-echo components received from the third portion of the control points associated with the tissue are separated from the pulse-echo components received from other portions of the control points, and further wherein, at least a contrast ratio between the tissue and at least one of the vessel wall or lumen is determined for use in modifying the waveform generated for one or more of the plurality of ultrasound transducer elements.

8. The system of claim 3, wherein modifying the waveform generated for one or more of the plurality of ultrasound transducer elements comprises at least one of adjusting gain at frequencies of the one or more frequencies located at one or more locations within the transducer apparatus bandwidth, adjusting one or more pulse parameters including at least one of pulse duration, pulse shape, pulse amplitude, and pulse phase to adjust time-bandwidth product to improve at least one of contrast ratio or signal to noise ratio.

9. The system of claim 3, wherein the system is further configured for:
separating, from the pulse echo data received, at least a portion thereof received at each ultrasound transducer element from the region of interest in response to the delivered ultrasound energy corresponding to a single frequency of the one or more image frequencies; and
reconstructing an image representative of one or more properties in the region of interest from the separated pulse-echo data corresponding to the single frequency of the one or more image frequencies.

10. The system of claim 3, wherein generating element frequency components for each of the one or more imaging frequencies to form at least a part of the waveform to be applied to the ultrasound transducer element comprises generating one or more excitation vectors, and further wherein generating the one or more excitation vectors comprises generating each excitation vector using field synthesis at a single frequency of the one or more imaging frequencies within the transducer bandwidth.

11. The system of claim 10, wherein the excitation vector generated comprises an element frequency component corresponding to each ultrasound transducer element of the plurality of ultrasound transducer elements.

12. The system of claim 3, wherein the system is further configured to deliver therapy to a patient based on identification of at least one vascular characteristic of the region of interest in which at least one portion of a blood vessel is located.

13. The system of claim 12, wherein using ultrasonic energy to deliver therapy comprises using the transducer apparatus to deliver ultrasound energy and receive pulse-echo data and to generate ultrasonic energy to deliver therapy.

14. The system of claim 3, wherein controlling capture of pulse-echo data at each ultrasound transducer element of a plurality of ultrasound transducer elements from the region of interest in response to the delivered ultrasound energy comprises using a discrete Fourier transform based filter bank for separation of pulse-echo data.

15. The system of claim 3, wherein the one or more imaging waveforms comprise a finite number of randomly selected single frequency components, each single frequency component being a carrier having a finite bandwidth specified by its duration and modulating pulse.

* * * * *